(12) United States Patent
Saunders et al.

(10) Patent No.: US 7,183,393 B2
(45) Date of Patent: *Feb. 27, 2007

(54) CONSTRUCTION AND USE OF SYNTHETIC CONSTRUCTS ENCODING SYNDECAN

(75) Inventors: Scott Saunders, Creve Coeur, MO (US); Merton Bernfield, Boston, MA (US); Masato Kato, Hawthorne (AU)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/776,989

(22) Filed: Feb. 11, 2004

(65) Prior Publication Data

US 2005/0075484 A1 Apr. 7, 2005

Related U.S. Application Data

(60) Division of application No. 09/723,677, filed on Nov. 28, 2000, now Pat. No. 6,699,968, which is a continuation of application No. 08/471,970, filed on Jun. 6, 1995, now Pat. No. 6,531,295, which is a division of application No. 08/078,683, filed on Jun. 17, 1993, now Pat. No. 5,486,599, which is a continuation-in-part of application No. 07/856,869, filed on Mar. 24, 1992, now abandoned, which is a continuation-in-part of application No. 07/757,654, filed on Sep. 6, 1991, now abandoned, which is a continuation-in-part of application No. 07/331,585, filed on Mar. 29, 1989, now abandoned.

(51) Int. Cl.
| | |
|---|---|
| C07K 14/00 | (2006.01) |
| C07K 19/00 | (2006.01) |
| A61K 38/00 | (2006.01) |
| A61K 38/03 | (2006.01) |
| A61K 38/16 | (2006.01) |
| C12P 21/00 | (2006.01) |

(52) U.S. Cl. ............... 530/395; 530/350; 530/399; 530/402; 435/69.1; 435/69.7

(58) Field of Classification Search ............... 530/300, 530/350, 351, 380, 395, 394, 402; 435/69.1, 435/69.4, 69.5, 69.7, 69.8; 514/2, 19, 56; 424/278.1, 279.1
See application file for complete search history.

(56) References Cited

U.S. PATENT DOCUMENTS

| 4,336,336 A | 6/1982 | Silhvay et al. ............ 435/172 |
| 4,840,941 A | 6/1989 | Ueno et al. ............ 514/59 |
| 4,956,347 A | 9/1990 | Ban et al. ............ 514/54 |
| 5,486,599 A * | 1/1996 | Saunders et al. ........... 530/395 |
| 6,699,968 B1 * | 3/2004 | Saunders et al. ........... 530/350 |

FOREIGN PATENT DOCUMENTS

| WO | WO 90/07712 | 7/1990 |
| WO | WO 90/12033 | 10/1990 |
| WO | WO 93/05167 | 3/1993 |

OTHER PUBLICATIONS

Murdoch et al., Journal of Biological Chemistry, vol. 267 No. 2, pp. 8544-8557 (Apr. 1992).*
Roberts et al., Nature, vol. 332 No. 6162, pp. 376-378 (Mar. 1988).*
Bowie et al., "Decifering the Message inProtein Sequences: olerance to Amino Acid Substitution," Science, vol. 247, pp. 1306-1310 (1990).*
Ayotte, L., et al., "N.M.R. Spectroscopic Observations Related to the Function of Sulfate Groups in Heparin. Calcium Binding vs. Biological Activity" (1986) *Carbohydrate Res* vol. 145 :267-277.
Bernfield, M., et al., "Biology of the Syndecans: A Family of Transmembrane Heparan Sulfate Proteoglycans" (1992) *Annu. Rev. Cell Biol*, vol. 8:365-393.
Bernfield, M., et al., "Syndecan, a Developmentally Regulated Cell Surface Proteoglycan That Binds Extracellular Matrix and Growth Factors" (1990) *Phil. Trans. R. Soc. Lond.*, vol. B327:171-186.

(Continued)

*Primary Examiner*—Bruce R. Campell
*Assistant Examiner*—Zachariah Lucas
(74) *Attorney, Agent, or Firm*—Thomas J. Engellenner; Deborah A. Miller; Nutter McClennen & Fish, LLP

(57) ABSTRACT

A purified mammalian proteoglycan, and genetic information encoding such proteoglycans, having a core polypetide molecular weight of about 30 kD to about 35 kD, and comprising a hydrophilic amino terminal extracellular region, a hydrophilic carboxy terminal cytoplasmic region, a transmembrane hydrophobic region between said cytoplasmic and extracellular regions, a protease susceptible cleavage sequence extracellularly adjacent the transmembrane region of the peptide, and at least one glycosylation site for attachment of a heparan sulfate chain to said extracellular region, said glycosylation site comprising a heparan sulfate attachment sequence represented by a formula Xac-Z-Ser-Gly-Ser-Gly (SEQ ID NO: 44), where Xac represents an amino acid residue having an acidic sidechain, and Z represents from 1 to 10 amino acid residues. Additional peptides having this glycosylation site and genetic information useful for preparing a number of variations based on this glycosylation site are also provided.

16 Claims, 4 Drawing Sheets

OTHER PUBLICATIONS

Bourdon, M.A., "Structure and Role of Cloned Small Proteoglycans" (1990) *Extracellular. Matrix Genes*, Academic Press, Inc., 157-174.

Cary, D.J., et al., "Molecular Cloning and Characterization of N-Syndecan, a Novel Transmembrane Heparan Sulfate Proteoglycan" (1992) *J. Cell Bio.*, vol. 117, No. 1:191-201.

Cizmeci-Smith, G., et al., "Regular Expression of Syndecan in Vascular Smooth Muscle Cells and Cloning of Rat Syndecan Core Protein cDNA" (1992) *J. Biolog. Chem.*, vol. 267, No. 22:15729-15736.

David, g., et al., "Molecular Cloning of Amphiglycan, a Novel Integral Membrane Heparan Sulfate Proteoglycan Expressed by Epithelial and Fibroblastic Cells" (Aug. 1992) *J. Cell Bio.*, vol. 118, No. 4:961-969.

Fransson, L., et al., "o-L-Iduronate Ring Conformations in Heparin and Heparin Derivatives" (1978) *Biochem. J.*, vol. 175:299-309.

Fransson, L., "Periodate Oxidation of the D-Glucuronic Acid Residues in Heparan Sulphate and Heparin" (1978) *Carb. Res.*, vol. 62:235-244.

Gamse, G., et al., "Metabolism of Sulfated Glycosaminoglycans in Cultured Endothelial Cells and Smooth Muscle Cells From Bovine Aorta" (1978) *Biochimica et Biophysica Acta*, vol. 544:514-528.

Gould, S., et al., "Syndecan 3: A Member of the Syndecan Family of Membrane-Intercalated Proteoglycans that is Expressed in High Amounts at the Onset of Chicken Limb Cartilage Differentiation" (1992) *PNAS*, vol. 89:3271-3275.

Hardingham, T., et al., "Proteoglycans: Many Forms and Many Functions" (Feb. 1992) *FASEB J.*, vol. 6:861-870.

Ishihara, M., et al., "A Cell-Based Assay for Evaluating the Interaction of Heparin-like Molecules and Basic Fibroblast Growth Factor" (1992) *Annal. Biochem.*, vol. 202:310-315.

Jalkanen, M., et al., "Cell Surface Proteoglycan of Mouse Mammary Epithelial Cells is Shed by Cleavage of Its Matrix-binding Ectodomain from Its Membrane-associated Domain" (Dec. 1987) *J. Cell Bio.*, vol. 105, No. 6:PT 2:3087-3096.

Jalkanen, M., "Mouse Mammary Epithelial Cells Produce Basement Membrane and Cell Surface Heparan Sulfate Proteoglycans Containing Distinct Core Proteins" (Mar. 1988) *J. Cell Bio.*, vol. 106:953-962.

Kato, M., et al., "Polymorphism of Syndecan: A Distinctive Form on Mesenchymal Cells" (1989) *Abstract: J. Cell Biol.*, vol. 190, No. 3209: Abstract #1757.

Kiefer, M., et al., "Ligand-affinity Cloning and Structure of a Cell Surface Heparan Sulfate Proteoglycan that Binds Basic Fibroblast Growth Factor" (Sep. 1990) *PNAS*, vol. 87:6985-6989.

Kim, C.W., et al., "Members of the Syndecan Family of Heparan Sulfate Proteoglycans are Expressed in Distinct Cell-, Tissue-, and Development-Specific Patterns" (Jul. 1994) *Mol. Biol. Cell*, vol. 5, No. 7: 797-805.

Koda, J., et al., "Heparan Sulfate Proteoglycans from Mouse Mammary Epithelial Cells" (1985) *J. Bio. Chem.*, vol. 260, No. 13:8157-8162.

Kojima, T., et al., "Molecular Cloning and Expression of Two Distinct cDNA-encoding Heparan Sulfate Proteoglycan Core Proteins from a Rat Endothelial Cell Line" (1992) *J. Biol. Chem.*, vol. 267, No. 7: 4870-4877.

Kokenyesi, R. et al., "Core Protein Structure and Sequence Determine the Site and Presence of Heparan Sulfate and Chondroitin Sulfate on Syndecan-1" (1994) *J. Biol. Chem.*, vol. 269, No. 16: 12304-12309.

Linhardt, R., J., et al., "Examination of the Substrate Specificity of Heparin and Heparan Sulfate Lyases" (1990) *Biochem.*, vol. 29:2611-2617.

Lories, V., et al., "Differential Expression of Cell Sulfate Proteoglycans from Human Vascular Endothelial Cells and Lung Fibroblasts" (1992) *J. Biolog. Chem.*, vol. 267, No. 2:1116-1122.

Mali, M., et al., "Sequence of Human Syndecan Indicates a Novel Gene Family of Integral Membrane Proteogycans" (1990) *J. Biolog. Chem.*, vol. 265, No. 12:6884-6889.

Mertens, G., et al., "Cell Surface Heparan Sulfate Proteoglycans from Human Vascular Endothelial Cells" (1992) *J. Biolog. Chem.*, vol. 267, No. 28:20435-20443.

Olwin, B., et al., "Repression of Myogenic Differentiation by aFGF, bFGF, and K-FGF Is Dependent on Cellular Heparan Sulfate" (Aug. 1992) *J. Cell Bio.*, vol. 118, No. 3:631-639.

Pierce, A., et al., "Molecular Cloning of the Major Cell Surface Heparan Sulfate Proteoglycan from Rat Liver" (1992) *J. Biolog. Chem.*, vol. 267, No. 6:3894-3900.

Rapraeger, A., et al., "Cell Surface Proteoglycan of Mammary Epithelial Cells" (1985) *J. Biolog. Chem.*, vol. 260, No. 7:4103-4109.

Ross, C., et al., "Purification of a Basic Fibroblast Growth Factor-Binding Proteoglycan from Bovine Cardiac Plasma Membrane" (1993) *Biochimica et Biophysica Acta*, vol. 1145:219-226.

Salmivirta, M., et al., "Basic Fibroblast Growth Factor-Syndecan Complex at Cell Surface or Immobilized to Matrix Promotes Cell Growth" (1992) *J. Biolog. Chem.*, vol. 267, No. 25:17606-17610.

Sanderson, R., et al., "Molecular Polymorphism of a Cell Surface Proteoglycan: Distinct Structures on Simple and Stratified Epithelia" (Dec. 1988) *PNAS*, vol. 85:9562-9566.

Sanderson, R., et al., "Syndecan-1, a Cell-Surface Proteoglycan, Changes in Size and Abundance when Keratinocytes Stratify" (1992) *J. Invest. Derematol.*, vol. 99, No. 4:390-396.

Saunders, S., et al., "Cell-Surface Proteoglycan Binds Mouse Mammary Epithelial Cells to Fibronectin and Bahaves as a Receptor for Interstitila Matrix" (Feb. 1988) *J. Cell Bio.*, vol. 106:423-430.

Saunders, S., et al., "Molecular Cloning of Syndecan, an Integral Membrane Proteoglycan" (Apr. 1989) *J. Cell. Bio.*, vol. 108; 1547-1556.

* cited by examiner

Figure 2

```
                 1                                                    50
{Hu-Syndecan-1}  ....pqivatnlppEDqdGsgDDsDnFSgSGaGaLqditlsqqtPstwkd
{Rt-Syndecan-1}  ....pqivtanvppEDqdGsgDDsDnFSgSGtGaLpdmtlsrqtPstwkd
{Mu-Syndecan-1}  ....pqivavnvppEDqdGsgDDsDnFSgSGtGalpd.tlsrqtPstwkd
{Gh-Syndecan-1}  ....pqivtvnvppEDqdGsgDDsDnFSgSGtGaLpditlsrqasptlkd
{Hu-Syndecan-4}  ......yfsgalpDDEDvvGpgqEsDDFelSGSGdIdDiedsmigPevvhp
{RT-Syndecan-4}  ......yfsgalpDDEDagGleqDsD.FelSGSGdLddteeprtfPevisp
{CH-Syndecan-3}  ....rpvdleggDDDpfGdDElDDIYSGSGyFeqesgletavslttd
{HU-Syndecan-2}  ...dmyldnssieEasgvYpiDDdDyaSaSGSG.....adedvesPeIttt
{RT-Syndecan-2}  ...dmyldsssieEasglypiDDdDySaSGSG......ayedkgsPdltts
{MU-Syndecan-2}  ...dmyldnssieEasgvYpiDDdDySaSGSG.....adediesPvltts
{Fr-Syndecan-2}  ....yidst...EssgmypvDDdDysgSGSGipargdedenvvlttv
```

```
                            1                                              40
Murine Syndecan-1   MRRAALWLWL CALALRLQPA LPQIVaVNVP PEDQDGSGDD
Rat Syndecan-1      MRRAALWLWL CALALRLQPA LPQIVtaNVP PEDQDGSGDD
Hamster Syndecan-1  MRRAALWLWL CALALRLPQv LPQIVtVNVP PEDQDGSGDD
Human Syndecan-1    MRRAALWLWL CALALsLQIA LPQIVatNIP PEDQDGSGDD 41                                             80
Murine Syndecan-1   SDNFSGSGTG ALPD.TLSRQ TPSTWKDVWL LTATPTAPEP
Rat Syndecan-1      SDNFSGSGTG ALPDmTLSRQ TPSTWKDVWL LTATPTAPEP
Hamster Syndecan-1  SDNFSGSGTG ALPDITLSRQ aspTlKDVWL LTATPTAPEP
Human Syndecan-1    SDNFSGSGaG ALqDITLSqQ TPSTWKDtql LTAiPTsPEP 81                                             120
Murine Syndecan-1   TSsntEtaFT SVLPAGEKPE EGEPVLHVEa EPGFTARDKE
Rat Syndecan-1      TSRDtEAtLT SILPAGEKPE EGEPVaHVEa EPdFTARDKE
Hamster Syndecan-1  TSRDaqAttT SILPAaEKPG EGEPVLtaEv EPGFTARDKE
Human Syndecan-1    TqlEatAasT StLPAGEgPk EGEaVvlpEv EPGLTAR..E 121                                            160
Murine Syndecan-1   KEvTTRPRET vQLPITqrAS T.vRVTTAQA aVTSHPHggm
Rat Syndecan-1      KEaTTRPRET TQLPVTqqAS TaARATTAQA sVTSHPHgDv
Hamster Syndecan-1  sEvTTRPRET TQLlIThwvS T.ARATTAQA PVTSHPHrDv
Human Syndecan-1    qEatpRPRET TQLPtThqAS Ttt.ATTAQe PaTSHPHrDm 161                                            200
Murine Syndecan-1   QPGLHETSAP TAPGQPDHQP PrVEgGGTSV IKEVvEDGta
Rat Syndecan-1      QPGLHETlAP TAPGQPDHQP PSVEDGGTSV IDEVvEDetT
Hamster Syndecan-1  QPGLHETSAP TAPGQPDqQp PS...GGTSV IKEVaEDGaT
Human Syndecan-1    QPGhHETStP agPsQaDlht PhtEDGGpSa teraaEDGas 201                                            240
Murine Syndecan-1   NQLPAGEGSG EQDFTFETSG ENTAVAAVEP gLRNQpPVDE
Rat Syndecan-1      NQLPAGEGSG EQDFTFETSG ENTAVAgVEP DLRNQsPVDE
Hamster Syndecan-1  NQLPtGEGSG EQDFTFETSG ENTAVAAVEP DqRNQsPVDE
Human Syndecan-1    sQLPAaEGSG EQDFTFETSG ENTAVvAVEP DrRNQsPVDq 241                                            280
Murine Syndecan-1   GATGASQsLL DRKEVLGGVI AGGLVGLIFA VCLVaFMLYR
Rat Syndecan-1      GATGASQGLL DRKEVLGGVI AGGLVGLIFA VCLVaFMLYR
Hamster Syndecan-1  GATGASQGLL DRKEVLGGVI AGGLVGLIFA VCLVgFMLYR
Human Syndecan-1    GATGASQGLL DRKEVLGGVI AGGLVGLIFA VCLVgFMLYR 281                                            313
Murine Syndecan-1   MKKKDEGSYS LEEPKQANGG AYQKPTKQEE FYA
Rat Syndecan-1      MKKKDEGSYS LEEPKQANGG AYQKPTKQEE FYA
Hamster Syndecan-1  MKKKDEGSYS LEEPKQANGG AYQKPTKQEE FYA
Human Syndecan-1    MKKKDEGSYS LEEPKQANGG AYQKPTKQEE FYA
```

FIGURE 3

| Examples f extracellular matrix molecules that bind to heparin/heparan sulfate and interact with cells via specific surface receptors ||||
|---|---|---|---|
| ●Collagen types I, II, III, V | ●Tenascin | ●Fibronectin | ●SPARC |
| ●Laminin | ●Thrombospondin | ●Entactin (nidogen) | ●Wnt-1 |
| ●Vitronectin | ●Pleiotropin | | |

| Examples of growth factors that bind to heparin/heparan sulfate and that interact with cells via specific surface receptors ||
|---|---|
| ●Basic fibroblast growth factor (bFGF) | ●Platelet derived growth factor isoforms (PDGF) |
| ●Acidic fibroblast growth factor (aFGF) | ●Heparin-binding EGF-like growth factor (HB-EGF) |
| ●Keratinocyte growth factor (KGF) | ●Vascular endothelial growth factor isoforms (VEGF) (Vascular permeability factor, VPF) |
| ●hst/K-fgf | ●Transforming growth factor β isoforms (TGF-β) |
| ●int-2 | ●Schwannoma-derived growth factor (amphiregulin) |
| ●FGF-5 | ●Interferon gamma |
| ●FGF-6 | ●Interleukin-3 |
| ●Hepatocyte growth factor (scatter factor) | ●Granulocyte-macrophage colony stimulating factor (GMCSF) |

| Examples of cell adhesion molecules that bind to heparin/heparan sulfate and that interact with cells via specific surface receptors |
|---|
| ●Neural cell adhesion molecule (N-CAM) |
| ●Platelet-endothelium cell adhesion molecule (PECAM) |

| Examples of lipid metabolism molecules that bind to heparin/heparan sulfate |||
|---|---|---|
| ●Apolipoprotein B (apoB) | ●Cholesterol esterase | ●Apolipoprotein E (apoE) |
| ●Triglyceride lipase | ●Lipoprotein lipase | |

| Examples of degradative enzymes that bind to heparin/heparan sulfate ||
|---|---|
| ●Acetylcholinesterase | ●Extracellular superoxide dismutase |

| Examples of protease inhibitors that bind to heparin/heparan sulfate |||
|---|---|---|
| ●Thrombin | ●Heparin cofactor II | ●Factor Xa |
| ●Leuserpin | ●Tissue plasminogen activator | ●Plasminogen activator inhibitor-1 (PAI-1) |
| ●Antithrombin III | ●Lipoprotein-associated coagulation inhibitor (LACI) | |

| Examples of proteins that bind to heparin/heparan sulfate or their relevant microbial pathogens ||
|---|---|
| ●Glycoproteins C and B (gC and gB) of herpes simplex virus types I and II | ●Circumsporozoite protein of Plasmodium falciparum |
| ●Glycoprotein CII (gC-II) of cytomegalovirus | ●Adhesion protein of Trypanosoma gondii |
| ●Glycoprotein 120 (gp120) of human immunodeficiency virus | ●Adhesion proteins of Bordetella pertussis, Streptococcus pyogenes, and Staphylococcus aureous |

FIGURE 4

CONSTRUCTION AND USE OF SYNTHETIC CONSTRUCTS ENCODING SYNDECAN

REFERENCE TO RELATED APPLICATIONS

This application is a divisional of U.S. application Ser. No. 09/723,677, filed Nov. 28, 2000, now U.S. Pat. No. 6,699,968, which is a continuation of U.S. patent application Ser. No. 08/471,970, filed Jun. 6, 1995, now U.S. Pat. No. 6,531,295, which is a divisional of U.S. patent application Ser. No. 08/078,683, filed Jun. 17, 1993, now U.S. Pat. No. 5,486,599, which is a continuation-in-part of U.S. patent application Ser. No. 07/757,654 filed Sep. 6, 1991, now abandoned, and is a continuation-in-part of U.S. patent application Ser. No. 07/856,869 filed Mar. 24, 1992, now abandoned, which is a continuation-in-part of application Ser. No. 07/746,797 filed Aug. 12, 1991, now abandoned, which is a continuation-in-part of application Ser. No. 07/331,585 filed Mar. 29, 1989, now abandoned. All of the above-referenced patent applications are hereby incorporated by reference.

Work leading to the present invention was supported in part by a National Institutes of Health grant. The government has rights in this invention as a result of this support.

BACKGROUND OF THE INVENTION

1. Field of the Invention

This invention relates to the field of proteoglycans and of cell surface receptors for biological effector molecules, more particularly the use of genetic engineering to define a class of proteoglycans and their constituent functional domains, particularly their glycosaminoglycan attachment regions. The invention includes the use of recombinant DNA vectors to produce proteins in prokaryotic cells and proteoglycans in eukaryotic cells, and a variety of techniques to link the functional domains to biological effector molecules, cell surface receptors, drugs, antibodies, diagnostic agents, and components of microorganisms.

2. Description of the Background

The cellular behavior responsible for the development, repair and maintenance of tissues is regulated, in large part, by interactions between cells and components of their microenvironment. These interactions are mediated by cell surface molecules acting as receptors that bind large insoluble matrix molecules, growth factors, enzymes, and other molecules that induce responses which result in changes of cellular phenotype. Several proteins associated with the cell surface can bind these components. These proteins differ in their specificity and affinity and in their mode of association with the cell surface.

The present inventors have studied a lipophilic proteoglycan containing both heparan sulfate and chondroitin sulfate that is found at the surface of mouse mammary epithelial cells and that behaves as a high affinity receptor specific for multiple components of the interstitial matrix. This proteoglycan has been given the name syndecan-1. The proteoglycan binds the epithelial cells via its heparan sulfate chains to collagen types I, III, and V (Koda, J. E., Rapraeger, A., and Bernfield, M., *J. Biol. Chem.* (1985) 260: 8157–8162), fibronectin (Saunders, S. and Bernfield, M., *J. Cell Biol.* (1988) 106: 423–430), and thrombospondin. When its extracellular domain (ectodomain) is cross-linked at the cell surface, it associates intracellularly with the actin cytoskeleton, and the isolated proteoglycan binds directly or indirectly to F-actin (Rapraeger, A., and Bernfield, M., *J. Biol. Chem.* (1985) 260: 4103–4109). Cultured cells shed the ectodomain from their apical surfaces as a nonlipophilic proteoglycan that contains all of the glycosaminoglycan of the intact molecule. Upon suspension of these cells, the extracellular domain is cleaved from the cell surface; the proteoglycan is not replaced while the cells are suspended (Jalkanen, M., Rapraeger, A., Saunders, S., and Bernfield, M., *J. Cell Biol.* (1987) 105: 30873096). The proteoglycan is mainly on epithelia in mature tissues (Hayashi, K., Hayashi, M., Jalkanen, M., Firestone, J. H., Trelstad, R. L., and Bernfield, M., *J. Histochem. Cytochem.* (1987) 35: 1079–1088).

Syndecan-1 undergoes substantial regulation; its size, glycosaminoglycan composition and location at the cell surface vary between cell types, and its expression changes during development. The proteoglycan is located exclusively at the basolateral cell surface of simple epithelia but surrounds stratified epithelial cells. At basolateral cell surfaces, it appears to contain two heparan sulfate and two chrondroitin sulfate chains, but where it surrounds cells, it contains only a single heparan sulfate chain and a single small chrondroitin sulfate chain (Sanderson, R. D., and Bernfield, M., *Proc. Natl. Acad. Sci. USA* (1987) 238: 491–497). In self-renewing epithelial cell populations, such as the epidermis or vagina, the proteoglycan is lost when the cells terminally differentiate (Hayashi, K., Hayashi, M., Boutin, E., Cunha, G. R., Bernfield, M., and Trelstad, R. L., *J. Lab. Invest.* (1988) 58: 68–76). In embryos, the proteoglycan is transiently lost when epithelia change their shape and is transiently expressed by mesenchymal cells undergoing morphogenetic tissue interaction.

Heparan sulfate proteoglycans are ubiquitous on the surfaces of adherent cells and bind various ligands including extracellular matrix, growth factors, proteinase inhibitors, and lipoprotein lipase; see Fransson, L., *Trends Biochem. Sci.* (1987) 12: 406411, Bernfield et al. (1992) *Annu. Rev. Cell. Biol.* 8:365–93 However, despite much study of these molecules, no structure was known for the core protein prior to this invention of any such cell surface proteoglycan.

For general background on genetic engineering, see Watson, J. D., *The Molecular Biology of the Gene,* 4th Ed., Benjamin, Menlo Park, Calif., (1988).

SUMMARY OF THE INVENTION

Accordingly, it is an object of this invention to provide eukaryotic cells capable of providing useful quantities of syndecan-1 and proteins of similar function from multiple species.

It is a further object of this invention to provide a recombinant DNA vector containing a heterologous segment encoding syndecan-1 or a related protein that is capable of being inserted into a microorganism or eukaryotic cell and expressing the encoded protein.

It is still another object of this invention to provide a DNA or RNA segment of defined structure that can be produced synthetically or isolated from natural sources and that can be used in the production of the desired recombinant DNA vectors or that can be used to recover related genes from other sources.

It is yet another object of this invention to provide a peptide that can be produced synthetically in a laboratory or by a microorganism which will mimic the activity of natural syndecan-1 core protein and which can be used to produce proteoglycans and glycosaminoglycans in eukaryotic cells in a reproducible and standardized manner.

It is yet a further object of this invention to provide novel heparan sulfate attachment sequences which are identified by combinatorial mutagenesis.

It is another object of this invention to provide chimeric molecules which comprise at least a heparan sulfate glycosaminoglycan chain derived from a syndecan. The chimeric molecule can be, by way of illustration, a fusion protein which includes a functional heparan sulfate attachment sequence placed into other proteins which normally do not have heparan sulfate glycosaminoglycan chains.

It is yet a further object of this invention to provide therapeutic agents comprising heparan sulfate glycosaminoglycans to act agonistically or antagonistically to a biological activity.

These and other objects of the invention as will hereinafter become more readily apparent have been accomplished by providing an isolated proteoglycan having a core polypetide molecular weight of about 30 kD to about 35 kD, and comprising a hydrophilic amino terminal extracellular region, a hydrophilic carboxy terminal cytoplasmic region, a transmembrane hydrophobic region between said cytoplasmic and extracellular regions, a protease susceptible cleavage sequence extracellularly adjacent the transmembrane region of the peptide, and at least one glycosylation site for attachment of a heparan sulfate chain to said extracellular region, said glycosylation site comprising a heparan sulfate attachment sequence represented by a formula Xac-Z-Ser-Gly-Ser-Gly (SEQ ID NO: 44), where Xac represents an amino acid residue having an acidic sidechain, and Z represents from 1 to 10 amino acid residues. The proteoglycan can include at least one heparan sulfate glycosaminoglycan attached at said glycosylation site, as well as at least one chondroitin sulfate glycosaminoglycan attached at other sites on the protein.

Particularly preferred are peptides of
(a) a first formula:

(amino acids 1–311 of SEQ ID NO: 2)
M-R-R-A-A-L-W-L-W-L-C-A-L-A-L-R-L-Q-P-A-L-P-Q-I-V-A-V-N-V-P-P-E-D-
Q-D-G-S-G-D-D-S-D-N-F-S-G-S-G-T-G-A-L-P-D-T-L-S-R-Q-T-P-S-T-W-K-D-
V-W-L-L-T-A-T-P-T-A-P-E-P-T-S-S-N-T-E-T-A-F-T-S-V-L-P-A-G-E-K-P-E-
E-G-E-P-V-L-H-V-E-A-E-P-G-F-T-A-R-D-K-E-K-E-V-T-T-R-P-R-E-T-V-Q-L-
P-I-T-Q-R-A-S-T-V-R-V-T-T-A-Q-A-A-V-T-S-H-P-H-G-G-M-Q-P-G-L-H-E-T-
S-A-P-T-A-P-G-Q-P-D-H-Q-P-P-R-V-E-G-G-G-T-S-V-I-K-E-V-V-E-D-G-T-A-
N-Q-L-P-A-G-E-G-S-G-E-Q-D-F-T-F-E-T-S-G-E-N-T-A-V-A-A-V-E-P-G-L-R-
N-Q-P-P-V-D-E-G-A-T-G-A-S-Q-S-L-L-D-R-K-E-V-L-G-G-V-I-A-G-G-L-V-G-
L-I-F-A-V-C-L-V-A-F-M-L-Y-R-M-K-K-K-D-E-G-S-Y-S-L-E-E-P-K-Q-A-N-G-
G-A-Y-Q-K-P-T-K-Q-E-E-F-Y-A.

(b) a second formula:

(amino acids 23–311 of SEQ ID NO: 2)
Q-I-V-A-V-N-V-P-P-E-D-Q-D-G-S-G-D-D-S-D-N-F-S-G-S-G-T-G-A-L-P-D-T-
L-S-R-Q-T-P-S-T-W-K-D-V-W-L-L-T-A-T-P-T-A-P-E-P-T-S-S-N-T-E-T-A-F-
T-S-V-L-P-A-G-E-K-P-E-E-G-E-P-V-L-H-V-E-A-E-P-G-F-T-A-R-D-K-E-K-E-
V-T-T-R-P-R-E-T-V-Q-L-P-I-T-Q-R-A-S-T-V-R-V-T-T-A-Q-A-A-V-T-S-H-P-
H-G-G-M-Q-P-G-L-H-E-T-S-A-P-T-A-P-G-Q-P-D-H-Q-P-P-R-V-E-G-G-G-T-S-
V-I-K-E-V-V-E-D-G-T-A-N-Q-L-P-A-G-E-G-S-G-E-Q-D-F-T-F-E-T-S-G-E-N-
T-A-V-A-A-V-E-P-G-L-R-N-Q-P-P-V-D-E-G-A-T-G-A-S-Q-S-L-L-D-R-K-E-V-
L-G-G-V-I-A-G-G-L-V-G-L-I-F-A-V-C-L-V-A-F-M-L-Y-R-M-K-K-K-D-E-G-S-
Y-S-L-E-E-P-K-Q-A-N-G-G-A-Y-Q-K-P-T-K-Q-E-E-F-Y-A.

(c) a third formula in which at least one amino acid in said first formula or said second formula is replaced by a different amino acid, with the proviso that the replacements do not substantially alter attachment of a syndecan heparan sulfate glycosaminoglycan chain to the proteoglycan, (d) a fourth formula in which from 1 to 15 amino acids are absent from either the amino terminal, the carboxy terminal, or both terminals of said first formula, said second formula, or said third formula, or (e) a fifth formula in which from 1 to 10 additional amino acids are attached sequentially to the amino terminal, carboxy terminal, or both terminals of said first formula, said second formula, or said third formula, as well as salts of compounds having said formulas.

DNA and RNA molecules, recombinant DNA vectors, and modified microorganisms or eukaryotic cells comprising a nucleotide sequence that encodes any of the peptides indicated above are also part of the present invention. In particular, sequences comprising all or part of the following DNA sequence, a complementary DNA or RNA sequence, or a corresponding RNA sequence are especially preferred:

```
                        (nucleotides 240-1172 of SEQ ID NO: 1)
ATGAGACGCGCGGCGCTCTGGCTGTGGCTCTGCGGGCTGGCGCTGCGCCT

GCAGCCTGCCCTCCCGCAAATTGTGGCTGTAAATGTTCCTCCTGAAGATC

AGGATGGCTCTGGGGATGACTCTGACAACTTCTCTGGCTCTGGCACAGGT

GCTTTGCCAGATACTTTGTCACGGCAGACACCTTCCACTTGGAAGGACGT

GTGGCTGTTGACAGCCACGCCCACAGCTCCAGAGCCCACCAGCAGCAACA

CCGAGACTGCTTTTACCTCTGTCCTGCCAGCCGGAGAGAAGCCCGAGGAG

GGAGAGCCTGTGCTCCATGTAGAAGCAGAGCCTGGCTTCACTGCTCCGGA

CAAGGAAAGGAGGTCACCACCAGGCCCAGGGAGACCGTGCAGCTCCCCAT

CACCCAACGGGCCTCAACAGTCAGAGTCACCACAGCCCAGGCAGCTGTCA

CATCTCATCCGCACGGGGCATGCAACCTGGCCTCCATGAGACCTCGGCT

CCCACAGCACCTGGTCAACCTGACCATCAGCCTCCACGTGTGGAGGGTGG

CGGCACTTCTGTCATCAAAGAGGTTGTCGAGGATGGAACTGCCAATCAGC

TTCCCGCAGGAGAGGGCTCTGGAGAACAAGACTTCACCTTTGAAACATCT

GGGGAGAACCAGCTGTGGCTGCCGTAGAGCCCGGCCTGCGGAATCAGCCC

CCGGTGGACGAAGGAGCCCAGGTGCTTCTCAGAGCCTTTTGGACAGGAAG

GAAGTGCTCCCACCTCTCATTGCCGGAGCCTAGTGGGCCTCATCTTTGCT

GTGTGCCTGGTGGCTTTCATGCTGTACCGGATGAAGAGAAGGACGAAGGC

AGCTACTCCTTCCAGGAGCCCAAACAAGCCAATGGCGGTGCCTACAAACC

CACCAAGCAGGAGGAGTTCTACGCC.
```

DNA and RNA molecules containing segments of the larger sequence are also provided for use in carrying out preferred aspects of the invention relating to the production of such peptides by the techniques of genetic engineering and the production of oligonucleotide probes.

BRIEF DESCRIPTION OF THE FIGURES

FIG. 2 is a sequence alignment of a portion of each of the amino acid sequences of homologs of each of syndecan-1, syndecan-2, syndecan-3, and syndecan-4" with human syndecan-1 (amino acids 22–67 of SEQ ID NO:3), rat syndecan-1 (amino acids 22–67 of SEQ ID NO:4), murine syndecan-1 (amino acids 22–66 of SEQ ID NO:2), and hamster syndecan-1 (amino acids 22–67 of SEQ ID NO:5), human syndecan-4 (amino acids 19–63 of SEQ ID NO:6), rat syndecan-4 (SEQ ID NO:7), hamster syndecan-3 (amino acids 44–89 of SEQ ID NO:8), human syndecan-2 (amino acids 11–53 of SEQ ID NO:9), rat syndecan-2 (SEQ ID NO:10), murine syndecan-2 (SEQ ID NO:11), and Fr syndecan-2 (SEQ ID NO:12).

FIG. 3 is a sequence alignment of murine syndecan-1 (SEQ ID NO: 2), rat syndecan-1 (SEQ ID NO: 4), hamster syndecan-1 (SEQ ID NO: 5), human syndecan-1 (SEQ ID NO: 3).

FIG. 4 is a table of exemplary heparin and heparan sulfate binding interactions with biologically significant molecules.

Figure 1:
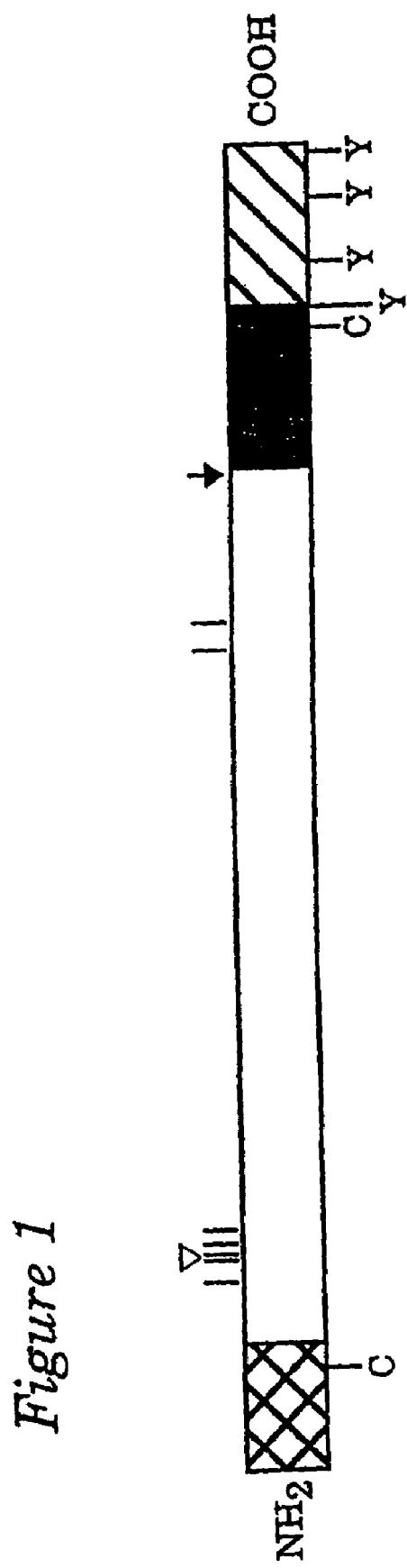
FIG. 1 is a schematic diagram showing different regions of the syndecan core protein.

The accompanying Figures are provided to illustrate the invention but are not considered to be limiting thereof unless so specified.

DETAILED DESCRIPTION OF THE INVENTION

Using a library from mouse mammary epithelial cells, full length cDNAs for a cell surface proteoglycan, herein termed "syndecan-1", have been molecularly cloned and sequenced, and the expression of its mRNA in various tissues has been assessed. The 311 amino acid core protein has a unique sequence that contains several structural features consistent with its role as an acceptor of two distinct types of glycosaminoglycan chains, and as a molecule that binds components of the extracellular space. The expression of its mRNA is shown to be tissue-type specific. The core protein of syndecan-1 defines a new class of cell surface receptor, an integral membrane proteoglycan, for which we derive the name syndecan (from the Greek, syndein, to bind together).

Using this information a variety of recombinant DNA vectors are provided which are capable of providing, in reasonable quantities, syndecan-1, and soluble, heparan sulfate-containing fragments derived from the extracellular domain. Additional recombinant DNA vectors of related structure that code for proteins comprising key structural features identified herein, such as functional heparan sulfate attachment sequences, can be produced from or identified with the syndecan-1 DNA using standard techniques of recombinant DNA technology. Likewise, proteins of the same family from other sources can also be identified with the syndecan-1 DNA and corresponding protein described herein. Transformants expressing syndecan-1 or homologs thereof have been produced as an example of this technology. The newly discovered sequence and structural information can be used, through transfection of eukaryotic cells, to prepare proteoglycans having cleavage sequences and attachment sites that allow production of pure proteoglycans and glycosaminoglycans, as well as fusion proteins which include heparan sulfate and/or chondroitin sulfate glycosaminoglycan (GAG) chains.

Since there is a known and definite correspondence between amino acids in a peptide and the DNA sequence that codes for the peptide, the DNA sequence of a DNA or RNA molecule coding for syndecan-1 (or any of the modified peptides later discussed) can be use to derive the amino acid sequence, and vice versa. Such a sequence of nucleotides encoding a syndecan-1 protein is shown in SEQ. ID NO: 1, along with the corresponding amino acid sequence (shown also in SEQ. ID NO: 2). Complementary trinucleotide DNA sequences having opposite strand polarity are functionally equivalent to the codons of SEQ. ID NO: 1, as is understood in the art. An important and well known feature of the genetic code is its redundancy, whereby, for most of the amino acids used to make proteins, more than one coding nucleotide triplet may be employed. Therefore, a number of different nucleotide sequences may code for a given amino acid sequence. Such nucleotide sequences are considered functionally equivalent since they can result in the production of the same amino acid sequence in all-organisms, although certain strains may translate some sequences more efficiently than they do others. Occasionally, a methylated variant of a purine or pyrimidine may be found in a given nucleotide sequence. Such methylations do not affect the coding relationship in any way. The equivalent codons are shown in Table I below.

TABLE I

GENETIC CODE

| | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

Key: Each 3-letter triplet represents a trinucleotide of DNA having a 5' end on the left and a 3' end on the right. The letters stand for the purine or pyrimidine bases forming the nucleotide sequence. A=adenine, G=guanine, C=cytosine, T=thymine Since the DNA sequence of the coding region of the gene has been fully identified, it is possible to produce a nucleic acid encoding a syndecan, or portion thereof, entirely by synthetic chemistry, after which the gene can be inserted into any of the many available DNA vectors using known techniques of recombinant DNA technology. Thus the present invention can be carried out using reagents, plasmids, microorganism, and eukaryotic cells which are freely and readily available.

Various methods of chemically synthesizing polydeoxynucleotides are known, including solid-phase synthesis which, like peptide synthesis, has been fully automated in commercially available DNA synthesizers (See the Itakura et al. U.S. Pat. No. 4,598,049; the Caruthers et al. U.S. Pat. No. 4,458,066; and the Itakura U.S. Pat. Nos. 4,401,796 and 4,373,071). For example, nucleotide sequences greater than 100 bases long could be readily synthesized in 1984 on an Applied Biosystems Model 380A DNA Synthesizer as evidenced by commercial advertising of the same (e.g., Genetic Engineering News, November/December 1984, p. 3). Such oligonucleotides can readily be spliced using, among others, the techniques described later in this application to produce any nucleotide sequence described herein. For example, relatively short complementary oligonucleotide sequences with 3' or 5' segments that extend beyond the complementary sequences can be synthesized. By producing a series of such short segments, with "sticky" ends that hybridize with the next short oligonucleotide, sequential oligonucleotides can be joined together by the use of ligases to produce a longer oligonucleotide that is beyond the reach of direct synthesis.

Furthermore, automated equipment is also available that makes direct synthesis of any of the peptides disclosed herein readily available. In the same issue of Genetic Engineering News mentioned above, a commercially available automated peptide synthesizer having a coupling efficiency exceeding 99% is advertised (at page 34). Such equipment provides ready access to the peptides of the invention, either by direct synthesis or by synthesis of a series of fragments that can be coupled using other known techniques.

In addition to the specific peptide sequence shown in Seq. ID No. 1, other peptides based on this sequence and representing variations thereof can have similar biological activities of syndecan-1. In particular, proteins that lack the amino terminal signal sequence, as the mature syndecan-1 does, can be useful and are ultimately preferred. Other variations can also be present. For example, truncation mutants can be generated, as described below, which retain the ability to serve as a core protein for attachment of heparan sulfate and chondroitin sulfate glycosaminoglycans (GAGs) and, where required, retain amino acids which might add to the binding ability of the heparan sulfate chains. Likewise, additional exogenous amino acids can be present at either or both terminal ends of the syndecan core protein or its truncations. As described below, these added sequences can, for example, facilitate purification, or be used for in the generation of fusion proteins having novel activities.

Within the portion of the molecule containing the heparan sulfate attachment sequences, replacement of amino acids is more restricted in order that biological activity can be maintained particularly with regard to the attachment of GAGs, in particular, heparan sulfate. However, variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5)

amide=asparagine, glutamine; and (6) sulfur-containing=cysteine and methoinine. (see, for example, *Biochemistry*, 2nd ed, Ed. by L. Stryer, WH Freeman and Co.:1981). Whether a change in the amino acid sequence of a peptide results in a functional heparan sulfate attachment sequence can readily be determined by assessing the ability of the corresponding DNA encoding the peptide to produce this peptide in a form containing a glycosaminoglycan chain when expressed by eukaryotic cells. Examples of this process are described later in detail. If attachment of glycosaminoglycan chains occurs, the replacement is immaterial, and the molecule being tested is equivalent to those specifically described above. Peptides in which more than one replacement has taken place can readily be tested in the same manner.

DNA molecules that code for such peptides can easily be determined from the list of codons in Table I and are likewise contemplated as being equivalent to the DNA sequence of SEQ. ID NO: 1. In fact, since there is a fixed relationship between DNA codons and amino acids in a peptide, any discussion in this application of a replacement or other change in a peptide is equally applicable to the corresponding DNA sequence or to the DNA molecule, recombinant vector, transformed microorganism, or transfected eukaryotic cells in which the sequence is located (and vice versa). Codons can be chosen for use in a particular host organism in accordance with the frequency with which a particular codon is utilized by that host, if desired, to increase the rate at which expression of the peptide occurs.

In addition to the specific nucleotides given in SEQ. ID NO: 1 and truncation's thereof DNA (or corresponding RNA) molecules of the invention can have additional nucleotides preceding or following those that are specifically listed. For example, a poly-adenylation signal sequence can be added to the 3'-terminus, nucleotide sequences corresponding to a restriction endonuclease sites can be added so as to flank the recombinant gene, and/or a stop codon can be added to terminate translation and produce truncated forms of the proteins. Additionally, DNA molecules containing a promoter region or other transcriptional control elements upstream or downstream of the recombinant gene can be produced. All DNA molecules containing the sequences of the invention will be useful for at least one purpose since all can minimally be fragmented to produce oligonucleotide probes and be used in the isolation of additional DNA from biological sources.

Heparan sulfate-containing peptides of the present invention can be prepared, for the first time, as purified preparations by using a cloned gene as described herein. By "purified", it is meant, when referring to a peptide or DNA or RNA sequence, that the indicated molecule is present in the substantial absence of other biological macromolecules of the same type, such as other proteins (particularly other glycoproteins). The term "purified" as used herein preferably means at least 95% by weight, more preferably at least 99% by weight, and most preferably at least 99.8% by weight, of biological macromolecules of the same type present (but water, buffers, and other small molecules, especially molecules having a molecular weight of less than 1000, can be present). The term "pure" as used herein preferably has the same numerical limits as "purified" immediately above. The term "isolated" as used herein refers to a peptide, DNA, or RNA molecule separated from other peptides, DNAs, or RNAs, respectively, that are present in the natural source of the macromolecule. "Isolated" and "purified" do not encompass either natural materials in their native state or natural materials that have been separated into components (e.g., in an acrylamide gel) but not obtained either as pure substances or as solutions.

Two protein sequences (or peptides derived from them of at least 30 amino acids in length) are homologous (as this term is preferably used in this specification) if they have an alignment score of >5 (in standard deviation units) using the program ALIGN with the mutation data matrix and a gap penalty of 6 (or greater). See Dayhoff, M. O., in *Atlas of Protein Sequence and Structure*, 1972, volume 5, National Biomedical Research Foundation, pp. 101–110, and Supplement 2 to this volume, pp. 1–10. The two sequences (or parts thereof—probably at least 30 amino acids in length) are more preferably homologous if their amino acids are greater than or equal to 50% identical when optimally aligned using the ALIGN program mentioned above. Two DNA sequences (or a DNA and RNA sequence) are homologous if they hybridize to one another using nitrocellulose filter hybridization (one sequence bound to the filter, the other as a $^{32}$P labeled probe) using hybridization conditions of 40–50% formamide, 37°–42° C., 4×SSC and wash conditions (after several room temperature washes with 2×SSC, 0.05% SDS) of stringency equivalent to 37° C. with 1×SSC, 0.05% SDS. The number of preferred hybridization conditions are set forth in the examples that follow.

The phrase "replaced by" or "replacement" as used herein does not necessarily refer to any action that must take place, but rather to the peptide that exists when an indicated "replacement" amino acid is present in the same position as the amino acid indicated to be present in a different formula (e.g., when leucine is present at a particular amino acid position instead of isoleucine).

Salts of any of the macromolecules described herein will naturally occur when such molecules are present in (or isolated from) aqueous solutions of various pHs. All salts of peptides and other macromolecules having the indicated biological activity are considered to be within the scope of the present invention. Examples include alkali, alkaline earth, and other metal salts of carboxylic acid residues, acid addition salts (e.g., HCl) of amino residues, and zwitter ions formed by reactions between carboxylic acid and amino residues within the same molecule.

The invention has specifically contemplated each and every possible variation of peptide or nucleotide that could be made by selecting combinations based on the amino acid and nucleotide sequences disclosed in SEQ. ID. NOs: 1 and 2, and possible conservative amino acid substitutions and the choices of codons listed in Table I and all such variations are to be considered as being specifically disclosed.

I. Cloning of Syndecan-1 and Syndecan Homologs

In an embodiment of the present invention, genetic information encoded as mRNA is obtained from cells, preferably from mammalian sources, and used in the construction of a DNA gene, which is in turn used to produce a peptide of the invention. An initial crude cell suspension is sonicated or otherwise treated to disrupt cell membranes so that a crude cell extract is obtained. Known techniques of biochemistry (e.g., preferential precipitation of proteins) can be used for initial purification if desired. The crude cell extract, or a partially purified RNA portion therefrom, is then treated to further separate the RNA. For example, crude cell extract can be layered on top of a 5 ml cushion of 5.7 M CsCl, 10 mM Tris-HCl, pH 7.5, 1 mM EDTA in a 1 in.×3½ in nitrocellulose tube and centrifuged in an SW27 rotor (Beckman Instruments Corp., Fullerton, Calif.) at 27,000 rpm for 16 hrs at 15° C. After centrifugation, the tube contents are decanted, the tube is drained, and the bottom ½ cm containing the clear RNA pellet is cut off with a razor blade. The pellets are transferred to a flask and dissolved in 20 ml 10 mM Tris-HCl, pH 7.5, 1 mm EDTA, 5% sarcosyl and 5% phenol. The solution is then made 0.1 M in NaCl and shaken with 40 ml of a 1:1 phenol:chloroform mixture. RNA is precipitated from the aqueous phase with ethanol in the presence of 0.2 M Na-acetate pH 5.5 and collected by centrifugation. Any other method of isolating RNA from a cellular source may be used instead of this method. Other mRNA isolation protocols, such as the Chomczynski method (described in U.S. Pat. No. 4,843,155) used in conjunction with, for example, an oligo-dT column, are well known.

Various forms of RNA may be employed such as polyadenylated, crude or partially purified messenger RNA, which may be heterogeneous in sequence and in molecular size. The selectivity of the RNA isolation procedure is enhanced by any method which results in an enrichment of the desired mRNA in the heterodisperse population of mRNA isolated. Any such prepurification method may be employed in preparing a gene of the present invention, provided that the method does not introduce endonucleolytic cleavage of the mRNA.

Prepurification to enrich for desired mRNA sequences may also be carried out using conventional methods for fractionating RNA, after its isolation from the cell. Any technique which does not result in degradation of the RNA may be employed. The techniques of preparative sedimentation in a sucrose gradient and gel electrophoresis are especially suitable.

The mRNA must be isolated from the source cells under conditions which preclude degradation of the mRNA. The action of RNase enzymes is particularly to be avoided because these enzymes are capable of hydrolytic cleavage of the RNA nucleotide sequence. A suitable method for inhibiting RNase during extraction from cells involves the use of 4 M guanidium thiocyanate and 1 M mercaptoethanol during the cell disruption step. In addition, a low temperature and a pH near 5.0 are helpful ia further reducing RNase degradation of the isolated RNA.

Generally, mRNA is prepared essentially free of contaminating protein, DNA, polysaccharides and lipids. Standard methods are well known in the art for accomplishing such purification. RNA thus isolated contains non-messenger as well as messenger RNA. A convenient method for separating the mRNA of eukaryotes is chromatography on columns of oligo-dT cellulose, or other oligonucleotide-substituted column material such as polynu or poly-T Sepharose, taking advantage of the hydrogen bonding specificity conferred by the presence of polyadenylic acid on the 3' end of eukaryotic mRNA. Hybridization with oligonucleotide probes prepared from DNA sequences set forth in this specification can then be used to isolate the particularly desired mRNA.

The next step in most methods is the formation of DNA complementary to the isolated heterogeneous sequences of mRNA. The enzyme of choice for this reaction is reverse transcriptase, although in principle any enzyme capable of forming a faithful complementary DNA copy of the mRNA template could be used. The reaction may be carried out under conditions described in the prior art, using mRNA as a template and a mixture of the four deoxynucleoside triphosphates, dATP, dGTP, dCTP, and dTTP, as precursors for the DNA strand. It is convenient to provide that one of the deoxynucleoside triphosphates be labeled with a radio-isotope, for example $^{32}P$ in the alpha position, in order to monitor the course of the reaction, to provide a tag for recovering the product after separation procedures such as chromatography and electrophoresis, and for the purpose of making quantitative estimates of recovery.

The cDNA transcripts produced by the reverse transcriptase reaction are somewhat heterogeneous with respect to sequences at the 5' end and the 3' end due to variations in the initiation and termination points of individual transcripts, relative to the mRNA template. The variability at the 5' end is thought to be due to the fact that the oligo-dT primer used to initiate synthesis is capable of binding at a variety of loci along the polyadenylated region of the mRNA. Synthesis of the cDNA transcript begins at an indeterminate point in the poly-A region, and variable length of poly-A region is transcribed depending on the initial binding site of the oligo-dT primer. It is possible to avoid this indeterminacy by the use of a primer containing, in addition to an oligo-dT tract, one or two nucleotides of the RNA sequence itself, thereby producing a primer which will have a preferred and defined binding site for initiating the transcription reaction.

The indeterminacy at the 3'-end of the cDNA transcript is due to a variety of factors affecting the reverse transcriptase reaction, and to the possibility of partial degradation of the RNA template. The isolation of specific cDNA transcripts of maximal length is greatly facilitated if conditions for the reverse transcriptase reaction are chosen which not only favor full length synthesis but also repress the synthesis of small DNA chains. Preferred reaction conditions for avian myeloblastosis virus reverse transcriptase are given in the examples section of U.S. Pat. No. 4,363,877 and are herein incorporated by reference. The specific parameters which may be varied to provide maximal production of long-chain DNA transcripts of high fidelity are reaction temperature, salt concentration, amount of enzyme, concentration of primer relative to template, and reaction time.

The conditions of temperature and salt concentration are chosen so as to optimize specific base-pairing between the oligo-dT primer and the polyadenylated portion of the RNA template. Under properly chosen conditions, the primer will be able to bind at the polyadenylated region of the RNA template, but non-specific initiation due to primer binding at other locations on the template, such as short, A-rich sequences, will be substantially prevented. The effects of temperature and salt are interdependent. Higher temperatures and low salt concentrations decrease the stability of specific base-pairing interactions. The reaction time is kept as short as possible, in order to prevent non-specific initiations and to minimize the opportunity for degradation. Reaction times are interrelated with temperature, lower temperatures requiring longer reaction times. At 42° C., reactions ranging from 1 min. to 10 minutes are suitable. The primer should be present in 50 to 500-fold molar excess over the RNA template and the enzyme should be present in similar molar excess over the RNA template. The use of excess enzyme and primer enhances initiation and cDNA chain growth so that long-chain cDNA transcripts are produced efficiently within the confines of the short incubation times.

In many cases, it will be possible to further purify the cDNA using single-stranded cDNA sequences transcribed from mRNA. However, as discussed below, there may be instances in which the desired restriction enzyme is one which acts only on double-stranded DNA. In these cases, the cDNA prepared as described above may be used as a template for the synthesis of double stranded DNA, using a DNA polymerase such as reverse transcriptase and a nuclease capable of hydrolyzing single-stranded DNA. Methods for preparing double stranded DNA in this manner have been described in the prior art. See, for example, Ullrich, A., Shine, J., Chirgwin, J. Pictet, R., Tischer, E., Rutter, W. J. and Goodman, R. M., *Science* (1977) 196:1313. If desired, the cDNA can be purified further by the process of U.S. Pat. No. 4,363,877, although this is not essential. In this method, heterogeneous cDNA, prepared by transcription of heterogeneous mRNA sequences, is treated with one or two restriction endonucleases. The choice of endonuclease to be used depends in the first instance upon a prior determination that recognition sites for the enzyme exist in the sequence of the cDNA to be isolated. The method depends upon the existence of two such sites. If the sites are identical, a single enzyme will be sufficient. The desired sequence will be cleaved at both sites, eliminating size heterogeneity as far as the desired cDNA sequence is concerned, and creating a population of molecules, termed fragments, containing the desired sequence and homogeneous in length. If the restriction sites are different, two enzymes will be required in order to produce the desired homogeneous length fragments.

The choice of restriction enzyme(s) capable of producing an optimal length nucleotide sequence fragment coding for all or part of the desired protein must be made empirically. If the amino acid sequence of the desired protein is known, it is possible to compare the nucleotide sequence of uniform length nucleotide fragments produced by restriction endonuclease cleavage with the amino acid sequence for which it codes, using the known relationship of the genetic code common to all forms of life. A complete amino acid sequence for the desired protein is not necessary, however, since a reasonably accurate identification may be made on the basis of a partial sequence. Where the amino acid sequence of the desired protein is now known, the uniform length polynucleotides produced by restriction endonuclease cleavage may be used as probes capable of identifying the synthesis of the desired protein in an appropriate in vitro protein synthesizing system. Alternatively, the mRNA may be purified by affinity chromatography. Other techniques which may be suggested to those skilled in the art will be appropriate for this purpose.

The number of restriction enzymes suitable for use depends upon whether single-stranded or double-stranded cDNA is used. The preferred enzymes are those capable of acting on single-stranded DNA, which is the immediate reaction product of mRNA reverse transcription. The number of restriction enzymes now known to be capable of acting on single-stranded DNA is limited. The enzymes HaeIII, HhaI and Hin(f)I are presently known to be suitable. In addition, the enzyme MboII may act on single-stranded DNA. Where further study reveals that other restriction enzymes can act on single-stranded DNA, such other enzymes may appropriately be included in the list of preferred enzymes. Additional suitable enzymes include those specified for double-stranded cDNA. Such enzymes are not preferred since additional reactions are required in order to produce double-stranded cDNA, providing increased opportunities for the loss of longer sequences and for other losses due to incomplete recovery. The use of double-stranded cDNA presents the additional technical disadvantages that subsequent sequence analysis is more complex and laborious. For these reasons, single-stranded cDNA is preferred, but the use of double-stranded DNA is feasible. In fact, the present invention was initially reduced to practice using double-stranded cDNA.

The cDNA prepared for restriction endonuclease treatment may be radioactively labeled so that it may be detected after subsequent separation steps. A preferred technique is to incorporate a radioactive label such as $^{32}P$ in the alpha position of one of the four deoxynucleoside triphosphate precursors. Highest activity is obtained when the concentration of radioactive precursor is high relative to the concentration of the non-radioactive form. However, the total concentration of any deoxynucleoside triphosphate should be greater than 30 uM, in order to maximize the length of cDNA obtained in the reverse transcriptase reaction. See Efstratiadis, A., Maniatis, T., Kafatos, F. C., Jeffrey, A., and Vournakis, J. N., *Cell*, (1975) 4:367. For the purpose of determining the nucleotide sequence of cDNA, the 5' ends may be conveniently labeled with $^{32}P$ in a reaction catalyzed by the enzyme polynucleotide kinase. See Maxam, A. M. and Gilbert, W., *Proc. Natl. Acad. Sci. USA* (1977) 74:560.

Fragments which have been produced by the action of a restriction enzyme or combination of two restriction enzymes may be separated from each other and from heterodisperse sequences lacking recognition sites by any appropriate technique capable of separating polynucleotides on the basis of differences in length. Such methods include a variety of electrophoretic techniques and sedimentation techniques using an ultracentrifuge. Gel electrophoresis is preferred because it provides the best resolution on the basis of polynucleotide length. In addition, the method readily permits quantitative recovery of separated materials. Convenient gel electrophoresis methods have been described by Dingman, C. W., and Peacock, A. C., *Biochemistry* (1968) 7:659, and by Maniatis, T., Jeffrey, A. and van de Sande, H., *Biochemistry* (1975) 14:3787.

Prior to restriction endonuclease treatment, cDNA transcripts obtained from most sources will be found to be heterodisperse in length. By the action of a properly chosen restriction endonuclease, or pair of endonucleases, polynucleotide chains containing the desired sequence will be cleaved at the respective restriction sites to yield polynucleotide fragments of uniform length. Upon gel electrophoresis, these will be observed to form a distinct band. Depending on the presence or absence of restriction sites on other sequences, other discrete bands may be formed as well, which will most likely be of different length than that of the desired sequence. Therefore, as a consequence of restriction endonuclease action, the gel electrophoresis pattern will reveal the appearance of one or more discrete bands, while the remainder of the cDNA will continue to be heterodisperse. In the case where the desired cDNA sequence comprises the major polynucleotide species present, the electrophoresis pattern will reveal that most of the cDNA is present in the discrete band.

Although it is unlikely that two different sequences will be cleaved by restriction enzymes to yield fragments of essentially similar length, a method for determining the purity of the defined length fragments is desirable. Sequence analysis of the electrophoresis band may be used to detect impurities representing 10% or more of the material in the band. A method for detecting lower levels of impurities has been developed founded upon the same general principles applied in the initial isolation method. The method requires that the desired nucleotide sequence fragment contain a recognition site for a restriction endonuclease not employed in the initial isolation. Treatment of polynucleotide material, eluted from a gel electrophoresis band, with a restriction endonuclease capable of acting internally upon the desired sequence will result in cleavage of the desired sequence into two sub-fragments, most probably of unequal length. These sub-fragments upon electrophoresis will form two discrete bands at positions corresponding to their respective lengths, the sum of which will equal the length of the polynucleotide prior to cleavage. Contaminants in the original band that are not susceptible to the restriction enzyme may be expected to migrate to the original position. Contaminants containing one or more recognition sites for the enzyme may be expected to yield two or more sub-fragments. Since the distribution of recognition sites is believed to be essentially random, the probability that a contaminant will also yield sub-fragments of the same size as those of the fragment of desired sequence is extremely low. The amount of material present in any band of radioactively labeled polynucleotide can be determined by quantitative measurement of the amount of radioactivity present in each band, or by any other appropriate method. A quantitative measure of the purity of the fragments of desired sequence can be obtained by comparing the relative amounts of material present in those bands representing sub-fragments of the desired sequence with the total amount of material.

Following the foregoing separation or any other technique that isolates the desired gene, the sequence may be reconstituted. The enzyme DNA ligase, which catalyzes the end-to-end joining of DNA fragments, may be employed for this purpose. The gel electrophoresis bands representing the sub-fragments of the desired sequence may be separately eluted and combined in the presence of DNA ligase, under the appropriate conditions. See Sgaramella, V., Van de Sande, J. H., and Khorana, H. G., *Proc. Natl. Acad. Sci. USA* (1970) 67:1468. Where the sequences to be joined are not blunt-ended, the ligase obtained from *E. coli* may be used; Modrich, P., and Lehman, I. R., *J. Biol., Chem.* (1970) 245:3626.

The efficiency of reconstituting the original sequence from sub-fragments produced by restriction endonuclease treatment will be greatly enhanced by the use of a method for preventing reconstitution in improper sequence. This unwanted result is prevented by treatment of the homogeneous length cDNA fragment of desired sequence with an agent capable of removing the 5'-terminal phosphate groups on the cDNA prior to cleavage of the homogeneous cDNA with a restriction endonuclease. The enzyme alkaline phosphatase is preferred. The 5'-terminal phosphate groups are a structural prerequisite for the subsequent joining action of DNA ligase used for reconstituting the cleaved sub-fragments. Therefore, ends which lack a 5'-terminal phosphate cannot be covalently joined. The DNA sub-fragments can only be joined at the ends containing a 5'-phosphate generated by the restriction endonuclease cleavage performed on the isolated DNA fragment.

The majority of cDNA transcripts, under the conditions described above, are derived from the mRNA region containing the 5'-end of the mRNA template by specifically priming on the same template with a fragment obtained by restriction endonuclease cleavage. In this way, the above-described method may be used to obtain not only fragments of specific nucleotide sequence related to a desired protein, but also the entire nucleotide sequence coding for the protein of interest. Double-stranded, chemically synthesized oligonucleotide linkers, containing the recognition sequence for a restriction endonuclease, may be attached to the ends of the isolated cDNA, to facilitate subsequent enzymatic removal of the gene portion from the vector DNA. See Scheller et al., *Science* (1977) 196:177. The vector DNA is converted from a continuous loop to a linear form by treatment with an appropriate restriction endonuclease. The ends thereby formed are treated with alkaline phosphatase to remove 5'-phosphate end groups so that the vector DNA may not reform a continuous loop in a DNA ligase reaction without first incorporating a segment of the syndecan-1 DNA. The cDNA, with attached linker oligonucleotides, and the treated vector DNA are mixed together with a DNA ligase enzyme, to join the cDNA to the vector DNA, forming a continuous loop of recombinant vector DNA, having the cDNA incorporated therein. Where a plasmid vector is used, usually the closed loop will be the only form able to transform a bacterium. Transformation, as is understood in the art and used herein, is the term used to denote the process whereby a microorganism incorporates extracellular DNA and reproduces it stably from generation to generation. Plasmid DNA in the form of a closed loop may be so incorporated under appropriate environmental conditions. The incorporated closed loop plasmid undergoes replication in the transformed cell, and the replicated copies are distributed to progeny cells when cell division occurs. As a result, a new cell line is established, containing the plasmid and carrying the genetic determinants thereof. Transformation by a plasmid in this manner, where the plasmid genes are maintained in the cell line by plasmid replication, occurs at high frequency when the transforming plasmid DNA is in closed loop form, and does not or rarely occurs if linear plasmid DNA is used. Once a recombinant vector has been made, transformation of a suitable microorganism is a straightforward process, and novel microorganism strains containing the syndecan-1 gene or a related gene may readily be isolated, using appropriate selection techniques as is understood in the art.

II. Structure of Syndecan-1

A. Core Protein Structure

Using these general techniques specifically as set forth in the following examples, cDNA clones have been isolated which encode the syndecan-1 polypeptide from a normal mouse mammary gland epithelial cell line as well as mouse liver tissue. The nascent polypeptide sequence is 311 amino acids and has a molecular mass of 32,868 daltons. Treatment of syndecan-1 with heparitinase I and chondroitinase ABC generates a protein with relative mobility of ca. 69 k daltons versus globular molecular weight markers on a gradient SDS-PAGE system. Treatment of the ectodomain with anhydrous HF for 1.5 hrs at 0° C., Mort, A. J. and Lamport, D. T. A., *Anal. Biochem.* (1977) 82: 289–309, yields a protein that migrates as a broad band at ca. 46 k daltons, Weitzhandler, M., Streeter, H. B., Henzel, W. J., and Bernfield, M., *J. Biol. Chem.* (1988) 263: 6949–6952. These core protein sizes as measured by SDS-PAGE are larger than would be predicted based on the cDNA and any incompletely removed carbohydrate.

This anomaly appears to be a charge effect and has been seen in other proteins rich in proline, alanine, and highly charged amino acids. Syndecan-1 is not a disulfide cross-linked dimer. Its migration on SDS-PAGE is unchanged following DTT treatment; its CNBr-cleavage product produces a single signal during amino acid sequencing; and its single cysteine in the predicted mature protein is located in the putative transmembrane domain. It also does not appear to be cross-linked by lysyl oxidase- or transglutaminase-mediated reactions because β-aminoproprionitrile and monodansylcadaverine treatments of NMuMG cells do not change its mobility on SDS-PAGE. Proteins with regions rich in proline, alanine and highly charged amino acids have highly extended conformations and anomalously slow mobilities in SDS-PAGE, Guest, J. R., Lewis, H. M., Graham, L. D., Packman, L. C., and Perham, R. N., *J. Mol. Biol.* (1985) 185: 743–754. These amino acids are abundant in syndecan-1, and a Chou and Fasman secondary structure prediction is consistent with large regions of extended conformation. In vitro translation of synthetic mRNA corresponding to the coding region of syndecan-1 (SacI-HindIII fragment of clone 4-19b) produces a nascent polypeptide of ca. 45 k daltons. Therefore, while we have not excluded the possibility of other post-translational modifications, the bulk of the size difference probably reflects anomalous gel migration on SDS-PAGE. The amino acid sequence derived from the syndecan-1 cDNA shows three functional domains; an extracellular domain and, by inference, transmembrane and cytoplasmic domains.

A number of fine-structure aspects of syndecan-1 can be seen by references to DNA and amino acid sequences. Starting at the indicated ATG (corresponding Met-1 in SEQ ID NO: 1), the syndecan-1 cDNA codes for a protein of 311 amino acids containing two hydrophobic stretches. The derived sequence suggests several domains and structural features; their presumed arrangement is summarized in FIG. 1.

The first hydrophobic stretch consists of 12 amino acids beginning shortly after the presumptive start methionine. Because syndecan-1 is oriented with its N-terminus outside of the plasma membrane, this appears to be a signal sequence. The N-terminus of mature syndecan-1 is blocked, and, therefore, it has not been possible to determine the N-terminus directly. A likely site for signal peptidase cleavage is following Pro-22 (SEQ ID NO: 1) in the predicted sequence. Cleavage at this site would generate an N-terminal glutamine which could readily cyclize forming a pyrrolidone carboxlyl residue and thus a blocked N-terminus, as exists in a number of other eukaryotic proteins.

The second hydrophobic stretch is a sequence near the C-terminus which has characteristics of a transmembrane domain (Val-253 through Tyr-227 of SEQ ID NO: 1). This sequence is a highly hydrophobic stretch of 25 residues, followed immediately by a series of highly charged residues consistent with the stop transfer signals found following most membrane spanning domains. This domain also contains the only cysteine and one of the four tyrosines in the apparent mature protein sequence.

The position of the transmembrane domain defines two hydrophilic domains of the syndecan-1 core protein, an extracellular domain consisting of approximately 230 amino acids (Gln-23 through Glu-252), and a smaller cytoplasmic domain consisting of 34 amino acids (Arg-278 through Ala-331). This orientation with respect to the plasma membrane is confirmed by the reactivity of immune serum directed either against a peptide containing the C-terminal seven amino acids or against the ectodomain of syndecan-1. The anti-C-terminus immune serum recognizes the hydrophobic native form of syndecan-1, but is unreactive with the non-hydrophobic ectodomain. In contrast, the anti-ectodomain immune serum recognizes both forms of the molecule.

The extracellular domain of syndecan-1 is released from NMuMG cell surfaces during cell culture, rapidly in response to cell rounding, as well as by mild trypsin treatment. The extracellular domain of syndecan-1 contains a single dibasic site (Arg-Lys) located near the plasma membrane (amino acid residues Arg-250 and Lys-251) at which cleavage of syndecan-1 from the cell surface undoubtedly occurs. Because the endogenously shed extracellular domain of syndecan-1 is indistinguishable from the trypsin-released form, a cell surface trypsin-like protease has been proposed. Shedding during cell culture is from the apical surface. However, when these cells are released from the substratum, destroying their polarity, the extracellular domain is rapidly shed. These previously known results suggest that a cell surface protease is involved, but the structure of the site was not known. Identification of the putative cleavage site by the present invention will now allow more detailed investigation of this activity and will allow production of modified proteoglycans and other proteins that can be readily cleaved to release their extracellular regions for ready purification.

Syndecan-1 isolated from several sources is a hybrid proteoglycan, containing both chondroitin sulfate and heparan sulfate, both of which may have roles in the biological activity of the intact protein. These chains are known to be linked via a xyloside to serine residues in proteins, Roden, L., *The Biochemistry of Glycoproteins and Proteoglycans* (1980) 267–371 and Dorfman, A., *Cell Biology of Extracellular Matrix* (1981) 115–138. Regulating the elaboration of both chondroitin sulfate and heparan sulfate chains on the same core protein is a significant problem because the initial four saccharides are identical. The synthesis of both types of chains is initiated by a xylosyltransferase that resides in either the endoplasmic reticulum or the Golgi, see Farquhar, M. G., *Ann. Rev. Cell-Biol.* (1985) 1: 447–488, and by three Golgi-localized glycosyltransferases, Geetha-Habib, M., Campbell, S. C., Schwartz, N. B., *J. Biol. Chem.* (1984) 259: 7300–7310. Specific chain elongation subsequently involves the sequential action of an N-acetylgalactosaminyltransferase and a glucuronosyltransferse for chondroitin sulfate, and an N-acetylglucosaminyltransferase and a glucuronosyltransferase for heparan sulfate. This specific chain elongation must involve recognition of unique structural features of the core protein and indicates that distinct peptide sequences might exist at heparan sulfate versus chondroitin sulfate attachment sites.

As described below, analysis of proteins produced from point mutations and truncation mutations of the syndecan-1 gene identify the syndecan heparan sulfate attachment site as the SGSG sequence beginning at Ser-45 of the wild-type protein (SEQ ID NO: 2). Based on sequence alignment (see FIG. 2) of the amino acid sequences surrounding the heparan sulfate attachment sequence of syndecan-1 with other syndecan homologs (designated here as syndecan-2, syndecan-3, and syndecan-4), as well as site-directed point mutations of syndecan-1 (described below), a consensus sequence for attachment of heparan sulfate chains to syndecan-like proteins is identified here as comprising Xac-Z-Ser-Gly-Ser-Gly (SEQ ID NO:44), where Xac represents an amino acid residue having an acidic sidechain, and Z represents 1 to 10 amino acid residues, preferably from 1 to 6 amino acid. Additionally, both sequence homology and mutational analysis suggest further that Z further optimally comprises at least one amino acid residue having an aromatic side chain.

B. Heparan Sulfate Structure

The heparan sulfate chains of proteoglycans typically contain approximately equal amount of N-acetylated and N-sulfated disaccharides, which are arranged in a mainly aggregated manner into distinct structural domains. However, it has been found that the molecular fine structure (particularly, O-sulfation) varies markedly between different cell types and between proteoglycans.

In the experimental studies reported below, variations were defined by studying the structure of heparan sulfate chains on syndecan-1 derived from three distinct cell types: simple epithelial (NMuMG mammary cells), fibroblasts (NIH 3T3 cells) and endothelioid cells (Balb/c 3T3 cells). Disaccharide composition of each of the syndecan isolates was analyzed by depolymerization with polysaccharide lyases and strong anion exchange (SAX) HPLC of disaccharide products. Radiolabeled disaccharide were detected using an in-line radioactivity monitor (Canberra Packard Flo-one A-250). The sizes of intact chains and large oligosaccharides were estimated by Sepharose CL-6S chromatography (1×120 cm, 500 mM NH$_4$ HCO$_3$ 1 4 ml/hr). Initial oligosaccharide mapping was carried out by gel filtration on Bio-Gel p6 columns (1×120 cm, 500 mM NH. HCO$_3$, 4 ml/hr) after treatment with low pH HNC$_2$, heparitinase or heparinase.

The disaccharide composition of the three heparan sulfate species was analyzed by SAX HPLC, and the results of this analysis are summarized in Table IV, and compared to data from skin fibroblast heparan sulfates, a mixture from several proteoglycans.

TABLE IV

DISACCHARIDE COMPOSITION
The data below summarizes the disaccharide composition of the different syndecan HS species. For comparison, data from skin fibroblast HS is also shown.

| Standard No. | Disaccharide Structure | Human skin Fibroblast HS | NMuMG | Syndecan-1 HS NIH | Balb/c |
|---|---|---|---|---|---|
| 1 | UA-GlcNAc | 46.0 | 51.0 | 49.4 | 50.3 |
| 2 | UA-GLcNAc(GS) | 5.4 | 4.8 | 5.3 | 4.1 |
| 7 | UA(2S)-GlcNAc | 1.1 | 2.1 | 1.8 | 2.0 |
| 3 | UA-GlcNSO$_3$ | 27.7 | 23.5 | 26.1 | 27.1 |
| 4 | UA-GlcNSO$_3$(6S) | 2.4 | 2.7 | 3.1 | 1.4 |
| 5 | UA(2S)-GlcNSO$_3$ | 15.4 | 9.9 | 6.4 | 9.1 |
| 6 | UA(2S)-GlcNSO$_3$(6S) | 2.0 | 6.0 | 7.9 | 6.0 |
| Sulphates/100 di | | 75.8 | 73.0 | 75.9 | 72.2 |
| O-sulphates/100 di | | 28.3 | 31.5 | 32.4 | 28.6 |
| N-sulphates/100 di | | 47.5 | 42.1 | 43.5 | 43.6 |
| N/O sulphate ratio | | 1.68 | 1.34 | 1.34 | 1.52 |

As illustrated by Table IV, each heparan sulfate species displays a unique disaccharide profile, the most obvious variation being the level of highly sulfated disaccharides: UA(2S)-GlcNSO$_3$ and UA(2S)-GlcNSO$_3$(6S). All three species show characteristic levels of N-sulfation (approximately 45–48%). In contrast, their O-sulfate content (and N/O sulfate ratio) varied markedly. In addition, all three heparan sulfate species derived from syndecan-1 were more highly O-sulfated than the fibroblast heparan sulfate, which is a mixture of heparan sulfate from several proteoglycan species.

The domain structure of the heparan sulfate chain derived from various cell types was analyzed by Bio Gel P6 oligosaccharide mapping after treatment with low pH base HNO$_2$. Similar mapping was also obtained for each of the heparan sulfate chains derived from the different cell types after treatment with heparitinase or heparinase. Based on the P6 mapping data, the distribution of specific linkage types was deteremined (i.e., contiguous, alternating or spaced apart), and is summarized in Table V.

TABLE V

DISTRIBUTION OF DISACCHARIDES
The data below summarizes the distribution of specific disaccharide types. It is based on calculations from Bio-Gel P6 mapping profiles generated with the specific cleavage reagents shown.

| | | NMuMG | NIH | Balb/c |
|---|---|---|---|---|
| N-sulphated disaccharides (HNO$_2$-susceptible) | | 50.0 | 48.4 | 47.9 |
| Distribution* | C | 55 | 52 | 45 |
| | A | 25 | 36 | 33 |
| | S | 20 | 12 | 22 |
| GlcA-containing disaccharides (heparitinase-susceptible) | | 61.0 | 68.7 | 74.3 |
| | C | 76 | 81 | 84 |
| | A | 8 | 6 | 7 |
| | S | 16 | 13 | 9 |
| IdoA(2S)-containing disaccharides (heparinase-susceptible) | | 15.9 | 12.0 | 16.4 |
| | C | 38 | 42 | 56 |
| | A | 19 | 13 | 14 |
| | S | 43 | 45 | 30 |

*Distribution:
C = proportion of linkage in contiguous sequences
A = proportion in alternating sequence with a resistant linkage
S = proportion spaced apart by the two or more resistant linkages The size of the intact chains and large heparitinase-resistant oligosaccharides was estimated by sepharose CL-6S chromatography, as shown below in Table VI.

TABLE VI

SIZE OF HS CHAINS AND HEPARINASE-RESISTANT DOMAINS

| | NMuMG | NIH | Balb/c |
|---|---|---|---|
| Intact chain size (kDa) | 35 | 52 | 75 |
| Average heparinase-resistent domain size* (kDa) | 9 | 8 | 14 |
| (Approximate size range) | (7–15) | (6–14) | (11–19) |

*These domains are the large heparinase-resistant oligosaccharides obtained in the Vo from Bio-Cel P6 profiles.

As can be seen above, the P6 mapping profiles (shown in Table V) indicate significant differences in the content and distribution of GlcA residues (heparitinase susceptible) and IdoA(2S) residues (heparinase susceptible). The mapping profiles for N-sulfated disaccharides were broadly similar in characteristics of cell-derived heparan sulfate. Nonetheless, the three species of heparan sulfate chains varied markedly in size (as shown in Table VI). The average spacing of heparitinase cleavage sites (clustered within N-sulfated domains) also differed between the heparan sulfate species (Table VI).

Based on the foregoing, it should be clear that specific heparan sulfate chains can be readily derived from syndecan-1 from different cell types, particularly from syndecans, and that such cell-type specific heparan sulfate chains or portions thereof can be used for various therapeutic and diagnostic purposes.

III. Expression of Recombinant Syndecans and Syndecan Homologs

A nucleic acid derived from the cloning of syndecan-1, encoding all or a selected portion of the protein, can be used to produce recombinant forms of syndecan by microbial or eukaryotic cellular processes. Syndecan-1, or a molecule containing the functional heparan sulfate attachment sequence of the present invention, can be produced with attached heparan sulfate chains when the DNA sequence encoding it is functionally inserted into a vector that is expressed in a eukaryotic cell containing an enzyme system capable of producing heparan sulfate glycosaminoglycan chains such as the mammailian CHO (ATCC CCL61), COS-7 (ATCC CRL 1651), and NMuMG (ATCC CRL 1637) cells. By "functionally inserted" it is meant that the recombinant gene is under proper transcriptional control, and where necessary, in proper reading frame and orientation, as is well understood by those skilled in the art. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or obvious modifications thereof, can be employed to prepare recombinant syndecan, portions thereof, or fusion proteins thereof, by microbial means or tissue-culture technology in accord with the subject invention.

The recombinant syndecan protein can be produced by ligating the cloned gene, or a portion thereof, into a vector suitable for expression in either prokaryotic cells, eukaryotic cells, or both. Expression vehicles for production of recombinant syndecan include plasmids and other vectors. For instance, suitable vectors for the expression of syndecan include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see for example Broach et al. (1983) in *Experimental Manipulation of Gene Expression*, ed M. Inouye Academic Press, p. 83+). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pHβ APr-1-neo, EBO-pcD-XN, pcDNAI/amp, pcDNAI/neo, pRc/CMV, pSV2gpt, pSV2neo, pSV2-dhfr, pTk2, pRSV-neo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic, as well as general recombinant procedures. See *Molecular Cloning A Laboratory Manual*, 2nd Ed., ed. by Sambrook, Fritsch and Maniatis (Cold Spring Harbor Laboratory Press: 1989) Chapters 16 and 17. Expression of syndecan-1 can be enhanced by including multiple copies of the syndecan-1 gene in a transformed or transfected host, by selecting a vector known to reproduce in the host (i.e. multi-copy plasmids), thereby producing large quantities of protein from exogenous inserted DNA, or by any other known means of enhancing peptide expression.

In some instances, it may be desirable to express the recombinant syndecan by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In preferred embodiments, the expression vectors used to produce the recombinant proteins of the present invention are chosen to include at least one selectable marker for each cell line in which the vector is to be replicated or expressed. For instance, the vectors can be derived with sequences conferring resistance to ampicillin, chloramphenicol or kanomycin to facilitate amplification in E. coli. For selection in mammalian cells, such markers as the mammalian expressible E. coli ecogpt gene—which codes for a xanthine-guanine phosphoribosyl transferase (XGPRT) and allows selection of transfected $HPRT_{13}$ mammalian cells with mycophenolic acid—can be utilized.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasaid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

Manipulation of the expression vectors in some cases will produce constructs which improve the expression of the polypeptide in eukaryotic cells or express syndecan-1 in other hosts. Furthermore, by using the syndecan-1 cDNA, or a fragment thereof, as a hybridization probe, structurally related genes found in other organisms can be easily cloned. These genes include those that code for related core proteins of proteoglycans from other species, especially mammals such as humans and other primates.

The recombinantly produced syndecan peptide need not contain any of the remaining structure of the molecules described herein so long as it provides the indicated sequence at a location in the peptide that is available for glycosylation. Such locations can be predicted, such as by using the algorithms developed by Chou and Fasman, or by empirically inserting a DNA sequence encoding this amino acid sequence into a gene and determining that the product functions as a recognition sequence for the attachment of heparan sulfate chains. A simple artificial peptide, for example, might contain multiple copies of the recognition sequence either located directly adjacent to each other or being joined by from one to ten, preferably one to five, amino acids. Another preferred embodiment involves producing a known polypeptide by genetic engineering that has been engineered to contain the attachment site of the invention at a location known to reside on an external surface of the polypeptide.

On the other hand, although sequences from the natural syndecan-1 amino acid sequences adjacent the Xac-Z-Ser-Gly-Ser-Gly (SEQ ID NO: 44) sequence are not required, they may be retained if desired in order to produce a protein or portion of a protein that more closely resembles a syndecan. Accordingly, artificial peptides containing from 1 to 10, 20, 30, or even more naturally adjacent amino acids as shown in (SEQ ID NO: 1), located either C terminal or N terminal or both to the Xac-Z-Ser-Gly-Ser-Gly (SEQ ID NO: 44) sequence, represent other viable embodiments of the invention. Proteins containing such longer sequences can be prepared in the same manner discussed above using corresponding longer DNA sequences encoding the desired region. For example, the portion of syndecan-1 corresponding to exon 2, given by the formula Q-I-V-A-V-N-V-P-P-E-D-Q-D-G-S-G-D-D-S-D-N-F-S-G-S-G-T-G (amino acids 23–50 of SEQ ID NO: 2), contains both the heparan sulfate attachment sequence as well as the chondroitin sulfate attachment sequence. Furthermore, based on the truncation mutants described in Example 9, the recombinant protein might include an amino acid sequence selected from a group consisting of S-S-N-T-E-T-A-F-T-S-V-L-P-A-G-E-K-P-E-E-G-E-P-V-L-H-V-E-A-E-P-G-F-T-A-R-D-K-E-K-E-V-T-T-R-P-R-E-T-V-Q-L-P-I-T-Q-R-A-S-T-V-R-V-T-T-A-Q-A-A-V-T-S-H-P-H-G-G-M-Q-P-G-L-H-E-T-S-A-P-T-A-P-G-Q-P-D-H-Q-P-P-R-V-E-G-G-G-T-S-V-I-K-E-V-V-E-D-G-T-A-N-Q-L-P-A-G-E-G-S-G-E-Q (amino acids 23–210 of SEQ ID NO: 2), or alternatively, can comprise the entire extracellular domain of syndecan-1 (SEQ ID NO: 2), given by the formula Q-I-V-A-V-N-V-P-P-E-D-Q-D-G-S-G-D-D-S-D-N-F-S-G-S-G-T-G-A-L-P-D-T-L-S-R-Q-T-P-S-T-W-K-D-V-W-L-L-T-A-T-P-T-A-P-E-P-T-S-S-N-T-E-T-A-F-T-S-V-L-P-A-G-E-K-P-E-E-G-E-P-V-L-H-V-E-A-E-P-G-F-T-A-R-D-K-E-K-E-V-T-T-R-P-R-E-T-V-Q-L-P-I-T-Q-R-A-S-T-V-R-V-T-T-A-Q-A-A-V-T-S-H-P-H-G-G-M-Q-P-G-L-H-E-T-S-A-P-T-A-P-G-Q-P-D-H-Q-P-P-R-V-E-G-G-G-T-S-V-I-K-E-V-V-E-D-G-T-A-N-Q-L-P-A-G-E-G-S-G-E-Q-D-F-T-F-E-T-S-G-E-N-T-A-V-A-A-V-E-P-G-L-R-N-Q-P-P-V-D-E-G-A-T-G-A-S-Q-S-L-L-D-R (amino acids 23–250 of SEQ ID NO: 2).

The coding sequences for the polypeptide can be incorporated as a part of a fusion gene including a nucleotide sequence encoding a different polypeptide. In addition to the uses of fusion proteins such as those detailed in section VI below, this type of expression system can be useful under conditions where it is desirable to produce an immunogenic fragment of syndecan. For example, the VP6 capsid protein of rotavirus can be used as an immunologic carrier protein for portions of the syndecan polypeptide, either in the monomeric form or in the form of a viral particle. The nucleic acid sequences corresponding to the portion of syndecan to which antibodies are to raised can be incorporated into a fusion gene construct which includes coding sequences for a late vaccinia virus structural protein to produce a set of recombinant viruses expressing fusion proteins comprising a portion of syndecan as part of the virion. It has been demonstrated with the use of immunogenic fusion proteins utilizing the Hepatitis B surface antigen fusion proteins that recombinant Hepatitis B virions can

```
a).Q-I-V-A-V-N-V-P-P-E-D-Q-D-G-S-G-D-D-S-D-N-F-S-G-S-G-T-G-A-L-P-  (amino acids 23-56 of SEQ ID NO: 2)
   D-T-L;

b).Q-I-V-A-V-N-V-P-P-E-D-Q-D-G-S-G-D-D-S-D-N-F-S-G-S-G-T-G-A-L-P-  (amino acids 23-81 of SEQ ID NO: 2)
   D-T-L-S-R-Q-T-P-S-T-W-K-D-V-W-L-L-T-A-T-P-T-A-P-E-P-T-S c).Q-I-V-A-V-N-V-P-P-E-D-Q-D-G-S-G-D-D-S-D-N-F-S-G-S-G-T-G-A-L-P-  (amino acids 23-106 of SEQ ID NO: 2)
   D-T-L-S-R-Q-T-P-S-T-W-K-D-V-W-L-L-T-A-T-P-T-A-P-E-P-T-S-S-N-T-
   E-T-A-F-T-S-V-L-P-A-G-E-K-P-E-E-G-E-P-V-L-H;
and d).Q-I-V-A-V-N-V-P-P-E-D-Q-D-G-S-G-D-D-S-D-N-F-S-G-S-G-T-G-A-L-P-  (amino acids 23-176 of SEQ ID NO: 2)
   D-T-L-S-R-Q-T-P-S-T-W-K-D-V-W-L-L-T-A-T-P-T-A-P-E-P-T-S-S-N-T-
   E-T-A-F-T-S-V-L-P-A-G-E-K-P-E-E-G-E-P-V-L-H-V-E-A-E-P-G-F-T-A-
   R-D-K-E-K-E-V-T-T-R-P-R-E-T-V-Q-L-P-I-T-Q-R-A-S-T-V-R-V-T-T-A-
   Q-A-A-V-T-S-H-P-H-G-G-M-Q-P-G-L-H-E-T-S-A-P-T-A-P-G-Q-P-D-H.
```

The recombinant syndecan protein can comprise the amino acid residues encoded by Exon 2 and Exon 3 of SEQ ID NO: 2, represented by the formula Q-I-V-A-V-N-V-P-P-E-D-Q-D-G-S-G-D-D-S-D-N-F-S-G-S-G-T-G-A-L-P-D-T-L-S-R-Q-T-P-S-T-W-K-D-V-W-L-L-T-A-T-P-T-A-P-E-P-T- be utilized in this role as well. Similarly, chimeric constructs coding for fusion proteins containing a portion of syndecan and the poliovirus capsid protein can be created to enhance immunogenecity of the set of polypeptide antigens (see for example EP Publication No. 0259149; and Reddy et al.

(1992) Virol. 189:423; Evans et al. (1989) *Nature* 339:385; Huang et al. (1988) *J. Virol.* 62:3855; and Schlienger et al. (1992) *J. Virol.* 66:2).

The Multiple Antigen Peptide (MAP) system for peptide-based immunization can also be utilized to raise antibodies to particular core protein sequences, wherein a desired portion of syndecan is obtained directly from organo-chemical synthesis of the peptide onto an oligomeric branching lysine core (see for example Posnett et al. (1988) *JBC* 263:1719 and Nardelli et al. (1992) *J. Immunol.* 148:914). Antigenic determinants of syndecan can also be expressed and presented by bacterial cells. Such peptides will be useful in raising antibodies to core protein sequences of syndecan-1, such as the cytoplasmic domain, which do not display glycosylation.

In addition to utilizing fusion proteins to enhance immunogenecity, it is widely appreciated that fusion proteins can also facilitate the expression of proteins, such as syndecan, by the use of secretory-directing signal peptides (e.g., see Achstetter et al. 1992 *Gene* 110:25). As set out herein, the wild-type syndecan gene contains an N-terminal signal sequence which directs secretion of the extracellular portion of the protein. Other such signal sequences can be substituted and are deemed to be within the scope of this invention.

In another common use of fusion proteins, a fusion gene can be created having additional sequences coding for a polypeptide portion of the fusion protein which will facilitate its purification. For example, a fusion gene coding for a purification leader comprising a poly-(His)/enterokinase cleavage site sequence at the N-terminus or C-terminus of the desired portion of syndecan can allow purification of the expressed syndecan fusion protein by affinity chromatography using a $Ni^{2+}$ metal resin. The purification leader sequence can then be subsequently removed by treatment with enterokinase (e.g., see Hochuli et al. 1987 *J. Chromatography* 411:177; and Janknecht et al. *PNAS* 88:8972).

IV. Analysis of the Heparan Sulfate Attachment Sequence

This invention further provides a method of generating sets of combinatorial mutants of the heparan sulfate attachment sequence of syndecans, and identifying those potential attachment sequence that are functional by scoring for the presence of heparan sulfate GAG chains. The purpose of screening such combinatorial libraries is to generate novel heparan sulfate containing syndecans which can have at least a portion of the normal activity of wild-type syndecans, or alternatively, posses novel activities. For example, novel heparan sulfate attachment sequences (e.g. those not naturally occurring in syndecans) can provide for more efficient attachment of heparan sulfate chains, particularly in the creation of attachment sites amenable to inclusion in fusion proteins, as well as for use in tandem repeats. Moreover, manipulation of the heparan sulfate attachment sequence and flanking sequences, as demonstrated in the examples below, can influence the size and composition of the attached heparan sulfate chain, giving rise to novel heparan sulfate chains having binding characteristics which can be different (including antagonistic) relative to heparan sulfate from naturally occurring syndecans.

Since the molecular cloning of the syndecan-1 core protein from mouse mammary epithelia (U.S. patent application Ser. No. 07/331,585), cDNA-derived amino acid sequences have become available for other syndecan core proteins that are sufficiently similar to indicate common ancestry. These proteins, which constitute the syndecan family, have a similar domain structure, highly conserved sequences, and a conserved exon organization in the genes studied to date. Evolution of the syndecans from a common ancestor appears to have maintained the location and nature of the putative glycasaminoglycan (GAG) attachment sites, the protease susceptible site adjacent to the plasma membrane, and the transmembrane and cytoplasmic domains. Size, GAG attachment sites, and sequences indicate a close structural relationship between the proteins. Where studied, the core proteins of the syndecan family have similar chemical properties. Each is a heparan sulfate containing proteoglycan, and may, in some cases, also include chondroitin sulfate.

In one aspect of this method, the occurrence for each amino acid type is determined at each amino acid position of aligned heparan sulfate attachment sequence from a population of syndecan variants. Such a population of variants can include, for example, naturally occurring syndecans from one or more species, as well as recombinant syndecans which retain functional heparan sulfate attachment sequences. Amino acids which appear at each position of the aligned sequences are selected to create a degenerate set of combinatorial attachment sequences.

In a preferred embodiment, the combinatorial syndecan library is produced by way of a degenerate library of genes encoding a library of polypeptides which each include at least one potential heparan sulfate attachment sequence. A mixture of synthetic oligonucleotides can be enzymatically ligated into gene sequences such that the set of potential syndecans are expressible as individual polypeptides, or as a set of larger fusion proteins containing the set of syndecan heparan sulfate attachment sequences therein.

To analyze the sequences of a population of variants of syndecan heparan sulfate attachment sites, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned. For instance, demonstrated below is the alignment of several heparan sulfate attachment sequences of syndecans-1 through -4 (Table II), wherein the N-terminal acidic amino acid, a conserved aromatic amino acid, and the Ser-Gly-Ser-Gly sequences are aligned relative to the sequence of syndecan-2 (Table III).

The sequences:

TABLE II

| Hu-Syndecan -1 Asp -Asn -Phe -Ser -Gly -Ser -Gly | (Amino acids 42–48 of SEQ ID NO. 3) |
|---|---|
| Rt-Syndecan -1 Asp -Asn -Phe -Ser -Gly -Ser -Gly | (Amino acids 42–48 of SEQ ID NO. 4) |

TABLE II-continued

| | | | | | | | | |
|---|---|---|---|---|---|---|---|---|
| Mu-Syndecan-1 | Asp | -Asn | -Phe | -Ser | -Gly | -Ser | -Gly | (Amino acids 42–48 of SEQ ID NO. 2) |
| Gh-Syndecan-1 | Asp | -Asn | -Phe | -Ser | -Gly | -Ser | -Gly | (Amino acids 42–48 of SEQ ID NO. 5) |
| Hu-Syndecan-4 | Asp | -Asp | -Phe | -Glu | -Leu | -Ser | -Gly -Ser -Gly | (Amino acids 38–46 of SEQ ID NO. 6) |
| Rt-Syndecan-4 | Asp | -Phe | -Glu | -Leu | -Ser | -Gly | -Ser -Gly | (Amino acids 20–27 of SEQ ID NO. 7) |
| Ch-Syndecan-3 | Asp | -Ile | -Tyr | -Ser | -Gly | -Ser | -Gly -Ser -Gly | (Amino acids 64–72 of SEQ ID NO. 8) |
| Hu-Syndecan-2 | Asp | -Asp | -Tyr | -Ala | -Ser | -Ala | -Ser -Gly -Ser -Gly | (Amino acids 31–40 of SEQ ID NO. 9) |
| Rt-Syndecan-2 | Asp | -Asp | -Tyr | -Ser | -Ser | -Ala | -Ser -Gly -Ser -Gly | (Amino acids 21–30 of SEQ ID NO. 10) |
| Mu-Syndecan-2 | Asp | -Asp | -Tyr | -Ser | -Ser | -Ala | -Ser -Gly -Ser -Gly | (Amino acids 21–31 of SEQ ID NO. 11) |
| Fr-Syndecan-2 | Asp | -Asp | -Tyr | -Ser | -Ser | -Gly | -Ser -Gly -Ser -Gly | (Amino acids 16–25 of SEQ ID NO. 12) |
| Dr-Syndecan | Asp | -Pro | -Asp | -Tyr | -Ser | -Gly | -Ser -Gly -Phe -Gly | (SEQ ID NO. 45) |

Where Hu = human, Rt = rat, Mu = mouse, Gh = hamster, Ch = chicken, Dr = Drosophila, and Fr = frog.

TABLE III can be aligned as:

| | | | | | | | | | | | |
|---|---|---|---|---|---|---|---|---|---|---|---|
| Hu-Syndecan-1 | Asp | -Asn- | Phe- | * | * | * | Ser- | Gly- | Ser- | Gly | (Amino acids 42–48 of SEQ ID NO. 3) |
| Rt-Syndecan-1 | Asp | -Asn- | Phe- | * | * | * | Ser- | Gly- | Ser- | Gly | (Amino acids 42–48 of SEQ ID NO. 4) |
| Mu-Syndecan-1 | Asp | -Asn- | Phe- | * | * | * | Ser- | Gly- | Ser- | Gly | (Amino acids 42–48 of SEQ ID NO. 2) |
| Gh-Syndecan-1 | Asp | -Asn- | Phe- | * | * | * | Ser- | Gly- | Ser- | Gly | (Amino acids 42–48 of SEQ ID NO. 5) |
| Hu-Syndecan-4 | Asp | -Asp- | Phe- | Glu- | Leu- | * | Ser- | Gly- | Ser- | Gly | (Amino acids 38–46 of SEQ ID NO. 6) |
| Rt-Syndecan-4 | Asp | * | Phe- | Glu- | Leu- | * | Ser- | Gly- | Ser- | Gly | (Amino acids 20–27 of SEQ ID NO. 7) |
| Ch-Syndecan-3 | Asp | -Ile- | Tyr- | Ser- | Gly- | * | Ser- | Gly- | Ser- | Gly | (Amino acids 64–72 of SEQ ID NO. 8) |
| Hu-Syndecan-2 | Asp | -Asp- | Tyr- | Ala- | Ser- | Ala- | Ser- | Gly- | Ser- | Gly | (Amino acids 31–40 of SEQ ID NO. 9) |
| Rt-Syndecan-2 | Asp | -Asp- | Tyr- | Ser- | Ser- | Ala- | Ser- | Gly- | Ser- | Gly | (Amino acids 21–30 of SEQ ID NO. 10) |
| Mu-Syndecan-2 | Asp | -Asp- | Tyr- | Ser- | Ser- | Ala- | Ser- | Gly- | Ser- | Gly | (Amino acids 21–31 of SEQ ID NO. 11) |
| Fr-Syndecan-2 | Asp | -Asp- | Tyr- | Ser- | Ser- | Gly- | Ser- | Gly- | Ser- | Gly | (Amino acids 16–25 of SEQ ID NO. 12) |
| Dr-Syndecan | Asp | * | Tyr- | * | * | * | Ser- | Gly- | Ser- | Gly | (SEQ ID NO. 45) |

Analysis of the alignment of heparan sulfate attachment sequences as shown in Table III can give rise to the generation of a degenerate library of polypeptides comprising a potential syndecan heparan sulfate attachment sequence represented by the general formula:

Asp-Xaa(1)-Xaa(2)-Xaa(3)-Xaa(4)-Xaa(5)-Ser-Gly-Ser-Gly wherein Xaa(1) is Asn, Asp, Ile or an amino acid gap; Xaa(2) is Phe or Tyr; Xaa(3) is Glu, Ser, Ala or an amino acid gap; Xaa(4) is Leu, Gly, Ser or an amino acid gap; and Xaa(5) is Ala, Gly or an amino acid gap.

In this context, an amino acid gap is understood to mean the deletion of that amino acid position from the polypeptide. For example, where Xaa(1) is Asn, Xaa (2) is Phe, and Xaa (3), Xaa (4), and Xaa(5) are each an amino acid gap, the heparan sulfate attachment sequence would be the Asp-Asn-Phe-Ser-Gly-Ser-Gly (amino acids 4247 of SEQ ID NO: 2) sequence of syndecan-1.

Further expansion of the combinatorial library can be made by, for example, including amino acids which would represent conservative mutations at one or more of the degenerate positions. Inclusion of such conservative mutations can give rise to a library of potential heparan sulfate attachment sequences represented by the formaula:

Xac-Xaa(1)-Xaa(2)-Xaa(3)-Xaa(4)-Xaa(5)-Ser-Gly-Ser-Gly (SEQ ID NO: 14)

wherein Xac is Asp or Glu Xaa(1) is Asn, Gln, Asp, Glu, Gly, Ala, Val, Ile, Leu, Ser, Thr or an amino acid gap; Xaa(2) is Phe, Tyr or amino acid gap and, optionally, Trp, Leu or Ile; Xaa(3) is Asp, Glu, Gly, Ala, Val, Ile, Leu, Ser, Thr or an amino acid gap; Xaa(4) is Gly, Ala, Val, Ile, Leu, Ser, Thr or an amino acid gap; and Xaa(5) is Gly, Ala, Val, Ile, Leu, Ser, Thr or an amino acid gap.

The further degeneracy of Trp at Xaa(2) represents the notion that substitution of the aromatic amino acid sidechains of Phe and Tyr with another aromatic amino acid is a conservative replacement. Likewise, replacement of Phe at Xaa(2) with Leu or Ile would be deemed isosterically conservative from the standpoint that a large hydrophobic sidechain is being replaced with another large hydrophobic sidechain.

In a similar fashion, larger portions of the syndecan homologs can be aligned and used to create combinatorial libraries of potential heparan sulfate attachment sequences. For example, FIG. 3 illustrates the alignment of the mouse, rat, hamster and human homologs of syndecan-1. Combinatorial libraries can be generated based on the sequence of exon2, which comprises Gln-23 through Gly-50. Such degenerate libraries can be represented, for example, by the general formula.

Gln-Ile-Val-Xaa(1)-Xaa(2)-Asn-Xaa(3)-Pro-Pro-Glu-Asp-Gln-Asp-Gly-Ser-Gly-Asp-Asp-   (SEQ ID NO: 15)
Ser-Asp-Asn-Phe-Ser-Gly-Ser-Gly-Xaa(4)-Gly, where Xaa(1) is Gly, Ala, Val, Leu, Ile, an amino acid gap, Cys, Ser or Thr; Xaa(2) is Gly, Ala, Val, Leu, Ile, Cys, Ser or Thr; Xaa(3) is Gly, Ala, Val, Leu, or Ile; and Xaa(4) is Gly, Ala, Val, Leu, Ile, Cys, Ser or Thr.

Likewise, the degeneracy of a larger fragment, such as that corresponding to the mature truncation mutant 70/221 described in Example 9 (sans signal peptide) of Gln-23 through Ser-81, can be calculated and used to generate the combinatorial library of the present invention. Such a degenerate peptide might comprise the sequence > Gln-Ile-Val-Xaa(1)-Xaa(2)-Asn-Xaa(3)-Pro-Pro-Glu-
> Asp-Gln-Asp-Gly-Ser-Gly-Asp-Asp-Ser-Asp-
> Asn-Phe-Ser-Gly-Ser-Gly-Xaa(4)-Gly-Ala-Leu-
> Xaa(6)-Asp-Xaa(7)-Thr-Leu-Ser-Xaa(8)-Gln-
> Xaa(9)-Xaa(10)-Xaa(11)-Thr-Xaa(12)-Lys-Asp-
> Xaa(13)-Xaa(14)-Leu-Leu-Thr-Ala-Xaa(15)-Pro-
> Thr-Xaa(16)-Pro-Glu-Pro-Thr-Xaa(17)   (SEQ ID NO: 16)

where Xaa(1) is Gly, Ala, Val, Leu, Ile, an amino acid gap, Cys, Ser or Thr; Xaa(2) is Gly, Ala, Val, Leu, Ile, Cys, Ser or Thr; Xaa(3) is Gly, Ala, Val, Leu, or Ile; and Xaa(4) is Gly, Ala, Val, Leu, Ile, Cys, Ser or Thr; Xaa(6) is Pro, Gln and Asn; Xaa(7) is Ala, Val, Leu, IRe, Met, or an amino acid gap; Xaa(8) is Arg or Gln; Xaa(9) is Gly, Ala, Val, Leu, Ile, Thr or Ser; Xaa(10) is Pro, Ser or Thr; Xaa(11) is Pro, Ser or Thr; Xaa(12) is Ile, Leu, Phe, Tyr or Trp; Xaa(13) Gly, Ala, Val, Ile, Leu, Ser or Thr; Xaa(14) is Trp, Phe, Tyr, Gln, Asn; Xaa(15) is Ala, Val, Leu, Ile, Thr, or Ser; Xaa(16) is Gly, Ala, Val, Leu, Ile, Ser or Thr; and Xaa(17) is Gly, Ala, Val, Leu, Ile, Thr or Ser.

There are many ways by which the library of potential syndecans can be generated from a degenerate oligonucleotide sequence. Chemical synthesis of a degenerate gene sequence can be carried out in an automatic DNA synthesizer, and the synthetic genes can then be ligated into an appropriate gene for expression. The purpose of a degenerate set of genes is to provide, in one mixture, all of the sequences encoding the desired set of potential heparan sulfate attachment sequences. In general, it will not be practical to synthesize each oligonucleotide of this mixture one by one, particularly in the case of great numbers of possible variants. In these instances, the degenerate nucleic acid can be synthesized by a strategy in which a mixture of coupling units (nucleotide monomers) are added at the appropriate positions in the sequence such that the final oligonucleotide mixture includes the sequences coding for the desired set of potential attachment sites. Conventional techniques of DNA synthesis take advantage of protecting groups on the reactive deoxynucleotides such that, upon incorporation into a growing oligomer, further coupling to that oligomer is inhibited until a subsequent deprotecting step is provided. Thus, to create a degenerate sequence, more than one type of deoxynucleotide can be simultaneously reacted with the growing oligonucleotide during a round of coupling, either by premixing nucleotides or by programming the synthesizer to deliver appropriate volumes of nucleotide-containing reactant solutions. For each codon position corresponding to an amino acid position having only one amino acid type in the eventual set of degenerate syndecans, each oligonucleotide of the degenerate set of oligonucleotides will have an identical nucleotide sequence. At a codon position corresponding to an amino acid position at which more than one amino acid type will occur in the eventual set, the degenerate set of oligonucleotides will comprise nucleotide sequences giving rise to codons which code for those amino acid types at that position in the set. Where the degeneracy at a particular amino acid position includes an amino acid gap, a portion of the oligonucleotide can be held aside (i.e. not reacted with any coupling unites) until the codon triplet has been synthesize for the remaining portion. In some instances, due to other combinations that the degenerate nucleotide sequence can have, the resulting oligonucleotides will have codons directed to amino acid types other than those designed to be present based on analysis of the occurrence in the aligned variants. The synthesis of degenerate oligonucleotides is well known in the art (see for example Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477).

The entire coding sequence for the polypeptide set can be synthesized by this method. In some instances however, it may be desirable to synthesize degenerate oligonucleotide fragments by this method, which are then ligated to invariant DNA sequences generated separately (either by chemical synthesis or manipulation of cDNA) to create the degenerate gene sequence.

Likewise, as demonstrated above, the amino acid positions containing more than one amino acid type in the generated set of polypeptide need not be contiguous in the polypeptide sequence. For instance, it may be desirable to synthesize a number of degenerate oligonucleotide fragments, each fragment corresponding to a distinct fragment of the coding sequence for the combinatorial set of syndecans. Each degenerate oligonucleotide fragment can then be enzymatically ligated to the appropriate invariant DNA sequences coding for stretches of amino acids for which only one amino acid type occurs at each position in the degenerate gene. Thus, the final degenerate coding sequence is created by fusion of both degenerate and invariant sequences.

Furthermore, the degenerate oligonucleotide can be synthesized as degenerate fragments and ligated together (i.e., complementary overhangs can be created, or blunt-end ligation can be used). It is common to synthesize overlapping fragments as complementary strands, then anneal and fill in the remaining single-stranded regions of each strand. It will generally be desirable in instances requiring annealing of complementary strands that the junction be in an area of little degeneracy.

Many techniques are available for identifying functional heparan sulfate and/or attachment sequences which are a part of a syndecan homolog, or, as described below, a portion of a fusion protein. Such techniques can be used to screen the present combinatorial libraries to identify clones which comprise such functional attachment sequences. For instance, ligand-affinity or panning methods for assessing expression of membrane-bound proteins are well established (Aruffo et al. (1987) *PNAS* 84: 8573; Seed et al. (1987) *PNAS* 84:3365; and Kiefer et al. (1990) *PNAS* 87:6985). For example, as described in Example 14, expression vectors encoding a protein comprising a potential heparan sulfate attachment sequence can be used to transfect cells which ordinarily do not bind significantly to basic FGF (bFGF) coated culture dishes. Where the transfectant contains a recombinant gene encoding a functional heparan sulfate attachment sequence, expression of a heparan sulfate chain on the surface of the cell will result in an increased binding of the cell to the culture plate, the bound cells therefore representing a population enriched for functional attachment sequences. Such panning assays can be carried out using any insolubilized substrate which would act to sequester cells displaying heparan sulfate, such as, to illustrate, other heparin binding growth factors such as heparin-binding EGF-like growth factor (HB-EGF), platelet-derived growth factor (PDGF), vascular endothelial growth factor (VEGF), matrix molecules like thrombospondin, fibronectin, entactin, or enzymes like lipoprotein lipase, enzyme inhibitors such as antithrombin III, or other proteins with known affinity for heparin, like apolipoprotein A or protamine. Such assays are amenable to high through-put analysis as necessary to screen large numbers of degenerate heparan sulfate attachment sequences created by combinatorial mutagenesis techniques.

In a similar fashion, fluorescently labeled substrates which bind heparan sulfate chains can be used to score for attachment of heparan sulfate to an engineered amino acid sequence. By way of example, a biologically active fluorescent derivative of bFGF (Healy et al. (1992) *Exp. Eye Res.* 55: 663) can be used to detect heparan sulfate GAG chains expressed on a cell surface. Cells can be visually inspected and separated under a fluorescence microscope, or, where the morphology of the cell permits, separated by a fluorescence—activated cell sorter.

In another embodiment of the present assay, the level of proliferation can be scored using transfected cells which are mitogenically responsive to one or more HBGFs. As described below, heparan sulfate/HBGF interactions are an essential prerequisite for the presentation and subsequent binding of these growth factors to signal transducing receptors. Therefore, only cells transfected with a surface protein comprising a functional heparan sulfate attachment sequence will display an increased proliferation in the presence of a mitogenic HBGF.

In yet another embodiment, the combinatorial library can be expressed as part of a fusion protein with a viral capsid protein which can be expressed in a eukaryotic cell under conditions wherein heparin sulfate chains are attached to functional heparan sulfate sites, and the fusion protein is incorporated into a viral particle. Using detection protocols similar to those used in analysis of phase display libraries (see, for example International Publication Nos. WO92/15679, WO92/18619, and WO92/09690), viral particles comprising heparan sulfate chains can be isolated and the sequence of the functional heparan sulfate attachment site determined.

V. Uses of Syndecans, Homologs thereof and Products Derived therefrom

A. Isolation of Homologs

Particularly contemplated is the isolation of homologs related to syndecan-1 from murine sources from and other organisms that express proteoglycans on their surfaces by using oligonucleotide probes based on the principal and variant nucleotide sequences disclosed herein. Such probes can be considerably shorter than the entire sequence, but should be at least 12, preferably at least 20, nucleotides in length. Longer oligonucleotides are also useful, up to 30, 40, 50, 75, or 100 nucleotides and further up to the full length of the gene. Both RNA and DNA probes can be used. Such probes can also be used in diagnostic tests that detect the presence of genetic material of a predetermined sequence in samples, e.g., as in a polymerase chain reaction (PCR).

In use, the probes are typically labeled in a detectable manner (e.g., with $^{32}$P, $^3$H, biotin, or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known.

Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide" refers to both labeled and unlabeled forms and not just to labeled probes.

Particularly preferred are oligonucleotides corresponding to the segments of the gene that code for glycosaminoglycan attachment sites, such as the heparan sulfate attachment sequence. For example, the oligonucleotide probes GACAACTTCTCTGGCTCTGGC (SEQ ID NO: 17) and GCCAGAGCCAGAGAAGTTGTC (SEQ ID NO: 18), which correspond to the heparan sulfate attachment sequence Asp-Asn-Phe-Ser-Gly-Ser-Gly (amino acids 42–47 of SEQ ID NO: 2), can be used to identify syndecan-1, and closely related homologs thereof, in other tissues and in other species. Similarly, oligonucleotides directed to the chondroitin sulfate attachment sequences, such as those surrounding Ser-37, can have a high probability of success in the identification of other gene products. By way of example, the 64-fold degenerate oligonucleotide of the form GANGGNTCTGGNGA (SEQ ID NO: 19), where N represents presence of all four nucleotides in degenerate sequences. The complementary oligonucleotide having the degenerate sequence can be used to screen cDNA and genomic libraries for syndecan homologs. TCNCCAGANC-CNTC (SEQ ID NO: 20) is also particularly useful and has the added advantage of ability to identify messenger RNA of these gene products in Northern analysis.

Oligonucleotides directed to portions of the syndecan-1 gene encoding the cytoplasmic portion of the molecule may also be useful as probes and/or anti-sense constructs. For example, the oligonucleotides TACCGGATGAAGAA-GAAGGAC is GAAGGCAGCTAC (SEQ ID NO: 21) and ATGGCCTACTTCTTCTTCCTGCTTCC-GTCGATG (SEQ ID NO: 22), which correspond to the amino acid sequence Tyr-Arg-Met-Lys-Lys-Lys-Asp-Glu-Gly-Ser-Tyr (amino acids 277–287 of SEQ ID NO: 2), as well as the oligonucleotides GAGTTCTACGCC (SEQ ID NO: 23), and GGCGTAGAACTC (SEQ ID NO: 24) which correspond to the C-terminal Glu-Phe-Tyr-Ala sequence, can be used diagnostically, therapeutically, or as a reagent for cloning.

B. Production and Use of Ab's

The syndecan-1, portions thereof, and homologs thereof, of the present invention can be used to produce anti-syndecan antibodies using known techniques. Both monoclonal and polyclonal antibodies (Ab) directed against epitopes on syndecan, and antibody fragments such as Fab and F(ab)$_2$, can be used to block the action of the syndecans and allow study of their function.

To illustrate, the effect of anti-syndecan Abs on tissue development can be assessed in vivo, such as in intact embryos. It has been demonstrated that prior to the conversion of the metanephrogenic mesenchyme to kidney tubules, which includes dramatic changes in its extracellular matrix, the mesechymal cells synthesize syndecan-1 (Vaino et al. (1989) Dev. Biol. 134:382). This cell surface proteoglycan is first seen around the mesenchymal cells surrounding the ureteric bud as the bud first enters the region of the mesenchyme. As the ureteric bud initiates it first branch, the mesenchymal region around the branch stains positive for syndecan-1 using specific antibodies described herein. The cell layers immediately adjacent to the ureteric bud stain more intensely. If proteoglycan synthesis is inhibited in embryonic kidney rudiments, mesenchymal cells cease to form the epithelial tubules and the ureter fails to branch when it enters the mesenchymal region.

The use of anti-syndecan Abs during developmental stages of embryos can allow assessment of the effect of syndecan-1 on the formation of particular tissues in vivo. In a similar approach, hybridomas producing anti-syndecan monoclonal Abs, or biodegradable gels in which anti-syndecan Abs are suspended, can be implanted at a site proximal or within the area at which syndecan action is intended to be blocked. Experiments of this nature can aid in deciphering the role of other factors that may be involved in tissue formation. Antibodies which specifically bind syndecan epitopes can also be used in immunohistochemical staining of tissue samples in order to evaluate the abundance and pattern of expression of syndecan and syndecan homologs. Anti-syndecan antibodies can be used diagnostically in immuno-precipitation and immuno-blotting to detect and evaluate syndecan levels in tissue or bodily fluid as part of a clinical testing procedure. For instance, such measurements can be useful in predictive valuations of the onset or progression of hyperplasias, or where there is reason to believe that there is a deficiency in syndecan function. Likewise, the ability to monitor syndecan levels in an individual can allow determination of the efficacy of a given treatment regimen for an individual afflicted with such a disorder. The level of syndecan can be measured in bodily fluid, such as in samples of plasma or serum, or can be measured in tissue, such as produced by biopsy. Diagnostic assays using anti-syndecan antibodies can include immunoassays to aid in early diagnosis of conditions in which changes occur in syndecan blood levels, potentially metastatic carcinoma, chronic inflammation as in hepatic cirrhosis or chromic obstructive pulmonary disease, or recurrence of myeloproliferative disease, as multiple myeloma.

Another application of anti-syndecan antibodies is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of syndecan can then be detected with antibodies, as for example reacting nitrocellulose filters lifted from infected plates with anti-syndecan antibodies. Phage, scored by this assay, can then be isolated from the infected plate. Thus, the presence of syndecan-1 and syndecan-1 homologs can be detected and cloned from other sources.

C. Uses of Recombinant Syndecans and Probes

In addition, the nucleotide probes described above can be used for histological screening of intact tissue and tissue samples for the presence of syndecan mRNA. Similar to the diagnostic uses of anti-syndecan antibodies, the use of probes directed to syndecan mRNA, or to genomic syndecan sequences, can be used for both predictive and therapeutic evaluation of organogenic disorders. Used in conjunction with anti-syndecan antibody immunoassays, the nucleotide probes can help facilitate the determination of the molecular basis for such a disorder which may involve some abnormality associated with syndecan. For instance, variation in syndecan synthesis can be differentiated from a change in syndecan metabolism (such as increased catabolism).

Also, similar to the antibody blocking experiments, the use of anti-sense techniques (e.g. microinjection of antisense molecules, or transfection with plasmids whose transcripts are anti-sense with regard to syndecan mRNA) can be used to study events such as organogenesis in a controlled environment by inhibiting endogenous syndecan production. Such techniques can be utilized in cell culture, but can also be used in the creation of transgenic animals.

In one aspect of the invention, therapeutic agents can be developed which are isolated, or otherwise derived, from cells which contain heparan sulfate chains and which exhibit high affinity for particular ligand (e.g., a metabolite, pathogen or other factor). Such agents can take the form of soluble syndecans having heparan sulfate chains which have been cleaved from selected cells and then purified or, alternatively, synthetic peptides based on native or derivative sequences which have been constructed by genetic engineering techniques. Such soluble agents can be administered to a subject (e.g., a human or animal) in an effective amount to treat a particular disease or metabolic condition, including, for example, promotion of selective wound repair, reduction of tissue-specific inflammation, inhibition of metastasis, reduction of cholesterol levels in blood, inhibition of viral or other pathogenic infections, repair of neuro-muscle junctions, and treatment of leukemia.

As set out in FIG. 4, the binding interactions of heparin and heparan sulfate include association with large, insoluble matrix molecules, including fibronectin, wnt-1, interstital collagens such as types I, III and V, laminin, pleiotropin, tenascin, thrombospondin, and vitronectin. Binding of heparin-like chains to several growth factors has been observed and believed to contribute to, in some instances, increased half-lifes, sequestering of growth factors at the cell surface, and increased biological binding affinities for cell-surface receptors. Such growth factors include: the heparin-binding growth factor (HBGF) family comprising basic fibroblast growth factor (bFGF), acidic FGF (aFGF), Int-2, hst/KGF, and FGF-5; heparin-binding EGF-like growth factor (HB-EGF), platelet-derived growth factor (PDGF), transforming growth factor-β (TGF-β), vascular endothelial growth factor (VEGF), hepatocyte growth factor, interferon γ, and Schwannoma-derived growth factor (SDGF).

Heparin-like molecules are also implicated in the biological activity of protease inhibitors like antithrombin m, heparin cofactor II, leuserpin, plasminogen activator inhibitor, lipoprotein-associated coagulation inhibitor and protein nexin I. Moreover, heparin-like molecules may cause the cell surface association of degradative enzymes such as acetylcholinesterase, extracellular superoxide dismutase, thrombin, and tissue plasminogen activator. Cell adhesion molecules such as N-CAM and PECAM, lipoproteins like apoB and apoE, as well as lipolytic enzymes including cholesterol esterase, certain of the triglyceride lipases, and lipoprotein lipase are also influenced by the binding of heparin-like glycosaminoglycan chains. In addition, certain nuclear proteins, such as c-fos, c-jun, RNA polymerases, DNA polymerases, and steroid receptors have also demonstrated binding interactions with heparin-like molecules.

Heparan sulfate-mediated binding to cells is also implicated in the pathogenesis of infection by several pathogens, including protozoa, virus and bacteria. For example, herpes simplex virus (HSV) binds to cell surfaces via heparan sulfate, as does cytomegalovirus, attachment of the malarial circumsporozoite to the surface of hepatic cells is affected by the binding of heparin-like molecules, and trypanosomal adhesion is also mediated at least in part by heparan binding. Likewise, bacterial adhesion proteins of *Bordetella pertussis, Staphylococcus aureus*, and *Streptococcus pyogenes* are also shown to bind heparin-like molecules.

Furthermore, it has been discovered that the heparan sulfate chains of syndecans vary markedly from one cell type to another and these differences can be exploited for therapeutic and/or diagnostic purposes. In particular, the heparan sulfate chains syndecans-1, isolated from various cells differ not only in size but also in chemical structure (e.g., specific disaccharide composition and distribution). These structural differences appear to be a basis for differences in binding affinity of specific types of cells for particular ligands, and thereby permit the isolation and/or construction of decoys, agonists, antagonists and other substrates which can influence or measure biological activity.

In the case of wound repair, one therapeutic approach would be to isolate or construct an agent comprising a soluble heparan sulfate chain, potentially linked to a syndecan core protein or portion thereof, derived from a specific cell type which has an affinity for a growth factor, such as basic fibroblast growth factor, and then administer the agent via a pharmaceutically acceptable carrier to the wound site. The agent would then promote the migration and proliferation of fibroblasts and keritinocytes and/or mediate the activities of other repair cells at the wound site.

In another exemplary use, a therapeutic agent comprising a soluble heparan sulfate chain (cleared from a syndecan, or still attached) derived from a specific cell type which has an affinity for antithrombins or other circulatory factors can be employed to reduce or prevent arterial plaque deposits by sequestering factors which would otherwise impede the body's ability to eliminate or catabolize cholesterol or other lipoproteins implicated in atherosclerosis.

Likewise, therapeutic agents to treat pathogens can be devised. For example, cells which are naturally vulnerable to herpes simplex infections can be cultured and a soluble heparan sulfate chain with affinity for the herpes virus then derived therefrom. Such a therapeutic agent can be delivered topically or by injection to treat an herpes infection or as a prophylaxis (e.g., during childbirth) against such infections.

The cell-type specific heparan sulfate proteoglycans of the present invention can also be used for diagnostic purposes by employing regents which include heparan sulfate chains having specific affinity for particular ligands as substrates for competitive reactions, in various assays using enzymatic or radiolabeled indicators, according to techniques well known in the art.

In the treatment of certain diseases, such as hyperplasias or neoplasias, it may be desirable to administer a syndecan agonist in circumstances where an increase in a biological effect mediated in part by heparan sulfate is desired. "Agonist" refers to syndecan, a suitable homolog, or a portion thereof, capable of promoting at least one of the biological responses normally associated with syndecans. For example, partial proteolytic digestion of syndecan results in smaller peptides, some of which retain the heparan sulfate moiety as well as at least a portion of the biological activity of the intact syndecan protein. Thus, fragments of syndecan may serve as syndecan agonists. Agonist also refers to chimeric proteins which containing at least a heparan sulfate chain from a syndecan, attached to a biological effector molecule such that at least a portion of the biological activity of the effector molecule is retained and/or enhanced.

In other instances, it may be desirable to administer syndecan antagonists, such as a mutant form of syndecan or a syndecan homolog which blocks at least one of the normal actions of syndecan. For example, treatment with certain syndecan antagonists can down-regulate the mitogenic activity of a heparin-binding growth factor (HBGF). Antagonists include syndecan homologs having altered heparan sulfate chains, such as those identified by combinatorial analysis (see section IV), as well as fusion proteins which inhibit the mitogenic activity of an HBGF by competitively binding its receptor, alternatively, by binding the HBGF itself and sequestering it. For instance, in the presence of the chimeric FGF-receptor/syndecan protein described below, the bFGF has reduced ability to mediate biological responses normally associated with it as it becomes sequestered by the chimeric FGF-receptor. Also, as described below, chimeric VEGF antagonists can be used to inhibit neovascularization of tumors, and chimeric HB-EGF antagonists can be used to inhibit smooth muscle proliferation in the treatment of atherosclerosis. Similar to the use of antagonistic syndecan antagonists, anti-syndecan antibodies can be used to decrease mitogenic levels of growth factors by preventing heparan sulfate binding.

The present invention, by making available purified and recombinant syndecan, will allow the development of assays which can be used to screen for drugs which are either agonists or antagonists. By mutagenesis, and other structural surveys of syndecan-1 or its homologs, rationale drug design can be employed to manipulate syndecans or portions thereof, as either agonists or antagonists, as well as facilitate design of small molecule agonists and antagonists.

The surface of endothelial cells is non-thrombogenic because of the anti-coagulant properties of the heparan sulfate chains in a proteoglycan on their surfaces. Preparations of this highly anti-coagulant heparan sulfate proteoglycan in soluble form is now possible by transfection of cultured endothelial cells with a DNA construct defined by this invention. Expression of the construct would produce a syndecan containing endothelial cell-derived heparan sulfate chains. The recombinant syndecans can be engineered to contain, unique protease-susceptible sites in the extracellular domain allowing the harvesting of soluble portions of syndecan proteins as soluble products in high yield and purity. In another embodiment of the invention, tissue culture preparation of soluble portions of syndecan-1 can be greatly simplified by expression of truncation mutants, such as those described herein, which are entirely secreted into the culture media. Such molecules are particularly advantageous where the culture cell is an adherent cell. Syndecan can extracted from the culture media without disruption to the cells, and is particularly useful in conjunction with continuous cell culture techniques used for adherent cells. This approach can be used, by way of illustration, to produce an anticoagulant proteoglycan with very high potency, potentially several thousand times more potent than commercially available heparin. These soluble products can represent a singular molecular species, whereas the heparins and all other heparan sulfate proteoglycans containing compositions heretofore described represent many molecular species. The greater uniformity afforded by the present invention leads to greater potency and potentially to greater specificity of the materials being purified, thereby enhancing their therapeutic applications. Accordingly, existing materials such as heparin from pig intestine or beef lung or dextran sulfate, a synthetic product, that are polydispersed, of low potency, and of little specificity, can be replaced by genetically engineered products of the present invention.

The soluble proteins or peptides containing cell-type-specific heparan sulfate chains, made possible by this invention, can be used in the prevention and therapy of certain viral diseases. Dextran sulfate and heparin have been shown to reduce infection and replication of certain retroviruses, including human immunodeficiency virus (HIV). However, these molecules are highly heterogenous and are probably non-specific. A more specific inhibitor would be a soluble heparan sulfate peptide or proteoglycan derived from a cell type that interacts with the virus.

Production of the heparan sulfate proteoglycan defined by this invention will allow the manufacture of molecules that bind growth factors. These proteoglycans are of significant therapeutic value in those instances where local growth factor effects would be useful. A DNA construct derived from this invention can be used in a cell-type, such as fibroblasts, that contain surface proteoglycans that bind various growth factors, including acidic fibroblast growth factor (FGF) and basic FGF. This binding potentiates the action and prevents the proteolytic degradation of these growth factors. Platelet-derived growth factor (PDGF) binds to heparin in vitro, and the syndecan-1 DNA construct could be used to prepare large amounts of soluble PDGF binding proteoglycan.

VI. Construction of Chimeric Syndecan Molecules providing products that are not otherwise available. As used herein, the term chimeric molecule denotes macromolecules having portions which are heterologous in origin relative to one another. The chimeric molecule of the present invention comprises at least one heparan sulfate chain, derived from a syndecan, which is covalently coupled to another molecule (termed here "heterologous molecule") such as, for example, a polypeptide chain, a lipid or fatty acid moiety, or a small molecule such as an organic antiviral or antiparasitic agent having a molecular weight of, for example, from 100 to 1500. In such a manner, the biological activity of the heparan sulfate chain, such as its ability to influence binding affinity or specificity, can be imparted upon the other portions of the chimeric molecule. The covalent linkage of a sy -continued L-P-P-F-V-T-K-A-A-T-T-R-A-T-T-L-E-T-P-T-T-S-I-P-E-T-S-V-L-T-E-V-
T-T-S-R-L-V-P-S-S-T-A-K-P-R-S-L-P-K-P-S-T-S-R-T-A-E-P-T-E-K-S-T-
A-L-P-S-S-P-T-T-L-P-P-T-E-A-P-Q-V-E-P-G-E-L-T-T-V-L-D-S-D-L-E-V-
P-T-S-S-G-P-S-G-D-F-E-I-Q-E-E-E-E-T-T-R-P-E-L-G-N-E-V-V-A-V-V-T-
P-P-A-A-P-G-L-G-L-N-A-E-P-G-L-I-D-N-T-I-E-S-G-S-S-A-A-Q-L-P-Q-K-
N-I-L-E-R or a portion of the extracellular domain such as;

P-R-A-L-L-S-R-P-C-G-T-K-M-P-A-Q-L-R-G-I-A-V-L-L-L-L-S-A-R-A-A-   (amino acids 1–95 of SEQ ID NO: 8)
L-A-Q-P-W-R-N-E-N-Y-E-R-P-V-D-L-E-G-S-G-D-D-D-P-F-G-D-D-E-L-D-D-
A-Y-S-G-S-G-S-G-Y-F-E-Q-E-S-G-L-E-T-A-V-S-L-T-T-D-T-S-V-P-L-P- and in the case of syndecan-4 chimeras, the extracellular domain represented by the formula;

E-S-L-R-E-T-E-V-I-D-P-Q-D-L-L-E-G-R-Y-F-S-G-A-L-P-D-D-E-D-V-V-G-   (SEQ ID NO: 6)
P-G-Q-E-S-D-D-F-E-L-S-G-S-G-D-L-D-D-L-E-D-S-M-I-G-P-E-V-V-H-P-L-
V-P-L-D-N-H-I-P-E-R-A-G-S-G-S-Q-V-P-T-E-P-K-K-L-E-E-N-E-V-I-P-K-
R-I-S-P-V-E-E-S-E-D-V-S-N-K-V-S-M-S-S-T-V-Q-G-S-N-I-F-E-R or a portion of the extracellular domain such as;

E-S-L-R-E-T-E-V-I-D-P-Q-D-L-L-E-G-R-Y-F-S-G-A-L-P-D-D-E-D-V-V-G-   (amino acids 1–46 of SEQ ID NO: 6)
P-G-Q-E-S-D-D-F-E-L-S-G-S-G The chimeric proteins of the present invention can be generated so as to act as either antagonists or agonists to the biological activity of a particular biological ligand. For example, the activity of a number of growth factors can be potentiated by the addition of either heparin or heparan sulfate chains of a proteoglycan and can be used to generate chimeric growth factors with enhanced binding abilities. Exemplary growth factors useful in creating the chimeric syndecan molecules of the present invention include: growth factors of the heparin-binding growth factor (HBGF) family such as basic fibroblast growth factor (bFGF), acidic FGF (aFGF), Int-2, hst/K-FGF, FGF-5, and FGF-6; heparin-binding EGF-like growth factor (HB-EGF), platelet-derived growth factor (PDGF), transforming growth factor-β (TGF-β), vascular endothelial growth factor (VEGF), vascular permeability factor (VPF), hepatocyte growth factor; interferon γ; and Schwannoma-derived growth factor (SDGF), all of which have demonstrated regulation of biological activity by heparin or heparan sulfate. The role of the heparan sulfate glycosaminoglycan chain in regulating the activity of such cytokines is not well defined, but seems to include, as in the case of the HBGFs, conferring such attributes as protection against proteolytic degradation, enhancing chemical stability, and facilitating binding of the growth factor to its cell surface receptor. By way of illustration, a chimeric protein comprising a portion of bFGF and at least a portion of a syndecan containing a heparan sulfate chain can be constructed as described herein. Basic FGF is a heparin-binding polypeptide growth factor that is mitogenic and chemotactic for a variety of cells of mesodermal and neuroectodermal origin. These activities of bFGF are derived from its specific interaction with one or more high affinity receptors (bFGF-R). These integral transmembrane proteins (bFGF-R) have intracellular tyrosine kinase domains and have been identified on 3T3, endothelial, baby hamster, and PC-12 cells. Several in vitro studies have demonstrated that both heparin and heparan sulfate protect bFGF from protease digestion or heat/acid inactivation (Burgess et al. (1989) *Annu Rev Biochem,* 58:575; and Klasbrun (1989) *Progress in Growth Factor Res.,* vol 1, pp 207–235, Pergamon Press, Oxford England). Other studies have provided evidence that heparin or heparan sulfate acts as a cofactor and promotes the binding of bFGF to its high affinity receptor, thereby enhancing mitogenic activity of bFGF. Basic FGF is also known to interact with cell surface and extracellular heparan sulfate proteoglycans, such as syndecan-1 (also termed "low affinity bFGF receptor) and is the proximate source of the heparan sulfate which mediates subsequent binding of bFGF to the high affinity receptor. Expression of a chimeric bFGF/heparan sulfate molecule would be expected to act agonistically, being able to bind the bFGF high affinity receptor and act as a mitogen in an enhanced fashion to wild-type bFGF. A chimeric construct of this type can be therapeutically useful inasmuch as the half-life of the chimeric molecule can be longer than bFGF itself, can further have a higher binding affinity for the bFGF-receptor, and can be chemically stable to otherwise adverse environments.

In a related fashion, antagonistic variants of growth factors can be generated as chimeric proteins of the present invention. To illustrate, the binding of certain forms of VEGF to their cell-surface receptor is potentiated by heparin-like molecules. In addition, the binding of VEGF to $\alpha_2$-macroglobulin ($\alpha_2M$) leads to the inactivation of VEGF as complexed VEGF can no longer bind VEGF receptors of vascular endothelial cells. The binding of $\alpha_2M$ and heparin-like molecules is at least partly competitive, and their binding sites on VEGF are believed to overlap. A chimeric protein comprising an antagonistic variant of VEGF (e.g. one which binds the receptor but is not mitogenic) and a syndecan derived heparan sulfate GAG chain can be a more potent antagonist relative to the VEGF variant alone, as the chimeric protein would be less likely to be inactivated by $\alpha_2M$ due to the presence of the heparan sulfate. Such a chimeric protein could be used, for instance, in the treatment of tumors by inhibiting vascularization of the tumor. Similar interactions and role for heparan sulfate are visualized for isoforms of transforming growth factor-$\beta$.

Likewise, chimeric HB-EGF antagonists can be generated which include at least the heparan sulfate chains of a syndecan. HB-EGF itself is a potent mitogen of smooth muscle cells. A chimeric protein comprising an antagonistic variant of HB-EGF and heparan sulfate glycosaminoglycan chains can be used in the treatment of such vascular diseases as atherosclerosis.

Antagonists can also be generated from chimeric proteins comprising receptors for one or more growth factors and syndecan derived heparan sulfate chains. While syndecan-1 is itself believed to be a low-affinity for such cytokines as bFGF, a more potent antagonist might be constructed from the high-affinity receptor for bFGF. To illustrate, a fusion protein comprising the active binding site of high affinity bFGF-receptor and a heparan sulfate attachment sequence can be generated to create a soluble chimeric receptor with greater affinity for bFGF then either the receptor or the low affinity receptor alone. Such a chimeric receptor takes advantage of the role of the heparan sulfate chains in facilitating binding of bFGF to the receptor, and the chimeric can be used to sequester bFGF. Equivalent constructs comprising receptors for other growth factors which bind heparin like molecules can be made.

Chimeric molecules comprising protease inhibitors and heparan sulfate glycosaminoglycan chains derived from syndecans can be therapeutically effective as, for example, modulators of clot formation and dissolution, as anti-metastatic agents, and as birth control agents. For example, to enter a blood vessel and metastasize to other sites, a tumor cell must lyse the collagenous matrix of the surrounding capillaries. The action of a proteolytic enzyme such as plasminogen activator is believed to participate in this process in a manner similar to the process of implantation of a blastocyst into the uterus. The protease inhibitor nexin I has been shown to inhibit the activity of this serine protease and reduce the metastatic ability of tumor cells. Moreover, the inhibitory effect of Nexin is modulated by the binding of heparin-like molecules. Thus, a fusion protein comprising at least a portion of the amino acid sequence of nexin I and a functional heparan sulfate attachment sequence derived from a syndecan can be used in the treatment of tumors as a preventative agent of metastasis.

Chimeric heparan sulfate molecules are also useful as diagnostic tools. For example, a fusion protein comprising an alkaline phosphatase activity and a soluble portion of a syndecan which includes a heparan sulfate glycosaminoglycan can be utilized in chromogenic assays. Likewise, chimeric syndecans can be used to construct MRI contrasting agents which are localized based on interactions mediated by the heparan sulfate chains.

In addition, the chimeric syndecans of the present invention will have utility in cell culture techniques. For example, the syndecan/fibronectin fusion protein described in Example 11 can be used in tissue culture, and can be especially useful in the culturing of adherent cells. These chimeric syndecans can be used, for example, in biomaterials engineering to produce artificial vessels or prosthesis, influencing the adhesion and morphology of cells attached thereto. In addition, such molecules can effect the binding of other biological ligands to the culture device, such as extracellular-superoxide dismutase (e.g. to sequester any anti-oxidant).

As set out above, the chimeric protein of the present invention can be constructed as a fusion protein containing a functional heparan sulfate attachment sequence of a syndecan and at least a portion of one or more heterologous proteins, expressed as one contiguous polypeptide chain. In preparing the syndecan fusion protein, a fusion gene is constructed comprising DNA encoding at least one heparan sulfate attachment sequence of a syndecan homolog, the heterologous protein sequence(s), and optionally, a peptide linker sequence to span the two fragments. To make this fusion protein, an entire protein, such as an HBGF or an HBGF-receptor, can be cloned and expressed as part of the protein, or alternatively, a suitable fragment thereof containing a biologically active moiety can be used. Likewise, the entire cloned coding sequence of a syndecan or alternatively, a fragment of the molecule capable of directing attachment of heparan sulfate to the fusion protein can be used. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) *Nature* 339:68, incorporated by reference herein.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, Eds. Ausubel et al. John Wiley & Sons: 1992).

It may be necessary in some instances to introduce an unstructured polypeptide linker region between the portion of the fusion protein which directs attachment of heparan sulfate GAGs and other fragments. This linker can facilitate enhanced flexibility of the fusion protein allowing the heparan sulfate chains to freely interact with a surface component of, for example, a receptor, reduce steric hindrance between the two fragments and allow appropriate interaction of the heparan sulfate GAGs with the another component of the fusion protein, as well as allow appropriate folding of each fragment to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. No. 5,091,513, both incorporated by reference herein. Naturally occurring unstructured linkers of human origin are preferred as they reduce the risk of immunogenicity.

The chimeric molecules of the present invention can also be generated using well-known cross-linking reagents and protocols. For example, there are a large number of chemical cross-linking agents that are known to those skilled in the art and useful for cross-linking the heterologous molecule with a syndecan or a portion thereof. For the present invention, the preferred cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art. These include: succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl)aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-tolune (SMPT), N-succinimidyl 3-(2-pyridyldithio)propionate (SPDP), succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate-2 HCl (DMP) are examples of useful homobifunctional cross-linking agents, and bis-[B-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in this invention. For a recent review of protein coupling techniques, see Means et al. (1990) *Bioconjugate Chemistry* 1:2–12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5–7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

The reaction buffer should be free of extraneous amines and sulfhydryls. The pH of the reaction buffer should be 7.0–7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the protein chosen for reaction with maleimides, activated halogens, or pyridyl disulfides must contain a free sulfhydryl, usually from a cysteine residue. Free sulfhydryls can be generated by reduction of protein disulfides. Alternatively, a primary amine may be modified with Traut's Reagent to add a sulfhydryl (Blattler et al. (1985) Biochem 24:1517, incorporated by reference herein). Again, Ellman's Reagent can be used to calculate the number of sulfhydryls available in protein.

In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with —SH groups at slightly acidic to neutral pH ranges (6.5–7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing protein under the appropriate buffer conditions. The protein-protein conjugates can be isolated from the reaction mixture by methods such as gel filtration or by dialysis.

In addition to those uses set forth above, the chimeric syndecans of the present invention can be used to deliver small molecules, such as organic therapeutic agents. For example, delivery of acyclovir to HSV-infected cells can be mediated by the chimeric proteins of the present invention. Acylovir-loaded liposomes can be prepared in which a chimeric syndecan protein comprising heparan sulfate, and if desired, chondrotiin sulfate, is displayed on the surface of the liposome. To illustrate, a truncated syndecan consisting of a portion of the extracellular domain can be made as described in Example 9 below. The purified syndecan fragment can be derivatized with a lipid component, such as a fatty acid chain (e.g. a palmitoyl moiety) using such techniques as described by Kalvakolanu et al. (1990) Biotechniques 11:218; and the Huang U.S. Pat. Nos. 4,957,735, 4,925,661, and 4,708,933. In one embodiment, unilamellar liposomes can be prepared by using a small quantity of unsaturated phosphatidylethanolamine (PE) and a stabilizing amount of the fatty acid derivatized syndecan as described in the Huang U.S. Pat. No. 4,957,735 under conditions wherein acylovir is entrapped within the syndecan-liposome. Similar approaches can be used to encapsulate other therapeutic agents which can be selectively delivered in the syndecan-liposome.

Alternatively, a portion of the syndecan molecule containing at least the heparan sulfate attachment sequence of the extracellular domain and a transmembrane domain can be engineered to be resistant to proteolytic cleavage by removing the protease susceptible site. Intact naturally occurring syndecan, as described above, is labile and when incorporated in liposomes can be quickly degraded to destroy the specificity of the liposome. A proteolytic resistant variant, incorporated into a liposome by standard techniques, can therefor result in a more useful product.

The therapeutic agent can also be cross-linked as described above. For instance, particularly useful derivatives of acyclovir for cross-linking to syndecans can be represented by the formula:

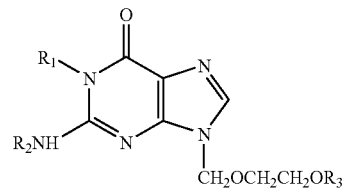

where one of $R_1$, $R_2$ or $R_3$ is a linking moiety (R) which preferably includes an acid labile bond, and the others are hydrogens. The acyclovir linking group (spacer) represented by R can be a group of from 0 to 50 atoms other than hydrogen although even larger spacers could be effectively utilized in preparing acyclovir derivatives by attaching an acyclovir analog to groups such as oligopeptides, polyamino acids, polymers, carbohydrates and/or cyclic groups as well as by glutaraldehyde copolymerization of aminated acyclovir analogs with polyamino acids. The atoms comprising R can include from 0 to 30 carbon atoms and from 0–25 hetero atoms selected from oxygen, nitrogen, sulfur and halogen. Generally the atoms of R are present in functional groups as for example alkyl, carbonyl, nonoxocarbonyl, hydroxy, alkoxy, amido, halo, thiocarbonyl, cyano, nitrilo, thio, imino, amino, carbalkoxy, mercuri, phthalimido, formyl, keto, succinimidoxy, thiocarbamyl, azo, hydroxyphenyl, and imidazolyl, as well as other saturated or unsaturated carbocyclic or heterocyclic rings. Preferably R can be from 0 to 30 atoms other than hydrogen including 0 to 20 carbons and 0–10 hetero atoms. More preferably R can be from 1 to 23 atoms other than hydrogen including 1 to 16 carbons and 0–7 hetero atoms. It is even more preferred that R is succindioyl, aminoalkyl or of the structure —$(CH_2)_n$—CO— or —$(CH_2)_n$—NH— or —CO—$(CH_2)_n$—CO—, where n is a whole number from 1 to 19, preferably 1 to 8.

Methods for making derivatives of similar analogs are described in U.S. Pat. No. 5,051,361 in which suitable linker groups are disclosed. These methods are well known in the art. Other methods deemed acceptable to making acyclovir derivatives suitable for conjugation are described by Nerenberg et al. 1986 Pharaceutical Research 3:112 and Quinn et al. 1979 Analytical Biochemistry 98:319.

Cell lines containing the genetic material necessary for the practice of the present invention can be obtained from a number of public sources, some of which are specifically identified in the following examples. For example, normal mouse mammary epithelial cells can be prepared from normal mouse tissue using the procedure described in the examples below. The same procedure can be used to obtain genetic material from other species.

The invention now being generally described, it will be more readily understood by reference to the following examples which are included for purposes of illustration only and are not intended to limit the invention unless so stated.

EXAMPLE 1 cDNA Libraries

NMuMG mouse mammary epithelial cells (passages 13–22) were maintained in bicarbonate-buffered Dulbecco's modified Eagle medium (Gibco) as described previously, David, G., and Bernfield, M., Proc. Natl. Acad. Sci. USA (1979) 76: 786–790. For preparation of poly(A) RNA, cells were plated on 245×245 mm tissue culture plates (Nunc) at approximately one-fifth confluent density and grown to 80–90 percent confluency (3–4 days). Following brief washing with ice-cold PBS the cells were solubilized in RNA extraction buffer (4 M guanidine isothiocyanate in 5 mM sodium citrate pH 7.0, 0.1 m β-mercaptoethanol and 0.5% N-lauryl sarcosine) and total RNA prepared by CsCl density centrifugation, Chirgwin, J. M., Pryzybyla, A. E., MacDonald, R. J., and Rutter, W. J., *Biochemistry* (1979) 18: 5194–5299. Poly(A) RNA was purified by chromatography on oligo(dT)-cellulose (type 3; Collaborative Research) and utilized in the commercial synthesis (Strategene) of cDNA by the S1 method, Huynh, T. V., Young, R. A., and Davis, R. W., DNA *Cloning: A Practical Approach* (1985) 49–78. Following addition of EcoRI linkers, those cDNA greater than 1 kb in length were isolated by gel filtration chromatography inserted into the EcoRI sites of λgt-10 and the expression vector λgt-11 and packaged. A portion of the λgt-11 library was amplified for later study, while the remainder was screened immediately without expansion.

A primer extension cDNA library was prepared using the RNase H method, Gubler, U., and Hoffman, B. J., *Gene* (1983)25: 263–269. First strand cDNA was synthesized from 10 ug of an 18-bp oligonacleotide containing sequence derived from near the 5' end of PM4 (see Example 2). The second strand was synthesized using RNase H(BRL) and DNA polymerase Klenow fragment (Boehringer-Mannheim). The cDNA was methylated with EcoRI methylase and then ligated with synthetic EcoRI linkers (New England Biolabs). Excess linkers were removed by EcoRI digestion and the cDNA was purified on agarose gel electrophoresis and recovered by electroelution. The resulting cDNA was inserted into λgt-10 (Promega and packaged using Giga pack Gold (Stratagene).

EXAMPLE 2

Isolation of Syndecan-1 cDNA Clones

The preparation of a rabbit serum antibody to the ectodomain of NMuMG syndecan-1 has been described elsewhere, Jalkanen, M., Rapraeger, A., and Bernfield, M., J. *Cell Biol.* (1988) 106: 953–962. For screening clones in λgt-11, the immunoserum was first absorbed against *E. coli* proteins to reduce background. Briefly, a 500 ml culture of *E. coli* strain Y1090 was grown to saturation in the presence of 50 ug/ml ampicillin. Following centrifugation, the cells were resuspended in 50 ml TBST (Tris buffered saline triton: 10 mM Tris pH 7, NaCl 150 mM, Triton X-100 0.3%), sonicated, and following addition of 100 ul immunoserum (1:500 dilution), incubated overnight at 4 C. This mixture was centrifuged for 10 min at 4000 rpm and used to screen expressed λgt-11 cDNA clones, Young, R. A., and Davis, R. W., *Science* (1983) 22: 778–782, by detection with alkaline phosphate-conjugated goat-antirabbit IgG (Promega). Four antibody reactive clones were identified from 7.5×105 recombinants and were plaque-purified. Northern and Southern hybridization experiments allowed grouping of these clones into three distinct sets of related clones. Two of these sets produced fusion proteins that reacted with immunoserum affinity-purified against the ectodomain of syndecan-1. A 2.1-kb clone from one of these sets, PM-4, was found to contain a sequence that exactly matched the partial amino acid sequence of a cyanogen bromide-cleaved fragment of the ectodomain of syndecan-1. Additionally, syndecan-1 purified from NMuMG cells reacted with an immunserum prepared against a synthetic peptide containing the C-terminal 7 amino acids (Lys-Gln-Gln-Glu-Glu-Phe-Tyr-Ala) of the PM-4 derived protein sequence. This immunserum failed to react with the ectodomain which lacks the putative cytoplasmic domain. Furthermore, this serum does not cross react with any other cellular proteins as assessed by Western blotting of total cell extracts.

Additional screeing of the NMuMG λgt-10 libraries was performed using radiolabeled fragments from the 51 end of PM-4 (250 bp EcoRI-HincII fragment). cDNA fragments isolated from SeaPlaque agarose (FMC BioProducts) were labeled with 32 p by random oligonucleotide priming, Feinberg, A. P., and Vogelstein, B., *Addendum. Anal. Biochem.* (1984) 137: 266–267, and used as described by Maniatis, T., Fritsch, E. F., and Sambrook, J., *Molecular Cloning: A Laboratory Manual* (1982). This screening yielded two clones, 4–19B and 4–15. Additional screening of a primer-extended I gt-10 cDNA library, prepared with liver poly(A) RNA and a synthetic oligonucleotide complimentary to a site near the 5' end of PM-4 (positions 848–865 in Table 1) was screened with the same 250 bp probe. Several independent clones were characterized from this library; each contained a 5' sequence identical with that of clone 4–19B.

EXAMPLE 3

Subcloning and DNA Sequencing

Purified lambda DNA was prepared from positively selected clones by Lambdasorb immunoprecipitation (Promega). Fragments released by restriction endonuclease digestions were isolated by electrophoresis followed by excision from SeaPlaque agarose (FMC BioProducts). These isolated fragments were subcloned directly, in the presence of agarose, Struhl, K., *BioTechniques* (1985) 3: 452–453, to either pGEM 3 and 4 for in vitro transcription, or M13 mp18 and mp19, Messing, J., *Methods Enzymol.* (1983) 101: 2078, for sequence analysis.

DNA sequencing was performed by the dideoxy chain termination method, Sanger, F., Nicklen, S., and Coulson, A. R., *Proc. Natl. Acad. Sci. USA* (1977) 74: 5463–5467, using a modified T7 DNA polymerase (Sequenase™, U.S. Biochemical). Sequence was generated from both ends of subcloned restriction fragments using universal M13 sequencing primers. The internal sequence of large fragments as well as the complementary strands of all fragments were determined using oligonucleotide primers synthesized in accordance with preceding sequences. Sequencing artifacts generated as the result of G-C compression were avoided by determining all sequences using both dGTP and the nucleotide analogue dITP.

The cDNA (SEQ ID NO: 1) has the following features: The first AUG is at postion 240. This putative intiation codon is preceded by two inframe termination codons (TAA and TGA at positions 39 and 72 respectively) and followed by a 930 base open reading frame that ends at position 1173 with a TGA termination codon. Following the putative coding region are 1,243 bases of 3'-untranslated sequence that ends with the poly(A) stretch. Because each of the primer extended clones has the same 5' end as the largest cDNA clone from the NMuMG library, M-4-19B, this sequence appears to include the complete 5'-untranslated region of syndecan-1. Other features have been previously discussed.

EXAMPLE 4

Northern Blots

RNA for Northern analysis was prepared from the following: NMuMG cells, adult liver, newborn skin, midpregnant mammary gland, adult cerebrum, skeletal and cardiac muscle. Excised tissues were ground to a fine powder in the presence of liquid nitrogen and transferred directly to RNA exraction buffer (see above); the NMuMG cells were extracted after washing with PBS as described above. The samples were vigorously vortexed, an equal volume of 10 mM Tris pH 8.0, 1 mM EDTA, and 1% SDS added, and subsequently extracted exhaustively with 24:24:1 Tris-saturated phenol:chloroform:isoamyl alcohol followed by a single extraction with 24:1 chloroform:isoamyl alcohol. Following precipitation with an equal volume of 2-propanol, and resuspension in 10 mM Tris pH 7.5, 1 mM EDTA, RNA was precipitated by addition of ⅓ volume of 10 M LiCl. Poly(A) RNA was prepared by oligo d(T) chromatography as described above.

For Northern analysis, 2 ug of each poly(A) RNA sample was separated by electrophoresis in 1.2% agarose-formaldehyde gels in the presence of MOPS (Sigma)-Acetate buffer pH 7.0, Maniatis, T., Fritsch, E. F., and Sambrook, J., *Molecular Cloning. A Laboratory Manual* (1982). Following alkali treatment, Danielsen, M., Northrop, J. P., and Ringold, G. M., *EMBO J.* (1986) 5: 2513–2522, and neutralization in transfer buffer (0.025 M sodium phosphate pH 6.5), the gel was blotted to Gene Screen and the RNA immobilized by UV cross-linking, Church, G. M., and Gilbert, W., *Proc. Natl. Acad. Sci. USA* (1984) 81: 1991–1995. Hybridization probes were prepared by in vitro transcription of the 5' EcoRI-SacI fragment of PM-4 subcloned into pGEM3, Melton, D. A., Krieg, P. A., Rebagliati, M. R., Maniatis, T., Zinn, K., and Green, M. R. p *Nucl. Acids Res.* (1984) 12: 7035–7056. Blots were prehybridized at 61° C. in 50% formamide, 1% SDS, 5×SSPE, 0.1% ficoll, 0.1% polyvinylpyrrolidone and 100 ug/ml denatured salmon sperm DNA. Hybridization was for 16 hrs at 61° C. in the same buffer containing 5×106 cpm/ml of RNA probe. Filters were washed 2×15 min at room temperature in 5% SDS/1× SSPE and 6×30 min at 67° C. in 1% SDS/0.1×SSPE. Molecular sizes were determined relative to ethidium bromide stained molecular weight markers (BRL) and 18S and 28S ribosomal RNA.

Northern blot analysis of the poly(A) RNA preparations revels two mRNA bands in NMuMG cells as well as in skin, liver and mammary gland tissues; one band is at 2.6 and the other at 3.4 kb. The apparent lower level of expression found in midpregnant mammary gland, as compared with skin and liver, consistent with the relative paucity of epithelial cells in the mammary gland. Longer exposures of the Northern blot discussed above, as well as others containing larger quantities of poly(A) RNA, verify that the mammary gland expresses both the 2.6 and the 3.4 kb messages (data not shown). Scanning densitometry shows that these two messages are present at a nearly constant relative abundance of 3:1 (2.6 kb:3.4 kb) in NMuMG cells and in skin, liver, and mammary gland tissues (data not shown). As expected from the immunohistology, neither of these mRNAs were present in detectable amounts in cerebrum and striated muscle tissues (skeletal and cardiac). However, Northern analysis consistently detected a distinct 4.5 kb mRNA in the cerebrum. The relationship of this message to that of syndecan-1 is currently not known.

EXAMPLE 5

Preparation and Use of Antibodies to Synthetic Peptides

A seven amino acid (14C-labeled) synthetic peptide, corresponding to the predicted C-terminus of syndecan-1 (SEQ ID NO: 1) was prepared by direct synthesis. The N-terminal lysine of this peptide was cross-linked by glutaraldehyde to keyhole limpet hemocyanin (KLH, Calbiochem) for immunization and bovine serum albumin (BSA, Fraction V, Sigma) for screening as described by Doolittle, R. F., *Of URFS and ORFS: A Primer on How to Analyze Derived Amino Acid SecLuences* (1986) 85. Briefly, 10 mg carrier protein was dissolved in 0.5 ml of 0.4 M phosphate, pH 7.5, mixed with 7.5 mmoles of peptide in 1.5 ml water and 1.0 ml of 20 mM glutaraldehyde was added dropwise with stirring over the course of 5 min. After continuous stirring at room temperature for 30 min., 0.25 ml of 1 M glycine was added to block unreacted glutaraldehyde and the stirring resumed for an additional 30 min. The product was dialyzed exhaustively against phosphate-buffered saline and incorporation determined by TCA precipitation and liquid scintillation counting. This procedure resulted in the attachment of 17 moles of synthetic peptide per mole of carrier protein.

For immunization, 1.25 mg of synthetic peptide-KLH conjugate in 0.5 ml PBS pH 7.5 mixed with 0.5 ml complete Freunds adjuvant. The emulsion was delivered by intramuscular injections, 0.1 ml in each of ten sites, into 3 month old New Zealand white rabbit. After 2 weeks, the immunization was repeated with an identical quantity of immunogen. 10 days later, the rabbit was injected with Innovar 0.125 ml/kg subcutaneously and was bled from the central auricular artery. Innovar was reversed with Nalline 0.2 ml/kg, and serum was prepared from the collected blood.

The native lipophilic form of syndecan-1 and the nonlipophilic medium ectodomain form, Jalkanen, M., Rapraeger, A., Saunders, S., and Bernfield, M., *J. Cell Biol.* (1987) 105: 3087–3096, were isolated and purified as described elsewhere and assessed for their reactivity to the immune sera. A cationic nylon membrane, Gene-Trans (Plasco Inc., Woburn, Mass.), was placed into an immunodot apparatus (V&P Scientific, San Diego, Calif.) and, samples of intact syndecan-1 and the ectodomain (0.5, 5, 50 and 500 ng) were loaded on the membrane using mild vacuum. After loading, remaining binding sites on the membrane were blocked by 1 hr incubation in a solution containing 0.5% BSA, 3% Carnation instant nonfat dry milk, 10 nM Tris (Sigma) pH 8.0, 0.15 M NaCl and 0.3% Tween-20. Incubation with immune serum was performed at dilutions of 1:200 for the anti-cytoplasmic domain, and 1:500 for the antiectodomain in 10 mM Tris pH 7.4, 0.15 M NaCl, and 0.3% Tween-20 (TBST) for 30 min at room temperature. The membrane was washed for 60 min at room temperture with ten changes of TBST and then incubated for 30 min with 1:7500 dilution of alkaline phosphatase goat-antirabbit IgG (Promega, Madison Wis.). Following washing for 60 min with ten changes of TBST, the immobilized alkaline phosphatase was visualized with nitro blue tetrazolium (NBT) 330 ug/ml and 5-bromo-4-chloro-3indolyl phosphate (BCIP) 165 ug/ml in 100 mm Tris pH 9.5, 100 mM NaCl, and 5 mM MgCl2.

EXAMPLE 6

DNA Construct for the Expression of Syndecan-1 Core Protein in Mammalian Cells Syndecan-1 can be expressed within mammalian cells by transfection of a DNA contruct containing the syndecan-1 core protein cDNA linked to a eukaryotic promoter that has the properties of both high-level expression and activity in a wide range of cell types. For example, the expression vector pHβ APr-1n-eo has been described (Gunning et al., PNAS 84:48314835) which utilizes the human β-actin promoter and fullfills both of the above requirements. This vector also contains the neomycin-resistance gene which allows selection of transfected cells with the antibiotic G418.

A SacI-HindIII fragment of the syndecan-1 cDNA (nucleotides 214–1379 of the sequence shown in (SEQ ID NO: 1) which encompasses all of the coding region was inserted directionally between the SalI-BamHI sites of the pHβ APr-1-neo vector and thus named pβ-SSyn-neo. In order to generate the necessary restriction sites on the 5' and 3' ends of the syndecan-1 cDNA fragment for insertion into this vector, this fragment was passed sequentially through pGEM 3Z (Promega), pGEM 7Zf (Promega), and Bluescript (Stratagene). Thus the resulting configuration of restriction sites at the point of insertion in pHβ APr-1-neo is as follows: SalI-ClaI-HindIII-EcoRV-EcoRI-SacI-syndecan-1 cDNA fragment-HindIII-BamHI.

This DNA construct was transformed into the bacterial strain TG-1 and prepared in large scale using routine plasmid preparation techniques including CsCl2 density centrifugation. The purified circularized plasmid DNA was transfected into Chinese Hamster Ovary (CHO) cells by standard calcium phosphate precipitation technique, and transfected clones were selected with G418.

Although the parental CHO (hamster) cells express mRNA which is cross-reactive with the murine syndecan-1 cDNA, neither whole cells nor proteoglycan purified from these cells is reactive with the monoclonal antibody 281-2, a rat monoclonal antibody generated against murine syndecan-1. Therefore it has been possible to assess the function of the transfected murine syndecan-1 gene using this antibody. By both quantitative radioimmunoassay and Western blotting, we have confirmed that clones of the transfected CHO cells express murine syndecan-1 at levels about ⅓ that expressed endogenously by NMuMG mouse mammary epithelial cells, the murine cell line which to date has demonstrated the highest natural levels of expression. Furthermore, a quantitatively higher level of murine syndecan-1 is actually accumulated in the culture media of these CHO cells versus the NMuMG cells, suggesting that the absolute rate of synthesis from the transfected gene is probably in excesses of even the highest natural levels in murine cells.

EXAMPLE 7

DNA Construct for Blocking Expression of Syndecan-1 Core Protein in Mammalian Cells We have constructed anti-sense cDNA vectors analogous to the sense constructs described above for the purposes of blocking syndecan-1 expression in mammalian cells. Anti-sense RNA produced from vectors of this type, if expressed in sufficiently high levels, is capable of binding to endogenous message intracellularly and blocking its subsequent translation.

To construct this vector, the same coding region SacI-HindIII fragment of syndecan-1 described above was inserted into the BamHI-HindIII site of the pHβ Apr-1-neo vector to produce the vector pβ-ASyn-neo. In this application, however, the cDNA was inserted into the vector in the opposite orientation so as to produce mRNA from the transfected gene that is complementary to endogenous syndecan-1 mRNA. To generate the appropriate restriction sites on the 5' and 3' ends of the syndecan-1 cDNA for insertion into this site, this fragment was sequencially passed through pGEM 3Z (Promega) and Bluescript (Stratagene). Thus, the resulting configuration of restriction sites at the point of insertion in pHβ APr-neo vector is as follows: HindIII-syndecan-1 cDNA fragment-ScaI-EcoRI-PstI-SmaIBamHl.

Upon transfection of this construct into NMuMG cells by calcium phosphate precipitation and selection with G418, we have observed two distinct morphological changes in these cells which appear to correlate with a reduction in the level of syndecan-1 expression. These morphological changes include a change from the normal cobblestone appearance of the epithelial monolayer to a fibroblastic and to a neoplastic morphology and cell behaviors.

EXAMPLE 8

Identification of Related Molecules with Degenerate Oligonuceotides

While in principle any degenerate oligonucleotide corresponding to the murine syndecan-1 gene product has a potential usefulness in the identification of related biological molecules, some oligonucleotide sequences have higher value. In studying the three putative glycosaminoglycan attachment sites in Syndecan-1 of the consensus sequence D/E-X-S-G-D/E (SEQ ID NO: 46), we have observed that two of these sites have a conserved G in the X position, and that furthermore all five glycosaminoglycan attachment sites in syndecan-1 utilize a single codon, TCT, of the six possible codons for the serine residue. Therefore, we expect that the 64 fold degenerate oligonucleotide of the form GAN GGN TCT GGN GA (SEQ ID NO: 19) (where N is all four nucleotides) should statistically have the highest probability of success in the identification of other gene products which contain this putative signal for glycosaminoglycan attachment. Similarily, the complementary oligonucleotide of the form TCN CCA GAN CCN TC (SEQ ID NO: 20) should have similar utility, with the added advantage of its ability to identify the messenger RNA of these gene products in Northern analysis.

EXAMPLE 9

Truncation Mutations of Syndecan-1

In a specific example of the invention, soluble truncations of the syndecan core protein including the heparan sulfate attachment sequences can be expressed by transfection into eukaryotic cells. This serves to demonstrate that the full syndecan core polypeptide and membrane association are not required to specify the attachment and synthesis of a heparan sulfate chain.

Specifically, four examples of syndecan-1 truncations are provided: 70/200, 70/201, 70/202 and 70/221 (The numbers are internal laboratory designations referring to specific oligonucleotides used in the PCR reactions creating these truncations). These truncations respectively represent DNA encoding amino acid residues 1–249, 1–176, 1–106 and 1–81 of syndecan-1 (SEQ ID NO: 1). The truncations were prepared by PCR (Polymerase Chain Recation). In each case the 5' end of the PCR product was generated with the oligonucleotide No. 70 (below) containing a HindIII endonuclease restriction site and nucleotides complementary to nucleotide residues 197–219 of the 5' untranslated region of murine syndecan-1. The 3' end of the PCR product was generated with a series of oligonucleotides (Nos. 200,201, 202,221) consisting of the appropriate nucleotides from the coding region of murine syndecan-1 to produce the described truncation, nucleotides encoding 6 Histidine residues in frame with the murine syndecan-1 coding region, a stop codon, and a BamHI restriction endonuclease site. The 6 Histidine residues were added to the C-terminal end of the coding region of these truncations to allow easy purification and analysis of the peptide products using nickle-agarose chormatography. 1–3 non-specific nucleotides are added 5' to the restriction endonuclease cleavage site to facilitate cutting at these sites prior to subcloning.

The oligonucleotide primers used are as follows:

```
No.70  C-T-A-A-G-C-T-T-A-T-C-C-A-C-G-A-A-G-C-C-  (SEQ ID NO: 25)
       C-A-C-C-G-A-G-C-T-C

No.200 G-C-C-G-G-A-T-C-C-T-C-A-G-T-G-A-T-G-G-T-  (SEQ ID NO: 26)
       G-G-T-G-A-T-G-G-T-G-G-T-C-C-A-A-A-A-G-G-
       C-T-C-T-G-A-G-A

No.201 G-C-C-G-G-A-T-C-C-T-C-A-G-T-G-A-T-G-G-T-  (SEQ ID NO: 27)
       G-G-T-G-A-T-G-G-T-G-G-T-C-A-G-G-T-T-G-A-
       C-C-A-G-G

No.202 G-C-C-G-G-A-T-C-C-T-C-A-G-T-G-A-T-G-G-T-  (SEQ ID NO: 28)
       G-G-T-G-A-T-G-G-T-G-G-A-G-C-A-C-A-G-G-C-
       T-C-T-C-C

No.221 G-C-C-G-G-A-T-C-C-T-C-A-G-T-G-A-T-G-G-T-  (SEQ ID NO: 29)
       G-G-T-G-A-T-G-G-T-G-G-C-T-G-G-T-G-G-G-C-
       T-C-T-G-G-A-G
```

The truncation DNA fragments were prepared by PCR using standard techniques. The reaction mixtures contained: 100 ng template DNA (Seq. ID No. 1), each dNTP at 200 µM, each oligonucleotide primer at 1 µM, 10 µl of Perkin-Elmer Cetus 10×PCR buffer, and 2.5 U Amplitaq DNA polymerase in a final reaction volume of 100 µl. The reactions were incubated in a Perkin-Elmer Cetus thermal cycler under the following conditions; 1st cycle: 95° C.×5 min., followed by 55° C.×1 min., followed by 72° C.×1 min., then for the next 30 cycles; 95° C.×1 min., followed by 55° C.×1 min., followed by 72° C.×1 min., and then for a final extention cycle; 95° C.×1 min.; followed by 55° C.×1 min., followed by 72° C.×7 min., and then cycled to 4° C. and held.

The resultant PCR fragments were purified by standard phenol/chloroform extraction and ethanol precipitation protocols. The resolubilized fragments were then digested with BamHI and HindIII, and resolved by Low Melting Temperature Agarose Gel (FMC, Rockland, Me.) electrophoresis. The fragments were recovered by excising the bands under direct UV visualization and used directly for subcloning into the mammalian expression vector pHβ APr-1-neo, previously cut with BamHI and HindIII. This vector contains a b actin promoter 5' of the insertion site and an SV40 polyadenylation sequence 3' of the insertion site, as well as other sequences useful for standard molecular biological manipulation (eg. Ampicillin resistance). See Gunning, et al. (1987) *PNAS* 84:4831–5.

DNA from the above construction was prepared by standard molecular biological techniques, including purification by two centrifugation spins through CsC12. See, for example Sambrook, J., Fritsch, E. F., and Maniatis, T., Molecular Cloning. A Laboratory Manual (1989), The purified DNA was transfected into chinese hamster ovary (CHO) cells by lipofection mediated DNA transfer. Specifically, 60 mm plates of CHO cells at 80% confluency were washed 3× with OptiMEM (Gibco) serum reduced media and then, 80 µl DOTAP (Boeringer-Mannheim) transfection reagent in 3 ml OptiMEM was added to the monolayer and incubated at 37° and 5% $CO_2$. After 1 hour preincubation, 20 µg of DNA construct was added in 0.5 ml OptiMEM and the cells incubated for an additional 6 hours. At that time the media was removed and replaced with 5 ml DMEM/Ham's F12 (Gibco) with 10% FCS and cultured for and additional 48 hours.

The conditioned media was collected from the transfected cells and 3 ml of conditioned media was made 4M with GndHCl. The media was then incubated with 150 µl of 50% slurry of Ni-NTA agarose (Qiagen) for 1 hr at r.t. then overnight at 4° C. The following day, the media was removed and the agarose beads washed by suspension and centrifugation with 4×1 ml of 4M GndHCl/TBS (Tris buffered saline) containing 20 mM imidazole, followed by 2×1 ml washes with 0.1M Tris pH 7.2 containing 0.1% Triton X100. The agarose beads were resuspended in 75 µl 0.1 M Tris pH 7.2 containing 0.1% Triton X-100 and divided equally to 3 microcentrifuge tubes. For each transfection construct: to one tube no additions were made, to one tube was added 5 µl Chondroitin ABCase (16 mU/µl), and to one tube was added 5 µl Chondroitin ABCase as above and 5 µl Heparitinase (0.3 mU/µl). The tubes were incubated for 1 hr at 37° C. and a second equal addition of respective enzymes were added and incubated for a further 1 hr. The beads were washed ×1 with 0.1 M Tris pH 7.2 containing 0.1% Triton X100 and then resuspended in 40μl SDS-PAGE sample buffer and boiled ×10 minutes. The entire sample including beads was loaded directly onto a Tris-Borate-EDTA/SDS-PAGE 3.5–25% gradient gel as previously described (Koda et al., 1985, JBC 260:8157–62). The PAGE gel was transferred by western technique to a cationic nylon membrane (Immobilon-N, Millipore) and stained with a monoclonal antibody 281-2 specific to the core protein of murine syndecan-1.

All of the truncations described in this example were demonstrated by this analysis to contain both heparan sulfate and chondroitin sulfate glycosaminoglycan chains. The specific truncations used in these examples were selected to maintain the peptide epitope for the monoclonal antibody 281-2, allowing facile identification of the transfected products by western blotting. However, one skilled in the art could easily construct other smaller truncations around the heparan sulfate attachment sequences, and by addition of suitable epitope "tags", characterize other truncations containing the desired activity of heparan sulfate chain addition. Furthermore, while we have taught that only a small segment of the syndecan core protein is essential for this desirable heparan sulfate chain additon, in other specific examples of this invention, larger regions of the syndecan core protein coding region may be specified to enhance certain aspects of the invention, such as the addition of heparan chains with certain desirable cell-type or otherwise specific binding activites.

EXAMPLE 10

Site Directed Mutation of GAG Attachment Serines

The smallest truncations of syndecan-1, demonstrated in Example 9, contain only the 3 most N-terminal glycosaminoglycan attachment sites. These truncations contain both heparan sulfate and chondroitin sulfate chains. While the desirable binding activities of these molecules reside in the heparan sulfate chains, for most applications the presence of the chondroitin sulfate chains on constructions of this invention would not adversly affect that activities of these products (and in some cases could enhance functionality). However, in refinements of the invention it is possible to further specify the attachment of heparan sulfate chains.

Evaluation of the syndecan-1 protein sequence reveals that the first putative attachment site (serine 37) has surrounding primary sequence which is similar to the fourth and fifth putative attachment sites (serine 207 and 217). These latter two attachment sites are understood to contain chondroitin sulfate chains only. The hypothesis that the attachment site at serine 37 also specifies chondroitin sulfate attachment has been demonstrated by site directed mutants.

A site directed mutant, SXX, of the syndecan-1 truncation 70/201 (example 9 above) that contains only serine 37 (serine 45 and serine 47 having been mutated to alanine residues), was generated by sequential PCR site directed mutagenesis as described in section 8.5.7 of Current Protocols in Molecular Biology, Eds. Ausubel et al. John Wiley & Sons: 1992.

This technique is well described in the referenced literature. In brief, the technique relies on the use of pairs of synthetic oligonucleotides, spanning the coding region of a cDNA to be mutated, that have the characteristics of 1) the introduction of single or multiple base pair mutations so as to encode a specific amino acid mutation 2) one of the pair of oligos nucleotides represents the sense strand and one oligos the antisense strand, and 3) there is complementarity between the 5' ends of the two oligonucleotides over a region of from 10–12 nucleotides. In the first step, two PCR reactions are performed. One utilizes a sense strand oligo from the 5' untranslated region of the cDNA of interest and and the antisense oligo of the complementary pair. The other reaction utilizes the sense strand oligo of the complementary pair and an antisense oligo from the 3' untranslated region of the cDNA of interest. The products of these two PCR reactions are two DNA fragments, encompassing the complete coding region of the cDNA, containing the desired site directed mutation, and with 10–12 nucleotides of complimentary sequence at the site of the mutation.

These fragment are purified away from the original primers, melted and reannealed to one another, and a second step PCR reaction carried out using only the two end primers external to the coding region. The resultant fragment corresponds to the original cDNA now containing a site directed muation.

For the production of the described site directed mutant SXX, the first step PCR reactions were carried out using the reaction conditions and template DNA described in Example 9, using olignucleotides No. 70 and No. 120 for one reaction and oligonucleotides No.225 and No. 201 for the other reaction.

The sequence of the oligonucleotide primers are as follows:

No.70 As in Example 9

```
No.120 T-G-T-G-C-C-A-G-C-G-C-C-A-G-C-G-A-A-G-T-T-   (SEQ ID NO: 30) (A→C Mutation)
        G-T-C-A-G-A No.225 C-T-G-G-C-G-C-T-G-G-C-A-C-A-G-G-T-G-C-T-T    (SEQ ID NO: 31) (T→G Mutation)
```

No.201 As in Example 9

The resultant DNA fragments from the first PCR reaction were analysed and purified by Tris-Acetate-EDTA agarose gel electrophoresis using 4% NuSieve (FMC, Rockland, Me.). The bands were excised under direct UV visualization, and the DNA recovered using Spin-X centrifuge filter units (Costar, Cambridge, Mass.) at 14,000×g for 30 minutes.

The second PCR step used reaction conditions identical to the first, however 1 μl of each of the fragments from the first reaction were mixed and used as template for the secondary reaction. The product of this final PCR step (site directed mutant SXX) was subcloned, purified, and used in transfection experiments as described for the truncations of Example 9.

Analysis of mutant SXX (soluble truncation of murine syndecan-1 containing; aa residues 1–176, a C-terminal 6His tag, and putative glycosaminoglycan sites at serine residues 45 and 47 mutated to alanine residues), by the methods described in Example 9 revealed that the single putative attachment site at serine residue 37 specified attachment of chondroitin sulfate only.

As an additional example of refinement of the invention, the complimentary site directed mutation XSS was prepared using the sequential PCR method described above and oligos No.70 with No.224 and No.32 with No.201 for the first step PCR reactions.

The sequence of the oligonucleotide primers are as follows:

No.70 As in Example 9

```
No.224 C-G-C-C-A-T-C-C-T-G-A-T-C-T-T-C-A-G    (SEQ ID NO: 32) (A→C Mutation)

No.32  C-A-G-G-A-T-G-G-C-G-C-T-G-G-G-G-A-T-G  (SEQ ID NO: 33) (T→G Mutation)
```

No.201 As in Example 9

This mutation also contains a soluble truncation of murine syndecan-1 containing; aa residues 1–176, a C-terminal 6His tag, and the first putative glycosaminoglycan attachment site at serine residue 37 mutated to alanine. The XSS truncation, containing the putative glycosaminoglycan attachment sites at serine residues 45 and 47, when tranfected and analyzed as described in Example 9 above, demonstrated specificity for heparan sulfate chain attachment as well as residual chondroitin sulfate chain attachment. Thus the attchment site at serine 37 is not essential for the implimention of this invention, but may if desirable be retained for certain active forms of the invention. The extent of substitution of the XSS mutant with heparan sulfate v.s. chondroitin sulfate was also noted to be dependent somewhat on cell type and efficiency of core protein expression, thus allowing those skilled in the art to further adapt the products of this invention to specific applications.

Further site directed mutations of the syndecan core protein sequence allow more complete specification of the heparan sulfate attachment sequence. For example, a site directed mutant XSX was created, using point mutated oligonucleotides and the sequential PCR technique as described in detail in the examples above, to further mutate the XSS site directed mutant illustrated above. This mutation contains: aa residues 1–176 of murine syndecan-1, a C-terminal 6His tag, and mutation of both the putative attachment sites at serine residues 37 and 47. This site directed mutant when subcloned, transfected into CHO cells, and analyzed as above, demonstrated a significant impairment in heparan sulfate attachment and synthesis. Thus confirming the importance of the Ser-Gly-Ser-Gly attachment sequence identified in this invention for heparan sulfate attachment.

Examination of the syndecan sequence alignments, shown above, allows the identification of other candidate amino acid residues for muational analysis. For example, the high degree of conservation of a phenolic residue N-terminal to the Ser-Gly-Ser-Gly attachment site suggests its importance in specifying the heparan sulfate attachment sequences of this invention. A site directed mutation has been created, using the methods described in the exmples above, where the phenylalanine of murine syndecan-1 has been replaced with an alanine residue. While this type of mutation does have effects on the specification of heparan sulfate attachment, as expected, such effects are much less prominant then the effects of direct mutation of the attachment serine residues as described by Example 9 above.

Finally, it is generally assumed that glycosaminglycan chains are typically attached to serine residues followed immediately by glycine residues. It is on this basis that we have described the 5 putative glycosaminoglycan attachment sites of syndecan-1, and specifically the 3 putative attachment sites near the N-terminus (serine residues 37, 45, and 47) described in the truncations above. In the case of chondroitin sulfate attachment to other proteins, a number of exceptions to this general principle have been described. Therefore, in a consideration of heparan sulfate attachment, such as this invention, it is essential to confirm that these indeed are the only residues involved in glycosaminoglycan attachment to syndecan-1.

A site directed mutant XXX was constucted by the techniques outlined above. This mutation contains aa residues 1–176 of murine syndecan-1, a C-terminal 6His tag, and all three of the putative glycosaminoglycan attachment residues (serine 37, 45 and 47) mutated to alanine residues. When transfected into CHO cells and analyzed as decribed above, this mutant contains no glycosaminoglycan chains, thus confirming the assignment of these three residues as the only sites of glycosaminoglycan attachment in the N-terminal truncations.

EXAMPLE 11

Syndecan-Fibronectin Chimera

As described elsewhere in this application, the disclosure of syndecan sequences that specify the attachment and synthesis of heparan sulfate allow the genetic engineering of heparan sulfate chains onto any protein of interest. These novel chimeric molecules, while retaining their endogenous functions, will have enhanced functions provided by the attachment of heparan sulfate chains, and the binding activities specified by them.

There are a number of approaches to creating chimeric peptides that are readily apparent to one skilled in the art. For example by simple recombinant DNA techniques, one can utilize suitable restriction endonuclease sites to ligate the coding regions of two cDNA sequences together in the correct reading frame. These techniques are limited by the presence of suitable restriction cleavage sites and therefore restrict the selection of specific peptide splice junctions.

While certainly not a restriction to the practice of this invention, the inventors find the sequential PCR technique to be a particularly desirable approach. This technique is described in detail in Example 10 above for the purpose of creating site directed mutations. However, in this approach, rather than introducing a site directed mutation, a splice region between two cDNA coding regions are generated.

In brief, for this application pairs of synthetic oligonucleotides are generated that span what will ultimately represent the splice region of the desired fusion protein. These oligos are designed to have the characteristics of 1) spanning the region of the cDNA splice junction 2) one of the oligos contains 3' sequence corresponding to the sense strand of the C-terminal polypeptide 3) the other oligo contains sequence corresponding to the antisense strand of the N-terminal polypeptide, and 4) there is complimentarity between the 5' ends of the two oligonucleotides over a region of from 10–12 nucleotides spanning the splice junction. In the first step, two PCR reactions are performed. One utilizes a sense strand oligo from the 5' untranslated region of the cDNA of the future N-terminal polypeptide (eg. syndecan-1) and the antisense oligo of the complimentary pair with the cDNA for the N-terminal polypeptide as template DNA (eg. syndecan-1). The other reaction utilizes the sense strand oligo of the complimentary pair and an antisense oligo from the 3' untranslated region of the cDNA of the future C-terminal polypeptide (eg. fibronectin) or if a truncation is desired an oligo from within the coding region, into which a stop codon has been introduced. The products of these two PCR reactions are two DNA fragments, encompassing the coding regions from the two polypeptides desired within the final chimera, each containing the desired splice junction of the chimera, and with 10–12 nucleotides of complimentary sequence between the two DNA fragments at the site of the splice junction.

As described above, these fragment are purified away from the original primers, melted and reannealed to one another, and second step PCR reaction carried out using only the two end primers external to the coding region. The resultant fragment corresponds to a cDNA encoding the desired chimera, with the splice junction site specified by the oligonucleotides used in the construction. This splice junction can be manipulated to represent any sequence desirable to the specific application by selection of the appropriate oligonuceotides. (As with all of the examples generated by PCR, DNA sequencing of the resulting construct prior to use is essential to insure that extraneous mutations have not been introduced by the Taq polymerase).

As indicated, this technology can be used for the introduction of heparan sulfate chains (and therefore their specific binding activities) into any protein of interest. One specific example of this technology is in the production of an improved adhesive substratum for cells.

A number of proteins have been characterized from the extracellular matrix of tissues that will support the attachment and growth of cells. One example of such a well characterized protein is fibronectin. Fibronectin is a large adhesive glycoprotein with multiple functional domains. Several of these domains have cell attachment promoting activity. One of these is a single "type-III repeat" which contains a tetrapeptide sequence R-G-D-S, Pierschbacher, M. D., and Ruoslahtl, E., 1984, Nature 309:30–3. Peptides as small as pentapeptides containing these amino acids are able to support cell attachment through a cell surface receptor from the family of integrins, Ruoslahti, E., and Pierschbacher, M. D., 1987, Science, 238:491–497, Pierschbacher, M. D., Ruoslahti, E., 1987 J. Biol. Chem. 262:17,294–8., Hynes, R. O., 1987, Cell 48:549–54 and Hynes, R. O., 1992, Cell 69:11–25.

Several companies have commercialized products based on this cell attachment sequence for use as reagents in cell culture and various biomaterials applications. See for example recent catalogs from Telios Pharmaceutical, BRL, Stratagene, Protein Polymer Technologies etc., as well as U.S. Pat. Nos. 4,517,686; 4,589,881; 4,578,079; 4,614,517; 4,661,111; 4,792,525.

In one specific example of this invention oligonucelotides may be selected using the criterion described above and utilized by the sequential PCR method to generate a chimera between murine syndecan-1 residues 1–81 and the 10th Type III repeat of human fibronectin Kornblihtt, A. R., et al., 1985, EMBO, 4:1755–9. A primary formula for such a chimera would be as follows:

```
M-R-R-A-A-L-W-L-W-L-C-A-L-A-L-R-L-Q-P-A-L-P-Q-I-V-A-V-N-V-P-  (SEQ ID NO: 34)
P-E-D-Q-D-G-S-G-D-D-S-D-N-F-S-G-S-G-T-G-A-L-P-D-T-L-S-R-Q-T-
P-S-T-W-K-D-V-W-L-L-T-A-T-P-T-A-P-E-P-T-S-V-S-D-V-P-R-D-L-E-
V-V-A-A-T-P-T-S-L-L-I-S-W-D-A-P-A-V-T-V-R-Y-Y-R-I-T-Y-G-E-T-
G-G-N-S-P-V-Q-E-F-T-V-P-G-S-K-S-T-A-T-I-S-G-L-K-P-G-V-D-Y-T-
I-T-V-Y-A-V-T-G-R-G-D-S-P-A-S-S-K-P-I-S-I-N-Y-R-T
```

This cDNA, when expressed in cell containing the proper machinery for heparan sulfate synthesis (as describe elsewhere in this document) will produce large quantities of a novel peptide containing the RGDS cell attachment activity as well as new binding activities specified by the addition of functional heparan sulfate chains. These heparan sulfate chains will allow stabilization and activation of culture media growth factors near the surfaces of cells newly adherent to the substratum, thus improving its general utility. This is especially true for primary cells or cell lines that may otherwise be rather fastidious in their growth.

The above example describes a chimera containing amino acid residues 1–81 of murine syndecan-1 spliced to the N-terminus of a specifies portion of the coding region of human fibronectin. Several modifications of the above example are allowable, and will be readily understood by one skilled in the art. These modifications include but are not restricted to; the use of other suitable signal peptides, inclusion of other sequences from the heparan sulfate attachment region, use of other species of syndecan-1 including human, use of other novel heparan sulfate attachment sequences derived from combinatorial analysis as outlined elsewhere in this document, insertion of "linker" peptide sequences, use of smaller or larger regions of human fibronectin to include other functional domains and movement of the heparan sulfate attachment sequence to the C-terminal end of the chimera. Furthermore, while fibronectin has been illustrated as a specific example of this technology, its application to other extracellular matrix proteins, as well as synthetic polymers with cell attachment activity is anticipated by its example.

EXAMPLE 12

Syndecan-Growth Factor Chimera

A number of growth factors have been characterized by virtue of their binding interactions with heparin and heparan sulfate. An incomplete list of these heparin binding growth factors includes: bFGF (basic fibroblast growth factor), aFGF (acidic fibroblast growth factor, KGF, hst/K-fgf, int-2, haparin binding EGF, hepatocyte growth factor, interferon γ, platelet-derived growth factor, VEGF (vasular endothelial growth factor), schwannoma-derived growth factor. In each case, heparin/heparan sulfate interaction with these growth factors have been demonstrated to modify growth factor activity through either stabilization and/or facilitation of binding to the high affinity receptor for the growth factor.

The clinical applications of all of these growth factors are suitable candidates for improvement by the technology of this invention. The uses of this technology with respect to therapeutic applications of basic fibroblast growth factor (bFGF) will be described here. The application of this technology to the other heparin binding growth factors can be understood by example.

bFGF is a chemically and thermally unstable growth factor reducing its therapeutic utility. These instabilities are partially mitigated by interactions with heparin or heparan sulfate which tend to stabilize this molecule. Binding of bFGF to heparan sulfate is not merely coincidence. Indeed, it has been well established that binding of bFGF to heparan sulfate at the cell surface is essential for functional interaction of bFGF with its high affinity (signal transducing) receptor, See Yayn, A. et al. (1991), Cell 64:841–8.

bFGF has a wide range of biological activities in vivo, including mitogenesis and chemotaxis. For example, bFGF has mitogenic activity for cells such as keratinocytes, fibroblasts, endothelial cells, smooth muscle cells, chondrocytes, osteoblasts, preadipocytes as well as melanocytes and other neuroectodermally derived cells. These mitogenic activities of bFGF have suggested, among other applications, utility in would healing. Indeed, that intrinsic bFGF participates in wound healing has been demonstrated by studies showing that monospecific neutralizing bFGF antibodies delay wound healing (Broadley, K. N. et al. 1989. Lab. Invest. 61:571–575). This has lead to a number of preclinical trials of therapeutically administered bFGF in wound-healing models. Particularily, its application has been explored in delayed wound-healing models, such as infected wounds, decubitous ulcers, diabetic ulcers, as well as traumatic wounds in individuals with impaired healing abilities such as diabetic and cancer patients. These studies reveal accelerated healing of wounds treated with topical bFGF. See for example, Hayward, P., et al., 1992., Am. J. Surg. 163: 288–93., Fiddes, J. C. et al. 1991. The Fibroblast Growth Factors, Eds. Balrd. A., and Klagsbrun, M., Annals of The New York Academy of Sciences, Vol. 638. p 316–328., Greenhaigh, D. G., et al., 1990, Am. J. Pathol. 136:1235–46, Tsubol, R., and Rifkin, D. B., 1990, J. Exp. Med., 172: 245–51.

An important aspect of this work is the recognition of greatly enhanced bFGF effects in wound healing, particularly with respect to wound strength, when administered via a delayed delivery system. See Slavin, J. et al., 1992, Br. J. Surg., 1992, 79:918–21. This mode of administration introduces particular problems with insuring the proper stabilization of bFGF activity. The problems with bFGF instability and inactivation in wound therapy, even in single dose administration, are well characterized by Finetti, G., and Farina, M., 1992., Farmaco, 47:967–78.

The technology disclosed in this invention allow, by molecular genetic techniques, the construction of chimeric bFGF cDNAs that contain the heparan sulfate attachment sequence. Expression of these cDNAs in cells containing the proper machinery for heparan sulfate sythesis (mammalian, insect etc.) will allow the preparation of new chimeric bFGF molecules containing heparan sulfate chains.

Heparan sulfate containing bFGF molecules have several improved biological properties. First, interaction between the heparan sulfate chains and the heparin binding region of the bFGF portion of the chimera (both inter and intramolecularily) will stabilize the bFGF molecule against inactivation, thus improving its utility especially in delayed delivery systems. Second, as indicated above, the interaction between heparan sulfate and the bFGF polypeptide is essential for binding to the high affinity receptor and signal transduction. Thus, the chimeric heparan sulfate bFGF will have increased bioactivity with respect to native bFGF. Third, the presence of heparan sulfate in wounds has other desirable effects. Transforming growth factor beta (TGF-β), has been shown to enhance bFGF wound-healing by stimulating collagen synthesis so as to result in increased wound tensile strength, Slavin, J., et al., 1992, Br. J. Surg., 79:69–72. Heparin/heparan sulfate potentiates the effect of TGF-β by dissociating this growth factor from its inactive complex with alpha 2-macroglobulin McCaffrey, T. A., 1989, J. Cell Biol. 109:441–8.

As indicated eleswhere, cDNAs encoding chimeric proteins can be created by a number of molecular biological techniques. However, our preferred techniques the sequential PCR technique described in detail in the above examples. For the preparation of a heparan sulfate attachment sequence-bFGF chimera an example of four useful oligonucleotides are provided:

```
#177  A-T-G-T-C-G-A-C-T-G-C-A-A-C-C-G-G-C-A-A-   (SEQ ID NO: 35)
      C-T-C-G-G-A-T-C-C-A

#228  G-G-C-T-G-C-G-C-T-G-G-T-G-G-C-T-C-T-G-     (SEQ ID NO: 36)
      G-A-G-C

#229  A-C-C-A-G-C-G-C-A-G-C-C-G-G-G-A-G-C-A-T-   (SEQ ID NO: 37)
      C-A-C-C-

#206  G-G-C-T-C-G-A-G-A-A-G-C-T-T-C-A-C-T-G-G-   (SEQ ID NO: 38)
      G-T-A-A-C
```

As described above, there are two first step PCR reaction, one uses oligos #177 and #228 with murine syndecan-1 cDNA as the template, and the other reaction using oligos #229 and #206 with a human bFGF cDNA as the template (Kurokawa, T., et al., 1987., FEBS Lett. 213:189–94). After purification and annealing of the two resultant fragments, as described, a second PCR reaction is carried out utilizing the oligos #177 and #206 only as primers. The PCR reaction conditions are identical to those described above in the previous examples. The oligos #177 and #206 given in this example have been selected to insure SalI and HindIII restriction sites on the ends of the cDNA to allow subcloning into the described mammalian expression vector pH β APr-1. One skilled in the art could substitute other oligonucleotides to allow cloning into other desirable vectors.

A cDNA has been produced by these techniques that encodes a chimeric protein of the following amino acid sequence:

```
M-R-R-A-A-L-W-L-W-L-C-A-L-A-L-R-L-Q-P-A-L-P-Q-I-V-A-V-   (SEQ ID NO: 39)
N-V-P-P-E-D-Q-D-G-S-G-D-D-S-D-N-F-S-G-S-G-T-G-A-L-P-D-T-L-S-
R-Q-T-P-S-T-W-K-D-V-W-L-L-T-A-T-P-T-A-P-E-P-T-S-A-A-G-S-I-T-
T-L-P-A-L-P-E-D-G-G-S-G-A-F-P-P-G-H-F-K-D-P-K-R-L-Y-C-K-N-G-
G-F-F-L-R-I-H-P-D-G-R-V-D-G-V-R-E-K-S-D-P-H-I-K-L-Q-L-Q-A-E-
E-R-G-V-V-S-I-K-G-V-C-A-N-R-Y-L-A-M-K-E-D-G-R-L-L-A-S-K-C-V-
T-D-E-C-F-F-F-E-R-L-E-S-N-N-Y-N-T-Y-R-S-R-K-Y-T-S-W-Y-V-A-L-
K-R-T-G-Q-Y-K-L-G-S-K-T-G-P-G-Q-K-A-I-L-F-L-P-M-S-A-K-S
```

The above example describes a chimera containing amino acid residues 1–81 of murine syndecan-1 spliced to the N-terminus of the coding region of human bFGF. Several modifications of the above example are allowable, and will be readily understood by one skilled in the art. These modifications include but are not restricted to; the use of other suitable signal peptides, inclusion of other sequences from the heparan sulfate attachment region, use of other species of syndecan-1 including human, use of other novel heparan sulfate attachment sequences derived from combinatorial analysis as outlined elsewhere in this document, insertion of "linker" peptide sequences, and movement of the heparan sulfate attachment sequence to the C-terminal end of the chimera.

That bFGF will allow substantial modification in the way of added chimeric sequences, without destroying its mitogenic activity, has been well demonstrated by Prieto, I., et al., 1991. The Fibroblast Growth Factors, Eds. Baird, A., and Klagsbrun, M., Annals of The New York Academy of Sciences, Vol. 638. p 434–7. These investigators have created a chimera consisting of bFGF with 252 amino acid residues of the ribosomal inactivating protein, saporin toxin, added to the C-terminus. This chimera retains both bFGF mitogenic activity, as well as the saporin toxic activity. The fusion has been used to target killing of cells expressing the high affinity receptor for bFGF (an activity which as an aside also could be enhanced by application of this invention).

The heparan sulfate attachment sequence-bFGF chimera described here is only one example of such growth factor chimeras. One skilled in the art will recognized the ability to equivalently substitute any of the heparin binding growth factors in these formulations, with similar enhancement of their specific therapeutic applications based on their individual mitogenic activities.

EXAMPLE 13

Syndecan-Growth Factor Receptor Chimeras

The ability to add heparan sulfate chains to other macromolecules by the use of this invention has been demonstrated by several examples. In particular, several examples have been illustrated involving the activation and stabilization of various heparin binding growth factors. In some clinical situations, the inhibition of these growth factor activities are particularity desirable. For example inhibition of HB-EGF (heparin binding EGF) mitogenic activity for smooth muscle cells in atherosclerosis and inhibition of VEGF (vascular endotheial growth factor) in preventing neovascularization of tumors.

The fact that the "high affinity" receptors for these growth factors require heparan sulfate for high affinity binding of the growth factor can be exploited in the generation of growth factor antagonists. For example, using the technology of this invention, one can genetically engineer heparan sulfate chains onto truncated polypeptides comprising the active binding site of a high affinity receptor for one of the heparin binding growth factors. These chimeras will represent highly activated receptor analogs and therefor serve as potent competitors in the binding of their respective heparin binding growth factor ligands.

Binding of growth factor by these high affinity "mock receptors" will result in the sequestration of a specific heparin binding growth factor, ultimately resulting in its elimination. Further modifications may be introduced to these "mock receptor" if desired to regulate there biological half-life, and therefore the rate of turnover of the growth factor in question.

EXAMPLE 14

Identification of Functional Heparan Sulfate Attachment Sequences

A combinatorial library of syndecan-1 homologs comprising varied heparan sulfate attachment sequences represented by the general formula Asp-Xaa(1)-Xaa(2)-Xaa(3)-Xaa(4)-Xaa(5)-Ser-Gly-Ser-Gly (SEQ ID NO: 13), where Xaa(1)=Asn, Asp, Ile or an amino acid gap; Xaa(2)=Phe or Tyr; Xaa(3)=Glu, Ser, Ala or an amino acid gap; Xaa(4)= Leu, Gly, Ser or an amino acid gap; and Xaa(5)=Ala, Gly or an amino acid gap, can be created using the degenerate oligonucleotide

```
                Xaa1 Xaa2 Xaa3 Xaa4 Xaa5
GATGACTCTGAC    RWC  TWC  RVW  VKT  GST   TCTGGCTCTGGCACA    (SEQ ID NO: 40)
``` where each of the codons corresponding to Xaa(1)–Xaa(5) can be absent (e.g. to create amino acid gaps in the corresponding degenerate peptide).

Using oligonucleotide primer No.70 (Example 9) and the primer AGAGTCAT-CCCCAGA (SEQ ID NO: 41), the DNA sequences encoding Met-1 through Ser-41 of syndecan-1 (SEQ ID NO: 1), as well as a portion of the 5' non-coding sequence of the cloned gene can be amplified by PCR and isolated. Likewise, the nucleotide sequence corresponding to Thr-49 through Ala-311 and the 3' non-coding region of the syndecan-1 gene can be amplified using the primers ACAGGTGCTTTGCCA (SEQ ID NO: 42) and GCCGAAAG-TTTATTACATCTG (SEQ ID NO: 43).

The purified 5' and 3' amplimers of the syndecan-1 gene are then mixed with the degenerate oligonucleotide under conditions which facilitate annealing of the invariant portions of the oligonucleotide with the complementary sequences in the 5' and 3' amplimers. The single-stranded regions of the annealed product are filled in with polymerase, and nicks closed by the action of a ligase. The full length degenerate gene can be separated from the remaining amplimer fragments by virtue of its difference in size. The isolated degenerate gene is then treated with HindIII and BamHI, and ligated into the pHβ APr-1 vector described in Example 9. The resulting degenerate vector is then used to transfect WI-L2-729HF$_2$ cells (ATCC CRL 8062), or a cell similar thereto which is unable to bind bFGF.

As described by Kiefer et al. (1990) *PNAS* 87:6985, tissue culture dishes (eg. Falcon 3003) are incubated overnight a 4° C. with recombinant human bFGF (30 μg/ml in water). The dishes are then aspirated, rinsed with isotonic phosphate-buffered saline (PBS), and then blocked by incubation (1 hr, 25° C.) with FBS/2% (vol/vol) FCS. The transfected cells are grown in normal culture media for 48 hours, then isolated in PBS/2% FCS and applied to the bFGF coated dishes and allowed to attach for 3 minutes at 25° C. The dishes are then washed with PBS. The panning process can be repeated, with optional expansion of bound cells by intermediate addition and incubation with selective medium. The sequence of the heparan sulfate attachment site can be determined by standard DNA isolation and sequencing techniques for each of the variants which produce a transfected cell capable of binding bFGF.

All publications and patent applications cited in this specification are herein incorporated by reference as if each individual publication or patent application were specifically and individually indicated to be incorporated by reference.

EQUIVALENTS

Those skilled in the art will recognize, or be able to ascertain using no more than routine experimentation, numerous equivalents to the specific proteins and methods described herein. Such equivalents are considered to be within the scope of this invention and are covered by the following claims.

---

What is claimed is:

1. A fusion protein comprising, a first polypeptide portion having an amino acid sequence from a syndecan protein comprising amino acids 20–41 of SEQ ID NO: 9, with a functional heparan sulphate attachment sequence having the amino acid sequence Xac-Z-Ser-Gly-Ser-Gly (SEQ ID NO: 44), wherein Xac represents an amino acid residue having an acidic sidechain, and Z represents from 1 to 10 amino acid residues, or amino acids 20–41 of SEQ ID NO: 9 with at least one conservative amino acid substitution occurring outside of the functional heparan sulphate attachment sequence, wherein the heparan sulphate attachment sequence has a heparan sulfate glycosaminoglycan chain attached thereto, and a second polypeptide portion having an amino acid sequence from a protein which does not naturally have a covalently linked heparan sulphate glycosaminoglycan chain, and wherein the heparan sulphate glycosaminoglycan chain attached to the first polypeptide portion modifies the function of the second polypeptide portion.

2. The fusion protein of claim 1, wherein the first polypeptide portion has an amino acid sequence that is at least 50% identical to amino acids 20–41 of SEQ ID NO: 9.

3. The fusion protein of claim 1, further comprising at least one chondroitin sulfate glycosaminoglycan.

4. The fusion protein of claim 1, wherein the second polypeptide is a growth factor selected from the group consisting of heparan-binding growth factor (HBGF), acidic FGF (aFGF) basic fibroblast growth factor (bFGF), keratinocyte growth factor (KGF), granulocyte-macrophage colony stimulating factor (GMCSF), Int-2, hst/k-fgf, and FGF-5, FGF-6, hepatocyte growth factor (HGF), heparan-binding EGF-like growth factor (HB-EGF), platelet-derived growth factor (PDGF), transforming growth factor-β (TGF-β), vascular endothelial growth factor (VEGF), vascular permeability factor (VPF), hepatocyte growth factor, interferon γ, interleukin-3, and Schwannoma-derived growth factor (SDGF).

5. The fusion protein of claim 4, wherein the second polypeptide is basic fibroblast growth factor (bFGF).

6. The fusion protein of claim 1, wherein the second polypeptide is growth factor receptor.

7. The fusion protein of claim 1, wherein the second polypeptide is an extracellular matrix molecule selected from the group consisting of collagen type I, collagen type II, collagen type III, collagen type V, laminin, vitronectin, tenascin, thrombospondin, pleitropin, entactin, SPARC, wnt-1 and fibronectin.

8. The fusion protein of claim 1, wherein the second polypeptide is a protease inhibitor selected from the group consisting of thrombin, antithrombin III, heparan cofactor II, leuserpin, plasminogen activator inhibitor, tissue plasminogen activator, lipoprotein-associated coagulation inhibitor, protein nexin I, factor $X_a$, lipoprotein assocaited coagulation inhibitor (LACI).

9. The fusion protein of claim 8, wherein the second polypeptide is antithrombin III.

10. The fusion protein of claim 1, wherein the second polypeptide is a degradative enzyme selected from the group consisting of acetylcholinesterase, extracellular superoxide dismutase, thrombin, and tissue plasminogen activator.

11. The fusion protein of claim 1, wherein the second polypeptide is a lipoliytic enzyme selected from the group consisting of cholesterol esterase, triglyceride lipases, lipoprotein lipase apolipoprotein B (apoB) and apoprotein E (apoE).

12. The fusion protein of claim 1, wherein the second polypeptide is a cell adhesion molecule selected from the group consisting of neural cell adhesion molecule (N-CAM) and platelet endothelium cell adhesion molecule (PECAM).

13. The fusion protein of claim 1, wherein the second polypeptide is a nuclear protein selected from the group consisting of c-fos, c-jun. RNA polymerases, and DNA polymerases.

14. The fusion protein of claim 1, wherein the second polypeptide is a microbial pathogen selected from the group consisting of glycoprotein C (gC) of herpes simplex virus I, glycoprotein B (gB) of herpes simplex virus II, glycoprotein C (gC) of herpes simplex virus II, glycoprotein B (gB) of herpes simplex virus II, glycoprotein C II (gC-II) of cytomegato virus, glycoprotein 120 (gp-120) of human immunodeficiency virus, circumsporozoite protein of *Plasmodium falciparum*, adhesion protein of *Trypanosoma gondii*, adhesion protein of *Bordetella pertussis*, adhesion protein of *Streptococcus pyogenes* and adhesion protein of *Staphylococcus aureous*.

15. The fusion protein of claim 1, wherein the heparan sulfate chain modifies the function of the second polypeptide by influencing at least one of the binding affinity, binding specificity, and stability of the second polypeptide.

16. The fusion protein of claim 1, wherein the first polypeptide portion comprises amino acids 20–41 of SEQ ID NO: 9.

* * * * *

SEQUENCE LISTING

```
<160> NUMBER OF SEQ ID NOS: 46

<210> SEQ ID NO 1
<211> LENGTH: 2432
<212> TYPE: DNA
<213> ORGANISM: MUS SP

<400> SEQUENCE: 1
actccgcggg agaggtgcgg gccagaggag acagagccta acgcagagga agggacctgg      60
cagtcgggag ctgactccag ccggcgaaac ctacagccct cgctcgagag agcagcgagc     120
tgggcaggag cctgggacag caaagcgcag agcaatcagc agagccggcc cggagctccg     180
tgcaaccggc aactcggatc cacgaagccc accgagctcc cgccgccggt ctgggcagca     240
tgagacgcgc ggcgctctgg ctctggctct gcgcgctggc gctgcgcctg cagcctgccc     300
tcccgcaaat tgtggctgta aatgttcctc ctgaagatca ggatggctct ggggatgact     360
ctgacaactt ctctggctct ggcacaggtg ctttgccaga tactttgtca cggcagacac     420
cttccacttg gaaggacgtg tggctgttga cagccacgcc cacagctcca gagcccacca     480
gcagcaacac cgagactgct tttacctctg tcctgccagc cggagagaag cccgaggagg     540
gagagcctgt gctccatgta gaagcagagc ctggcttcac tgctcgggac aaggaaaagg     600
aggtcaccac caggcccagg gagaccgtgc agctccccat cacccaacgg gcctcaacag     660
tcagagtcac cacagcccag gcagctgtca catctcatcc gcacgggggc atgcaacctg     720
```

-continued

```
gcctccatga gacctcggct cccacagcac ctggtcaacc tgaccatcag cctccacgtg    780
tggagggtgg cggcacttct gtcatcaaag aggttgtcga ggatggaact gccaatcagc    840
ttcccgcagg agagggctct ggagaacaag acttcacctt tgaaacatct ggggagaaca    900
cagctgtggc tgccgtagag cccggcctgc ggaatcagcc cccggtggac gaaggagcca    960
caggtgcttc tcagagcctt ttggacagga aggaagtgct gggaggtgtc attgccggag   1020
gcctagtggg cctcatcttt gctgtgtgcc tggtggcttt catgctgtac cggatgaaga   1080
agaaggacga aggcagctac tccttggagg agcccaaaca agccaatggc ggtgcctacc   1140
agaaacccac caagcaggag gagttctacg cctgatgggg aaatagttct ttctcccccc   1200
cacagcccct gccactcact aggctcccac ttgcctcttc tgtgaaaaac ttcaagccct   1260
ggcctcccca ccactgggtc atgtcctctg cacccaggcc cttccagctg ttcctgcccg   1320
agcggtccca gggtgtgctg ggaactgatt cccctccttt gacttctgcc tagaagcttg   1380
ggtgcaaagg gtttcttgca tctgatcttt ctaccacaac cacacctgtc gtccactctt   1440
ctgacttggt ttctccaaat gggaggagac ccagctctgg acagaaaggg acccgactg    1500
cttttggacct agatggccta ttgcggctgg aggatcctga ggacaggaga ggggcttcgg   1560
ctgaccagcc atagcactta cccatagaga ccgctagggt tggccgtgct gtggtggggg   1620
atggaggcct gagctccttg gaatccactt ttcattgtgg ggaggtctac tttagacaac   1680
ttggttttgc acatattttc tctaatttct ctgttcagag ccccagcaga ccttattact   1740
ggggtaaggc aagtctgttg actggtgtcc ctcacctcgc ttccctaatc tacattcagg   1800
agaccgaatc gggggttaat aagacttttt ttgttttttg tttttgtttt taacctagaa   1860
gaaccaaatc tggacgccaa aacgtaggct tagtttgtgt gttgtctctg agtttgtgct   1920
catgcgtaca acagggtatg gactatctgt atggtgcccc attttttggcg gcccgtaagt   1980
aggctaggct agtccaggat actgtggaat agccacctct tgaccagtca tgcctgtgtg   2040
catggactca gggccacggc cttggcctgg gccaccgtga cattggaaga gcctgtgtga   2100
gaacttactc gaagttcaca gtctaggagt ggaggggagg agactgtaga gttttggggg   2160
aggggtagca agggtgccca agcgtctccc acctttggta ccatctctag tcatccttcc   2220
tcccggaagt tgacaagaca catcttgagt atggctggca ctggttcctc catcaagaac   2280
caagttcacc ttcagctcct gtggccccgc cccaggctg gagtcagaaa tgtttcccaa   2340
agagtgagtc ttttgctttt ggcaaaacgc tacttaatcc aatgggttct gtacagtaga   2400
ttttgcagat gtaataaact ttaatataaa gg                                 2432
```

<210> SEQ ID NO 2
<211> LENGTH: 311
<212> TYPE: PRT
<213> ORGANISM: MUS SP

<400> SEQUENCE: 2

```
Met Arg Arg Ala Ala Leu Trp Leu Trp Leu Cys Ala Leu Ala Leu Arg
1               5                   10                  15

Leu Gln Pro Ala Leu Pro Gln Ile Val Ala Val Asn Val Pro Pro Glu
                20                  25                  30

Asp Gln Asp Gly Ser Gly Asp Asp Ser Asp Asn Phe Ser Gly Ser Gly
            35                  40                  45

Thr Gly Ala Leu Pro Asp Thr Leu Ser Arg Gln Thr Pro Ser Thr Trp
        50                  55                  60
```

```
Lys Asp Val Trp Leu Leu Thr Ala Thr Pro Thr Ala Pro Glu Pro Thr
 65                  70                  75                  80

Ser Ser Asn Thr Glu Thr Ala Phe Thr Ser Val Leu Pro Ala Gly Glu
                 85                  90                  95

Lys Pro Glu Glu Gly Glu Pro Val Leu His Val Glu Ala Glu Pro Gly
            100                 105                 110

Phe Thr Ala Arg Asp Lys Glu Lys Glu Val Thr Thr Arg Pro Arg Glu
            115                 120                 125

Thr Val Gln Leu Pro Ile Thr Gln Arg Ala Ser Thr Val Arg Val Thr
            130                 135                 140

Thr Ala Gln Ala Ala Val Thr Ser His Pro His Gly Gly Met Gln Pro
145                 150                 155                 160

Gly Leu His Glu Thr Ser Ala Pro Thr Ala Pro Gly Gln Pro Asp His
                165                 170                 175

Gln Pro Pro Arg Val Glu Gly Gly Thr Ser Val Ile Lys Glu Val
            180                 185                 190

Val Glu Asp Gly Thr Ala Asn Gln Leu Pro Ala Gly Glu Gly Ser Gly
            195                 200                 205

Glu Gln Asp Phe Thr Phe Glu Thr Ser Gly Glu Asn Thr Ala Val Ala
            210                 215                 220

Ala Val Glu Pro Gly Leu Arg Asn Gln Pro Pro Val Asp Glu Gly Ala
225                 230                 235                 240

Thr Gly Ala Ser Gln Ser Leu Leu Asp Arg Lys Glu Val Leu Gly Gly
                245                 250                 255

Val Ile Ala Gly Gly Leu Val Gly Leu Ile Phe Ala Val Cys Leu Val
                260                 265                 270

Ala Phe Met Leu Tyr Arg Met Lys Lys Lys Asp Glu Gly Ser Tyr Ser
                275                 280                 285

Leu Glu Glu Pro Lys Gln Ala Asn Gly Gly Ala Tyr Gln Lys Pro Thr
            290                 295                 300

Lys Gln Glu Glu Phe Tyr Ala
305                 310

<210> SEQ ID NO 3
<211> LENGTH: 310
<212> TYPE: PRT
<213> ORGANISM: HOMO SAPIENS

<400> SEQUENCE: 3

Met Arg Arg Ala Ala Leu Trp Leu Trp Leu Cys Ala Leu Ala Leu Ser
  1               5                  10                  15

Leu Gln Leu Ala Leu Pro Gln Ile Val Ala Thr Asn Ile Pro Pro Glu
                 20                  25                  30

Asp Gln Asp Gly Ser Gly Asp Asp Ser Asp Asn Phe Ser Gly Ser Gly
             35                  40                  45

Ala Gly Ala Leu Gln Asp Ile Thr Leu Ser Gln Gln Thr Pro Ser Thr
         50                  55                  60

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
                 85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
            115                 120                 125
```

-continued

```
Thr Gln Leu Pro Thr Thr His Gln Ala Ser Thr Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Pro Ser Ala Thr Glu Arg Ala Ala
            180                 185                 190

Glu Asp Gly Ala Ser Ser Gln Leu Pro Ala Ala Glu Gly Ser Gly Glu
            195                 200                 205

Gln Asp Phe Thr Phe Glu Thr Ser Gly Glu Asn Thr Ala Val Val Ala
        210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 4
<211> LENGTH: 313
<212> TYPE: PRT
<213> ORGANISM: RATTUS RATTUS

<400> SEQUENCE: 4

Met Arg Arg Ala Ala Leu Trp Leu Trp Leu Cys Ala Leu Ala Leu Arg
1               5                   10                  15

Leu Gln Pro Ala Leu Pro Gln Ile Val Thr Ala Asn Val Pro Pro Glu
            20                  25                  30

Asp Gln Asp Gly Ser Gly Asp Asp Ser Asp Asn Phe Ser Gly Ser Gly
        35                  40                  45

Thr Gly Ala Leu Pro Asp Met Thr Leu Ser Arg Gln Thr Pro Ser Thr
    50                  55                  60

Trp Lys Asp Val Trp Leu Leu Thr Ala Thr Pro Ala Pro Glu Pro
65                  70                  75                  80

Thr Ser Arg Asp Thr Glu Ala Thr Leu Thr Ser Ile Leu Pro Ala Gly
                85                  90                  95

Glu Lys Pro Glu Glu Gly Glu Pro Val Ala His Val Glu Ala Glu Pro
            100                 105                 110

Asp Phe Thr Ala Arg Asp Lys Glu Lys Glu Ala Thr Thr Arg Pro Arg
        115                 120                 125

Glu Thr Thr Gln Leu Pro Val Thr Gln Gln Ala Ser Thr Ala Ala Arg
    130                 135                 140

Ala Thr Thr Ala Gln Ala Ser Val Thr Ser His Pro His Gly Asp Val
145                 150                 155                 160

Gln Pro Gly Leu His Glu Thr Leu Ala Pro Thr Ala Pro Gly Gln Pro
                165                 170                 175

Asp His Gln Pro Pro Ser Val Glu Asp Gly Gly Thr Ser Val Ile Lys
```

```
                 180                 185                 190
Glu Val Val Glu Asp Glu Thr Thr Asn Gln Leu Pro Ala Gly Glu Gly
            195                 200                 205

Ser Gly Glu Gln Asp Phe Thr Phe Glu Thr Ser Gly Glu Asn Thr Ala
        210                 215                 220

Val Ala Gly Val Glu Pro Asp Leu Arg Asn Gln Ser Pro Val Asp Glu
225                 230                 235                 240

Gly Ala Thr Gly Ala Ser Gln Gly Leu Leu Asp Arg Lys Glu Val Leu
                245                 250                 255

Gly Gly Val Ile Ala Gly Gly Leu Val Gly Leu Ile Phe Ala Val Cys
            260                 265                 270

Leu Val Ala Phe Met Leu Tyr Arg Met Lys Lys Lys Asp Glu Gly Ser
        275                 280                 285

Tyr Ser Leu Glu Glu Pro Lys Gln Ala Asn Gly Gly Ala Tyr Gln Lys
    290                 295                 300

Pro Thr Lys Gln Glu Glu Phe Tyr Ala
305                 310

<210> SEQ ID NO 5
<211> LENGTH: 309
<212> TYPE: PRT
<213> ORGANISM: HAMSTER SP

<400> SEQUENCE: 5

Met Arg Arg Ala Ala Leu Trp Leu Trp Leu Cys Ala Leu Ala Leu Arg
1               5                   10                  15

Leu Gln Pro Val Leu Pro Gln Ile Val Thr Asn Val Pro Pro Glu
            20                  25                  30

Asp Gln Asp Gly Ser Gly Asp Asp Ser Asp Asn Phe Ser Gly Ser Gly
        35                  40                  45

Thr Gly Ala Leu Pro Asp Ile Thr Leu Ser Arg Gln Ala Ser Pro Thr
    50                  55                  60

Leu Lys Asp Val Trp Leu Leu Thr Ala Thr Pro Thr Ala Pro Glu Pro
65                  70                  75                  80

Thr Ser Arg Asp Ala Gln Ala Thr Thr Thr Ser Ile Leu Pro Ala Ala
                85                  90                  95

Glu Lys Pro Gly Glu Gly Glu Pro Val Leu Thr Ala Glu Val Asp Pro
            100                 105                 110

Gly Phe Thr Ala Arg Asp Lys Glu Ser Glu Val Thr Thr Arg Pro Arg
        115                 120                 125

Glu Thr Thr Gln Leu Leu Ile Thr His Trp Val Ser Thr Ala Arg Ala
    130                 135                 140

Thr Thr Ala Gln Ala Pro Val Thr Ser His Pro His Arg Asp Val Gln
145                 150                 155                 160

Pro Gly Leu His Glu Thr Ser Ala Pro Thr Ala Pro Gly Gln Pro Asp
                165                 170                 175

Gln Gln Pro Pro Ser Gly Gly Thr Ser Val Ile Lys Glu Val Ala Glu
            180                 185                 190

Asp Gly Ala Thr Asn Gln Leu Pro Thr Gly Glu Gly Ser Gly Glu Gln
        195                 200                 205

Asp Phe Thr Phe Glu Thr Ser Gly Glu Asn Thr Ala Val Ala Ala Val
    210                 215                 220

Glu Pro Asp Gln Arg Asn Gln Pro Pro Val Asp Glu Gly Ala Thr Gly
225                 230                 235                 240
```

-continued

```
Ala Ser Gln Gly Leu Leu Asp Arg Lys Glu Val Gly Gly Val Ile
            245                 250                 255

Ala Gly Gly Leu Val Gly Leu Ile Phe Ala Val Cys Leu Val Gly Phe
            260                 265                 270

Met Leu Tyr Arg Met Lys Lys Asp Glu Gly Ser Tyr Ser Leu Glu
            275                 280                 285

Glu Pro Lys Gln Ala Asn Gly Gly Ala Tyr Gln Lys Pro Thr Lys Gln
            290                 295                 300

Glu Glu Phe Tyr Ala
305

<210> SEQ ID NO 6
<211> LENGTH: 125
<212> TYPE: PRT
<213> ORGANISM: HOMO SAPIEN

<400> SEQUENCE: 6

Glu Ser Leu Arg Glu Thr Glu Val Ile Asp Pro Gln Asp Leu Leu Glu
1               5                   10                  15

Gly Arg Tyr Phe Ser Gly Ala Leu Pro Asp Asp Glu Asp Val Val Gly
            20                  25                  30

Pro Gly Gln Glu Ser Asp Asp Phe Glu Leu Ser Gly Ser Gly Asp Leu
        35                  40                  45

Asp Asp Leu Glu Asp Ser Met Ile Gly Pro Glu Val Val His Pro Leu
    50                  55                  60

Val Pro Leu Asp Asn His Ile Pro Glu Arg Ala Gly Ser Gly Ser Gln
65                  70                  75                  80

Val Pro Thr Glu Pro Lys Lys Leu Glu Glu Asn Glu Val Ile Pro Lys
                85                  90                  95

Arg Ile Ser Pro Val Glu Glu Ser Glu Asp Val Ser Asn Lys Val Ser
            100                 105                 110

Met Ser Ser Thr Val Gln Gly Ser Asn Ile Phe Glu Arg
            115                 120                 125

<210> SEQ ID NO 7
<211> LENGTH: 44
<212> TYPE: PRT
<213> ORGANISM: RATTUS RATTUS

<400> SEQUENCE: 7

Tyr Phe Ser Gly Ala Leu Pro Asp Asp Glu Asp Ala Gly Gly Leu Glu
1               5                   10                  15

Gln Asp Ser Asp Phe Glu Leu Ser Gly Ser Gly Asp Leu Asp Asp Thr
            20                  25                  30

Glu Glu Pro Arg Thr Phe Pro Glu Val Ile Ser Pro
            35                  40

<210> SEQ ID NO 8
<211> LENGTH: 357
<212> TYPE: PRT
<213> ORGANISM: HAMSTER SP

<400> SEQUENCE: 8

Pro Arg Ala Leu Leu Ser Arg Pro Cys Gly Thr Lys Met Pro Ala Gln
1               5                   10                  15

Leu Arg Gly Ile Ala Val Leu Leu Leu Leu Ser Ala Arg Ala Ala
            20                  25                  30

Leu Ala Gln Pro Trp Arg Asn Glu Asn Tyr Glu Arg Pro Val Asp Leu
```

-continued

```
                35                  40                  45
Glu Gly Ser Gly Asp Asp Pro Phe Gly Asp Glu Leu Asp Asp
        50                  55                  60
Ala Tyr Ser Gly Ser Gly Ser Gly Tyr Phe Glu Gln Glu Ser Gly Leu
65                  70                  75                  80
Glu Thr Ala Val Ser Leu Thr Asp Thr Ser Val Pro Leu Pro Thr
                85                  90                  95
Thr Val Ala Val Leu Pro Val Thr Leu Val Gln Pro Met Ala Thr Pro
                100                 105                 110
Phe Glu Leu Phe Pro Thr Glu Asp Thr Ser Pro Glu Gln Thr Thr Ser
            115                 120                 125
Val Leu Tyr Ile Pro Lys Ile Thr Glu Ala Pro Val Ile Pro Ser Trp
        130                 135                 140
Lys Thr Thr Thr Ala Ser Thr Thr Ala Ser Asp Ser Pro Ser Thr Thr
145                 150                 155                 160
Ser Thr Thr Thr Thr Ala Ala Thr Thr Thr Thr Thr Thr Thr
                165                 170                 175
Ile Ser Thr Thr Val Ala Thr Ser Lys Pro Thr Thr Thr Gln Arg Phe
            180                 185                 190
Leu Pro Pro Phe Val Thr Lys Ala Ala Thr Arg Ala Thr Thr Leu
        195                 200                 205
Glu Thr Pro Thr Thr Ser Ile Pro Glu Thr Ser Val Leu Thr Glu Val
    210                 215                 220
Thr Thr Ser Arg Leu Val Pro Ser Ser Thr Ala Lys Pro Arg Ser Leu
225                 230                 235                 240
Pro Lys Pro Ser Thr Ser Arg Thr Ala Glu Pro Thr Glu Lys Ser Thr
                245                 250                 255
Ala Leu Pro Ser Ser Pro Thr Thr Leu Pro Pro Thr Glu Ala Pro Gln
            260                 265                 270
Val Glu Pro Gly Glu Leu Thr Thr Val Leu Asp Ser Asp Leu Glu Val
        275                 280                 285
Pro Thr Ser Ser Gly Pro Ser Gly Asp Phe Glu Ile Gln Glu Glu Glu
    290                 295                 300
Glu Thr Thr Arg Pro Glu Leu Gly Asn Glu Val Val Ala Val Val Thr
305                 310                 315                 320
Pro Pro Ala Ala Pro Gly Leu Gly Leu Asn Ala Glu Pro Gly Leu Ile
                325                 330                 335
Asp Asn Thr Ile Glu Ser Gly Ser Ser Ala Ala Gln Leu Pro Gln Lys
            340                 345                 350
Asn Ile Leu Glu Arg
        355

<210> SEQ ID NO 9
<211> LENGTH: 123
<212> TYPE: PRT
<213> ORGANISM: HOMO SAPIENS

<400> SEQUENCE: 9

Arg Ala Glu Leu Thr Ser Asp Lys Asp Lys Asp Met Tyr Leu Asp Asn
1               5                   10                  15
Ser Ser Ile Glu Glu Ala Ser Gly Val Tyr Pro Ile Asp Asp Asp Asp
            20                  25                  30
Tyr Ala Ser Ala Ser Gly Ser Gly Ala Asp Glu Asp Val Glu Ser Pro
        35                  40                  45
```

-continued

```
Glu Leu Thr Thr Thr Arg Pro Leu Pro Lys Ile Leu Leu Thr Ser Ala
     50                   55                   60

Ala Pro Lys Val Glu Thr Thr Leu Asn Ile Gln Asn Lys Ile Pro
 65                   70                   75                   80

Ala Gln Thr Lys Ser Pro Glu Glu Thr Asp Lys Glu Lys Val Asn Leu
                 85                   90                   95

Ser Asp Ser Glu Arg Lys Met Asp Pro Ala Glu Glu Asp Thr Asn Val
            100                 105                 110

Tyr Thr Glu Lys His Ser Asp Ser Leu Phe Lys
        115                 120
```

<210> SEQ ID NO 10
<211> LENGTH: 43
<212> TYPE: PRT
<213> ORGANISM: RATTUS RATTUS

<400> SEQUENCE: 10

```
Asp Met Tyr Leu Asp Ser Ser Ile Glu Glu Ala Ser Gly Leu Tyr
 1               5                  10                  15

Pro Ile Asp Asp Asp Asp Tyr Ser Ser Ala Ser Gly Ser Gly Ala Tyr
                20                  25                  30

Glu Asp Lys Gly Ser Pro Asp Leu Thr Thr Ser
         35                  40
```

<210> SEQ ID NO 11
<211> LENGTH: 43
<212> TYPE: PRT
<213> ORGANISM: MUS SP

<400> SEQUENCE: 11

```
Asp Met Tyr Leu Asp Asn Ser Ser Ile Glu Glu Ala Ser Gly Val Tyr
 1               5                  10                  15

Pro Ile Asp Asp Asp Asp Tyr Ser Ser Ala Ser Gly Ser Gly Ala Asp
                20                  25                  30

Glu Asp Ile Glu Ser Pro Val Leu Thr Thr Ser
         35                  40
```

<210> SEQ ID NO 12
<211> LENGTH: 42
<212> TYPE: PRT
<213> ORGANISM: RANA SP

<400> SEQUENCE: 12

```
Tyr Ile Asp Ser Thr Glu Ser Ser Gly Asn Tyr Pro Val Asp Asp Asp
 1               5                  10                  15

Asp Tyr Ser Ser Gly Ser Gly Ser Gly Ile Pro Ala Arg Gly Asp Asp
                20                  25                  30

Glu Asp Glu Asn Val Val Leu Thr Thr Val
         35                  40
```

<210> SEQ ID NO 13
<211> LENGTH: 10
<212> TYPE: PRT
<213> ORGANISM: HOMO SAPIEN
<220> FEATURE:
<221> NAME/KEY: Xaa
<222> LOCATION: (2)..(2)
<223> OTHER INFORMATION: Xaa at position 2 if present, represents Asn, Asp, or Ile
<220> FEATURE:
<221> NAME/KEY: Xaa
<222> LOCATION: (3)..(3)

```
<223> OTHER INFORMATION: Xaa at position 3 represents Phe or Tyr
<220> FEATURE:
<221> NAME/KEY: Xaa
<222> LOCATION: (4)..(4)
<223> OTHER INFORMATION: Xaa at position 4 if present, represents Glu,
      Ser, or Ala
<220> FEATURE:
<221> NAME/KEY: Xaa
<222> LOCATION: (5)..(5)
<223> OTHER INFORMATION: Xaa at position 5 if present, represents Leu,
      Gly, or Ser
<220> FEATURE:
<221> NAME/KEY: Xaa
<222> LOCATION: (6)..(6)
<223> OTHER INFORMATION: Xaa at position 6 if present, represents Ala,
      or Gly

<400> SEQUENCE: 13

Asp Xaa Xaa Xaa Xaa Xaa Ser Gly Ser Gly
1               5                   10

<210> SEQ ID NO 14
<211> LENGTH: 10
<212> TYPE: PRT
<213> ORGANISM: HOMO SAPIEN
<220> FEATURE:
<221> NAME/KEY: Xaa
<222> LOCATION: (1)..(1)
<223> OTHER INFORMATION: Xaa at position 1 represents an amino acid
      having an acidic sidechain
<220> FEATURE:
<221> NAME/KEY: Xaa
<222> LOCATION: (2)..(2)
<223> OTHER INFORMATION: Xaa at position 2 if present, represents Asn,
      Gln, Asp, Glu, Gly, Ala, Val, Ile, Leu, Ser, or Thr
<220> FEATURE:
<221> NAME/KEY: Xaa
<222> LOCATION: (3)..(3)
<223> OTHER INFORMATION: Xaa at position 3 if present, represents Phe,
      Tyr, Trp, Leu, or Ile
<220> FEATURE:
<221> NAME/KEY: Xaa
<222> LOCATION: (4)..(4)
<223> OTHER INFORMATION: Xaa at position 4 if present, represents Asp,
      Glu, Gly, Ala, Val, Ile, Leu, Ser, or Thr
<220> FEATURE:
<221> NAME/KEY: Xaa
<222> LOCATION: (5)..(5)
<223> OTHER INFORMATION: Xaa at position 5 if present, represents Gly,
      Ala, Val, Ile, Leu, Ser, or Thr
<220> FEATURE:
<221> NAME/KEY: Xaa
<222> LOCATION: (6)..(6)
<223> OTHER INFORMATION: Xaa at position 6 if present, represents Gly,
      Ala, Val, Ile, Leu, Ser, or Thr

<400> SEQUENCE: 14

Xaa Xaa Xaa Xaa Xaa Xaa Ser Gly Ser Gly
1               5                   10

<210> SEQ ID NO 15
<211> LENGTH: 28
<212> TYPE: PRT
<213> ORGANISM: HOMO SAPIEN
<220> FEATURE:
<221> NAME/KEY: Xaa
<222> LOCATION: (4)..(4)
<223> OTHER INFORMATION: Xaa at position 4 if present, represents Gly,
      Ala, Val, Leu, Ile, Cys, Ser, or Thr
<220> FEATURE:
<221> NAME/KEY: Xaa
<222> LOCATION: (5)..(5)
<223> OTHER INFORMATION: Xaa at position 5 represents Gly, Ala, Val,
      Leu, Ile, Cys, Ser or Thr
<220> FEATURE:
```

-continued

```
<221> NAME/KEY: Xaa
<222> LOCATION: (7)..(7)
<223> OTHER INFORMATION: Xaa at position 7 represents Gly, Ala, Val, Leu
      or Ile
<220> FEATURE:
<221> NAME/KEY: Xaa
<222> LOCATION: (27)..(27)
<223> OTHER INFORMATION: Xaa at position 27 represents Gly, Ala, Val,
      Leu, Ile, Cys, Ser or Thr

<400> SEQUENCE: 15

Gln Ile Val Xaa Xaa Asn Xaa Pro Pro Glu Asp Gln Asp Gly Ser Gly
1               5                   10                  15

Asp Asp Ser Asp Asn Phe Ser Gly Ser Gly Xaa Gly
            20                  25

<210> SEQ ID NO 16
<211> LENGTH: 60
<212> TYPE: PRT
<213> ORGANISM: MUS SP
<220> FEATURE:
<221> NAME/KEY: Xaa
<222> LOCATION: (4)..(4)
<223> OTHER INFORMATION: Xaa at position 4 if present, represents Gly,
      Ala, Val, Leu, Ile, Cys, Ser, or Thr
<220> FEATURE:
<221> NAME/KEY: Xaa
<222> LOCATION: (5)..(5)
<223> OTHER INFORMATION: Xaa at position 5 represents Gly, Ala, Val,
      Leu, Ile, Cys, Ser or Thr
<220> FEATURE:
<221> NAME/KEY: Xaa
<222> LOCATION: (7)..(7)
<223> OTHER INFORMATION: Xaa at position 7 represents Gly, Ala, Val, Leu
      or Ile
<220> FEATURE:
<221> NAME/KEY: Xaa
<222> LOCATION: (27)..(27)
<223> OTHER INFORMATION: Xaa at position 27 represents Gly, Ala, Val,
      Leu, Ile, Cys, Ser or Thr
<220> FEATURE:
<221> NAME/KEY: Xaa
<222> LOCATION: (31)..(31)
<223> OTHER INFORMATION: Xaa at position 31 represents Pro, Gln or Asn
<220> FEATURE:
<221> NAME/KEY: Xaa
<222> LOCATION: (33)..(33)
<223> OTHER INFORMATION: Xaa at position 33 if present, represents Ala,
      Val, Leu, Ile, or Met
<220> FEATURE:
<221> NAME/KEY: Xaa
<222> LOCATION: (37)..(37)
<223> OTHER INFORMATION: Xaa at position 37 represents Arg or Gln
<220> FEATURE:
<221> NAME/KEY: Xaa
<222> LOCATION: (39)..(39)
<223> OTHER INFORMATION: Xaa at position 39 represents Gly, Ala, Val,
      Leu, Ile, Thr or Ser
<220> FEATURE:
<221> NAME/KEY: Xaa
<222> LOCATION: (40)..(40)
<223> OTHER INFORMATION: Xaa at position 40 represents Pro, Ser or Thr
<220> FEATURE:
<221> NAME/KEY: Xaa
<222> LOCATION: (41)..(41)
<223> OTHER INFORMATION: Xaa at position 41 represents Pro, Ser or Thr
<220> FEATURE:
<221> NAME/KEY: Xaa
<222> LOCATION: (43)..(43)
<223> OTHER INFORMATION: Xaa at position 43 represents Ile, Leu, Phe,
      Tyr, or Trp
<220> FEATURE:
<221> NAME/KEY: Xaa
<222> LOCATION: (46)..(46)
<223> OTHER INFORMATION: Xaa at position 46 represents Gly, Ala, Val,
      Ile, Leu, Ser or Thr
```

```
<220> FEATURE:
<221> NAME/KEY: Xaa
<222> LOCATION: (47)..(47)
<223> OTHER INFORMATION: Xaa at position 47 represents Trp, Phe, Tyr,
      Gln or Asn
<220> FEATURE:
<221> NAME/KEY: Xaa
<222> LOCATION: (52)..(52)
<223> OTHER INFORMATION: Xaa at position 52 represents Ala, Val, Leu,
      Ile, Thr or Ser
<220> FEATURE:
<221> NAME/KEY: Xaa
<222> LOCATION: (55)..(55)
<223> OTHER INFORMATION: Xaa at position 55 represents Gly, Ala, Val,
      Leu, Ile, Ser or Thr
<220> FEATURE:
<221> NAME/KEY: Xaa
<222> LOCATION: (60)..(60)
<223> OTHER INFORMATION: Xaa at position 60 represents Gly, Ala, Val,
      Leu, Ile, Thr or Ser

<400> SEQUENCE: 16

Gln Ile Val Xaa Xaa Asn Xaa Pro Pro Glu Asp Gln Asp Gly Ser Gly
1               5                   10                  15

Asp Asp Ser Asp Asn Phe Ser Gly Ser Gly Xaa Gly Ala Leu Xaa Asp
            20                  25                  30

Xaa Thr Leu Ser Xaa Gln Xaa Xaa Xaa Thr Xaa Lys Asp Xaa Xaa Leu
        35                  40                  45

Leu Thr Ala Xaa Pro Thr Xaa Pro Glu Pro Thr Xaa
    50                  55                  60

<210> SEQ ID NO 17
<211> LENGTH: 21
<212> TYPE: DNA
<213> ORGANISM: MUS SP

<400> SEQUENCE: 17
gacaacttct ctggctctgg c                                         21

<210> SEQ ID NO 18
<211> LENGTH: 21
<212> TYPE: DNA
<213> ORGANISM: MUS SP

<400> SEQUENCE: 18
gccagagcca gagaagttgt c                                         21

<210> SEQ ID NO 19
<211> LENGTH: 14
<212> TYPE: DNA
<213> ORGANISM: MUS SP
<220> FEATURE:
<221> NAME/KEY: n
<222> LOCATION: (3)..(3)
<223> OTHER INFORMATION: n at position 3 represents A, T, C or G
<220> FEATURE:
<221> NAME/KEY: n
<222> LOCATION: (6)..(6)
<223> OTHER INFORMATION: n at position 6 represents A, T, C or G
<220> FEATURE:
<221> NAME/KEY: n
<222> LOCATION: (12)..(12)
<223> OTHER INFORMATION: n at position 12 represents A, T, C or G

<400> SEQUENCE: 19
ganggntctg gnga                                                 14

<210> SEQ ID NO 20
```

```
<211> LENGTH: 14
<212> TYPE: DNA
<213> ORGANISM: MUS SP
<220> FEATURE:
<221> NAME/KEY: n
<222> LOCATION: (3)..(3)
<223> OTHER INFORMATION: n at position 3 represents A, T, C or G
<220> FEATURE:
<221> NAME/KEY: n
<222> LOCATION: (9)..(9)
<223> OTHER INFORMATION: n at position 9 represents A, T, C or G
<220> FEATURE:
<221> NAME/KEY: n
<222> LOCATION: (12)..(12)
<223> OTHER INFORMATION: n at position 12 represents A, T, C or G

<400> SEQUENCE: 20
tcnccaganc cntc                                                          14

<210> SEQ ID NO 21
<211> LENGTH: 33
<212> TYPE: DNA
<213> ORGANISM: MUS SP

<400> SEQUENCE: 21
taccggatga agaagaagga cgaaggcagc tac                                     33

<210> SEQ ID NO 22
<211> LENGTH: 33
<212> TYPE: DNA
<213> ORGANISM: MUS SP

<400> SEQUENCE: 22
atggcctact tcttcttcct gcttccgtcg atg                                     33

<210> SEQ ID NO 23
<211> LENGTH: 12
<212> TYPE: DNA
<213> ORGANISM: MUS SP

<400> SEQUENCE: 23
gagttctacg cc                                                            12

<210> SEQ ID NO 24
<211> LENGTH: 12
<212> TYPE: DNA
<213> ORGANISM: MUS SP

<400> SEQUENCE: 24
ggcgtagaac tc                                                            12

<210> SEQ ID NO 25
<211> LENGTH: 20
<212> TYPE: DNA
<213> ORGANISM: MUS SP

<400> SEQUENCE: 25
ctaagcttat ccacgaagcc                                                    20

<210> SEQ ID NO 26
<211> LENGTH: 48
<212> TYPE: DNA
<213> ORGANISM: MUS SP

<400> SEQUENCE: 26
gccggatcct cagtgatggt ggtgatggtg gtccaaaagg ctctgaga                     48
```

<210> SEQ ID NO 27
<211> LENGTH: 45
<212> TYPE: DNA
<213> ORGANISM: MUS SP

<400> SEQUENCE: 27
gccggatcct cagtgatggt ggtgatggtg gtcaggttga ccagg       45

<210> SEQ ID NO 28
<211> LENGTH: 45
<212> TYPE: DNA
<213> ORGANISM: MUS SP

<400> SEQUENCE: 28
gccggatcct cagtgatggt ggtgatggtg gagcacaggc tctcc       45

<210> SEQ ID NO 29
<211> LENGTH: 47
<212> TYPE: DNA
<213> ORGANISM: MUS SP

<400> SEQUENCE: 29
gccggatcct cagtgatggt ggtgatggtg gctggtgggc tctggag     47

<210> SEQ ID NO 30
<211> LENGTH: 27
<212> TYPE: DNA
<213> ORGANISM: MUS SP

<400> SEQUENCE: 30
tgtgccagcg ccagcgaagt tgtcaga                           27

<210> SEQ ID NO 31
<211> LENGTH: 21
<212> TYPE: DNA
<213> ORGANISM: MUS SP

<400> SEQUENCE: 31
ctggcgctgg cacaggtgct t                                 21

<210> SEQ ID NO 32
<211> LENGTH: 18
<212> TYPE: DNA
<213> ORGANISM: MUS SP

<400> SEQUENCE: 32
cgccatcctg atcttcag                                     18

<210> SEQ ID NO 33
<211> LENGTH: 19
<212> TYPE: DNA
<213> ORGANISM: MUS SP

<400> SEQUENCE: 33
caggatggcg ctggggatg                                    19

<210> SEQ ID NO 34
<211> LENGTH: 175
<212> TYPE: PRT
<213> ORGANISM: MUS SP;HOMO SAPIEN

<400> SEQUENCE: 34

```
Met Arg Arg Ala Ala Leu Trp Leu Trp Leu Cys Ala Leu Ala Leu Arg
1               5                   10                  15

Leu Gln Pro Ala Leu Pro Gln Ile Val Ala Val Asn Val Pro Pro Glu
            20                  25                  30

Asp Gln Asp Gly Ser Gly Asp Asp Ser Asp Asn Phe Ser Gly Ser Gly
            35                  40                  45

Thr Gly Ala Leu Pro Asp Thr Leu Ser Arg Gln Thr Pro Ser Thr Trp
    50                  55                  60

Lys Asp Val Trp Leu Leu Thr Ala Thr Pro Thr Ala Pro Glu Pro Thr
65                  70                  75                  80

Ser Val Ser Asp Val Pro Arg Asp Leu Glu Val Val Ala Ala Thr Pro
            85                  90                  95

Thr Ser Leu Leu Ile Ser Trp Asp Ala Pro Ala Val Thr Val Arg Tyr
            100                 105                 110

Tyr Arg Ile Thr Tyr Gly Glu Thr Gly Gly Asn Ser Pro Val Gln Glu
            115                 120                 125

Phe Thr Val Pro Gly Ser Lys Ser Thr Ala Thr Ile Ser Gly Leu Lys
            130                 135                 140

Pro Gly Val Asp Tyr Thr Ile Thr Val Tyr Ala Val Thr Gly Arg Gly
145                 150                 155                 160

Asp Ser Pro Ala Ser Ser Lys Pro Ile Ser Ile Asn Tyr Arg Thr
                165                 170                 175
```

<210> SEQ ID NO 35
<211> LENGTH: 30
<212> TYPE: DNA
<213> ORGANISM: MUS SP

<400> SEQUENCE: 35
atgtcgactg caaccggcaa ctcggatcca                                30

<210> SEQ ID NO 36
<211> LENGTH: 24
<212> TYPE: DNA
<213> ORGANISM: MUS SP

<400> SEQUENCE: 36
ggctgcgctg gtgggctctg gagc                                      24

<210> SEQ ID NO 37
<211> LENGTH: 24
<212> TYPE: DNA
<213> ORGANISM: HOMO SAPIEN

<400> SEQUENCE: 37
accagcgcag ccgggagcat cacc                                      24

<210> SEQ ID NO 38
<211> LENGTH: 25
<212> TYPE: DNA
<213> ORGANISM: HOMO SAPIEN

<400> SEQUENCE: 38
ggctcgagaa gcttcactgg gtaac                                     25

<210> SEQ ID NO 39
<211> LENGTH: 235
<212> TYPE: PRT
<213> ORGANISM: MUS SP;HOMO SAPIEN

```
<400> SEQUENCE: 39

Met Arg Arg Ala Ala Leu Trp Leu Trp Leu Cys Ala Leu Ala Leu Arg
1               5                   10                  15

Leu Gln Pro Ala Leu Pro Gln Ile Val Ala Val Asn Val Pro Pro Glu
            20                  25                  30

Asp Gln Asp Gly Ser Gly Asp Ser Asp Asn Phe Ser Gly Ser Gly
        35                  40                  45

Thr Gly Ala Leu Pro Asp Thr Leu Ser Arg Gln Thr Pro Ser Thr Trp
    50                  55                  60

Lys Asp Val Trp Leu Leu Thr Ala Thr Pro Thr Ala Pro Glu Pro Thr
65                  70                  75                  80

Ser Ala Ala Gly Ser Ile Thr Thr Leu Pro Ala Leu Pro Glu Asp Gly
                85                  90                  95

Gly Ser Gly Ala Phe Pro Pro Gly His Phe Lys Asp Pro Lys Arg Leu
            100                 105                 110

Tyr Cys Lys Asn Gly Gly Phe Phe Leu Arg Ile His Pro Asp Gly Arg
            115                 120                 125

Val Asp Gly Val Arg Glu Lys Ser Asp Pro His Ile Lys Leu Gln Leu
130                 135                 140

Gln Ala Glu Glu Arg Gly Val Val Ser Ile Lys Gly Val Cys Ala Asn
145                 150                 155                 160

Arg Tyr Leu Ala Met Lys Glu Asp Gly Arg Leu Leu Ala Ser Lys Cys
                165                 170                 175

Val Thr Asp Glu Cys Phe Phe Phe Glu Arg Leu Glu Ser Asn Asn Tyr
            180                 185                 190

Asn Thr Tyr Arg Ser Arg Lys Tyr Thr Ser Trp Tyr Val Ala Leu Lys
            195                 200                 205

Arg Thr Gly Gln Tyr Lys Leu Gly Ser Lys Thr Gly Pro Gly Gln Lys
    210                 215                 220

Ala Ile Leu Phe Leu Pro Met Ser Ala Lys Ser
225                 230                 235

<210> SEQ ID NO 40
<211> LENGTH: 43
<212> TYPE: DNA
<213> ORGANISM: MUS SP;HOMO SAPIEN

<400> SEQUENCE: 40
gatggactct gacrwctwcr vwvktgsttc tggctctggc aca                    43

<210> SEQ ID NO 41
<211> LENGTH: 15
<212> TYPE: DNA
<213> ORGANISM: MUS SP

<400> SEQUENCE: 41
agagtcatcc ccaga                                                   15

<210> SEQ ID NO 42
<211> LENGTH: 15
<212> TYPE: DNA
<213> ORGANISM: MUS SP

<400> SEQUENCE: 42
acaggtgctt tgcca                                                   15

<210> SEQ ID NO 43
```

```
<211> LENGTH: 21
<212> TYPE: DNA
<213> ORGANISM: MUS SP

<400> SEQUENCE: 43
gccgaaagtt tattacatct g                                              21

<210> SEQ ID NO 44
<211> LENGTH: 15
<212> TYPE: PRT
<213> ORGANISM: MUS SP
<220> FEATURE:
<221> NAME/KEY: Xaa
<222> LOCATION: (1)..(1)
<223> OTHER INFORMATION: Xaa at positions 1 represents Asp or Glu
<220> FEATURE:
<221> NAME/KEY: Xaa
<222> LOCATION: (2)..(2)
<223> OTHER INFORMATION: Xaa at positions 2 if present, represents any
      amino acid
<220> FEATURE:
<221> NAME/KEY: Xaa
<222> LOCATION: (3)..(3)
<223> OTHER INFORMATION: Xaa at position 3 if present, represents any
      amino acid
<220> FEATURE:
<221> NAME/KEY: Xaa
<222> LOCATION: (4)..(4)
<223> OTHER INFORMATION: Xaa at position 4 if present, represents any
      amino acid
<220> FEATURE:
<221> NAME/KEY: Xaa
<222> LOCATION: (5)..(5)
<223> OTHER INFORMATION: Xaa at position 5 if present, represents any
      amino acid
<220> FEATURE:
<221> NAME/KEY: Xaa
<222> LOCATION: (6)..(6)
<223> OTHER INFORMATION: Xaa at position 6 if present, represents any
      amino acid
<220> FEATURE:
<221> NAME/KEY: Xaa
<222> LOCATION: (7)..(7)
<223> OTHER INFORMATION: Xaa at position 7 if present, represents any
      amino acid
<220> FEATURE:
<221> NAME/KEY: Xaa
<222> LOCATION: (8)..(8)
<223> OTHER INFORMATION: Xaa at position 8 if present, represents any
      amino acid
<220> FEATURE:
<221> NAME/KEY: Xaa
<222> LOCATION: (9)..(9)
<223> OTHER INFORMATION: Xaa at position 9 if present, represents any
      amino acid
<220> FEATURE:
<221> NAME/KEY: Xaa
<222> LOCATION: (10)..(10)
<223> OTHER INFORMATION: Xaa at position 10 if present, represents any
      amino acid
<220> FEATURE:
<221> NAME/KEY: Xaa
<222> LOCATION: (11)..(11)
<223> OTHER INFORMATION: Xaa at position 11 if present, represents any
      amino acid

<400> SEQUENCE: 44

Xaa Xaa Xaa Xaa Xaa Xaa Xaa Xaa Xaa Xaa Xaa Ser Gly Ser Gly
 1               5                  10                  15

<210> SEQ ID NO 45
<211> LENGTH: 10
<212> TYPE: PRT
<213> ORGANISM: Drosophila sp.
```

-continued

```
<400> SEQUENCE: 45

Asp Pro Asp Tyr Ser Gly Ser Gly Phe Gly
1               5                   10

<210> SEQ ID NO 46
<211> LENGTH: 5
<212> TYPE: PRT
<213> ORGANISM: MUS SP
<220> FEATURE:
<221> NAME/KEY: Xaa
<222> LOCATION: (1)..(1)
<223> OTHER INFORMATION: Xaa at position 1 represents Asp or Glu
<220> FEATURE:
<221> NAME/KEY: Xaa
<222> LOCATION: (2)..(2)
<223> OTHER INFORMATION: Xaa at position 2 represents Gly or any amino
      acid
<220> FEATURE:
<221> NAME/KEY: Xaa
<222> LOCATION: (5)..(5)
<223> OTHER INFORMATION: Xaa at position 5 represents Asp or Glu

<400> SEQUENCE: 46

Xaa Xaa Ser Gly Xaa
1               5
```